(12) United States Patent
Rangwala et al.

(10) Patent No.: US 12,246,025 B2
(45) Date of Patent: Mar. 11, 2025

(54) METHODS OF TREATING CANCER WITH A COMBINATION OF A PLATINUM-BASED AGENT AND AN ANTI-TISSUE FACTOR ANTIBODY-DRUG CONJUGATE

(71) Applicant: Genmab A/S, Copenhagen V (DK)

(72) Inventors: Reshma Abdulla Rangwala, Philadelphia, PA (US); Esther C. W. Breij, Utrecht (NL); Sandra Verploegen, Nieuwegein (NL); Oyewale O. Abidoye, Bellevue, WA (US); Leonardo Viana Nicacio, Redmond, WA (US)

(73) Assignee: Genmab A/S, Valby (DK)

( * ) Notice: Subject to any disclaimer, the term of this patent is extended or adjusted under 35 U.S.C. 154(b) by 1207 days.

(21) Appl. No.: 16/982,008

(22) PCT Filed: Mar. 20, 2019

(86) PCT No.: PCT/US2019/023218
§ 371 (c)(1),
(2) Date: Sep. 17, 2020

(87) PCT Pub. No.: WO2019/183253
PCT Pub. Date: Sep. 26, 2019

(65) Prior Publication Data
US 2021/0015939 A1     Jan. 21, 2021

Related U.S. Application Data

(60) Provisional application No. 62/753,730, filed on Oct. 31, 2018, provisional application No. 62/646,256, filed on Mar. 21, 2018.

(51) Int. Cl.
| | | |
|---|---|---|
| *C07K 16/36* | (2006.01) | |
| *A61K 9/00* | (2006.01) | |
| *A61K 31/555* | (2006.01) | |
| *A61K 33/243* | (2019.01) | |
| *A61K 47/68* | (2017.01) | |
| *A61P 35/00* | (2006.01) | |

(52) U.S. Cl.
CPC .......... *A61K 31/555* (2013.01); *A61K 9/0019* (2013.01); *A61K 47/68031* (2023.08); *A61K 47/6843* (2017.08); *A61P 35/00* (2018.01)

(58) Field of Classification Search
None
See application file for complete search history.

(56) References Cited

U.S. PATENT DOCUMENTS

| | | |
|---|---|---|
| 5,223,427 A | 6/1993 | Edgington et al. |
| 5,661,016 A | 8/1997 | Lonberg |
| 5,814,318 A | 9/1998 | Lonberg et al. |
| 5,874,299 A | 2/1999 | Lonberg et al. |
| 5,877,397 A | 3/1999 | Lonberg et al. |
| 5,879,677 A | 3/1999 | Del Zoppo |
| 5,981,216 A | 11/1999 | Kenten |
| 6,274,142 B1 | 8/2001 | Obrien et al. |
| 6,884,879 B1 | 4/2005 | Baca |
| 7,405,227 B2 | 7/2008 | Kun et al. |
| 7,425,328 B2 | 9/2008 | Wang |
| 7,498,298 B2 | 3/2009 | Doronina |
| 7,605,235 B2 | 10/2009 | Anderson et al. |
| 7,824,677 B2 | 11/2010 | Wong et al. |
| 8,354,509 B2 | 1/2013 | Carven |
| 8,372,396 B2 | 2/2013 | Andya |
| 8,900,587 B2 | 12/2014 | Carven |
| 9,068,011 B2 | 6/2015 | Neijssen et al. |
| 9,150,658 B2 | 10/2015 | Verploegen |
| 9,168,314 B2 | 10/2015 | Satijn et al. |
| 9,492,565 B2 | 11/2016 | Satijn |
| 9,657,107 B2 | 5/2017 | Neijssen et al. |
| 9,714,297 B2 | 7/2017 | Verploegen |
| 9,834,606 B2 | 12/2017 | Li et al. |
| 10,501,550 B2 | 12/2019 | Wang et al. |
| 10,617,764 B2 | 4/2020 | Valbjørn |
| 2003/0017664 A1 | 1/2003 | Pnueli et al. |
| 2004/0044187 A1 | 3/2004 | Sato et al. |
| 2005/0028649 A1 | 2/2005 | Settanni |
| 2005/0169927 A1 | 8/2005 | Freskgaard et al. |
| 2005/0220793 A1 | 10/2005 | Anderson et al. |
| 2005/0276812 A1 | 12/2005 | Ebens, Jr. |
| 2006/0034846 A1 | 2/2006 | Ezban et al. |
| 2007/0031402 A1 | 2/2007 | Zhang |
| 2007/0110812 A1 | 5/2007 | Xia et al. |
| 2007/0166309 A1 | 7/2007 | Lazar |
| 2007/0196364 A1 | 8/2007 | Krishnamurthy et al. |
| 2008/0267968 A1 | 10/2008 | Fyfe |
| 2008/0305044 A1 | 12/2008 | Mcdonagh et al. |

(Continued)

FOREIGN PATENT DOCUMENTS

| | | |
|---|---|---|
| CN | 1303431 A | 7/2001 |
| CN | 1575302 A | 2/2005 |

(Continued)

OTHER PUBLICATIONS

ADC Review 2016—"Tisotumab Vedotin|TIVDAK|Humax®-TF-ADC," 1 page.

(Continued)

*Primary Examiner* — Ilia I Ouspenski
(74) *Attorney, Agent, or Firm* — MORRISON & FOERSTER LLP

(57) ABSTRACT

The invention provides a platinum-based agent (e.g., carboplatin) in combination with an antibody-drug conjugate that binds to tissue factor (TF) (e.g., tisotumab vedotin) and their use in methods of treating cancer, such as bladder cancer and cervical cancer. The invention also provides compositions and kits comprising the platinum-based agent (e.g., carboplatin) and the antibody-drug conjugate that binds to TF (e.g., tisotumab vedotin) for use in treating cancer, such as bladder cancer and cervical cancer.

25 Claims, 14 Drawing Sheets
Specification includes a Sequence Listing.

(56) References Cited

U.S. PATENT DOCUMENTS

| | | |
|---|---|---|
| 2009/0217401 A1 | 8/2009 | Korman |
| 2009/0232734 A1 | 9/2009 | Anderson et al. |
| 2009/0280056 A1 | 11/2009 | Dennis et al. |
| 2011/0104184 A1 | 5/2011 | Jiao et al. |
| 2011/0268751 A1 | 11/2011 | Sievers |
| 2011/0300156 A1 | 12/2011 | Verploegen |
| 2013/0101608 A1 | 4/2013 | Satijn |
| 2013/0216548 A1 | 8/2013 | Neijssen et al. |
| 2014/0341902 A1 | 11/2014 | Maecker |
| 2015/0329642 A1 | 11/2015 | Neijssen et al. |
| 2016/0053020 A1 | 2/2016 | Verploegen |
| 2016/0067349 A1 | 3/2016 | Satijn |
| 2016/0120976 A1 | 5/2016 | Goldenberg et al. |
| 2016/0272708 A1 | 9/2016 | Chen |
| 2016/0279258 A1 | 9/2016 | Valbjørn |
| 2016/0303231 A1 | 10/2016 | Iannone et al. |
| 2016/0376367 A1 | 12/2016 | Yuan et al. |
| 2017/0080103 A1 | 3/2017 | Ariaans et al. |
| 2017/0136130 A1 | 5/2017 | Satijn |
| 2017/0210806 A1 | 7/2017 | Liu |
| 2017/0253933 A1 | 9/2017 | Wang |
| 2017/0275375 A1 | 9/2017 | Rossi |
| 2017/0285037 A1 | 10/2017 | Kulangara et al. |
| 2017/0313782 A1 | 11/2017 | Neijssen et al. |
| 2017/0320962 A1 | 11/2017 | Neijssen et al. |
| 2017/0334995 A1 | 11/2017 | Zettl et al. |
| 2018/0044431 A1 | 2/2018 | Verploegen |
| 2018/0051085 A1 | 2/2018 | Chang et al. |
| 2019/0030178 A1 | 1/2019 | Lisby |
| 2019/0169311 A1 | 6/2019 | Verploegen |
| 2019/0201543 A1 | 7/2019 | Yu et al. |
| 2019/0315880 A1 | 10/2019 | Satijn |
| 2020/0079872 A1 | 3/2020 | Neijssen et al. |
| 2020/0246477 A1 | 8/2020 | Valbjørn |
| 2021/0019595 A1 | 1/2021 | Konisho |
| 2021/0030888 A1 | 2/2021 | Rangwala |
| 2021/0107980 A1 | 4/2021 | Rangwala et al. |
| 2021/0171657 A1 | 6/2021 | Verploegen et al. |
| 2021/0177987 A1 | 6/2021 | Rangwala et al. |
| 2021/0308208 A1 | 10/2021 | Rangwala et al. |
| 2021/0395384 A1 | 12/2021 | Satijn et al. |
| 2021/0402003 A1 | 12/2021 | Rangwala et al. |
| 2022/0088191 A1 | 3/2022 | Rangwala et al. |
| 2022/0265844 A1 | 8/2022 | Lisby et al. |
| 2022/0387485 A1 | 12/2022 | Rangwala et al. |
| 2023/0027495 A1 | 1/2023 | Rangwala |
| 2023/0263902 A1 | 8/2023 | Rangwala |
| 2023/0416403 A1* | 12/2023 | Verploegen .......... A61P 15/14 |
| 2024/0091373 A1* | 3/2024 | Valbjørn et al. ........ C07K 16/36 |
| 2024/0252673 A1 | 8/2024 | Rangwala |
| 2024/0294661 A1 | 9/2024 | Satijn |

FOREIGN PATENT DOCUMENTS

| | | | |
|---|---|---|---|
| CN | 101237881 A | 8/2008 |
| CN | 101652389 A | 2/2010 |
| CN | 101677987 A | 3/2010 |
| CN | 103119065 A | 5/2013 |
| CN | 103124564 A | 5/2013 |
| CN | 107840887 A | 3/2018 |
| EP | 1374896 A1 | 1/2004 |
| EP | 1676574 A2 | 7/2006 |
| EP | 1069185 B1 | 6/2011 |
| EP | 2991683 | 3/2016 |
| JP | H05172811 A | 7/1993 |
| JP | H05244988 A | 9/1993 |
| JP | H09302000 A | 11/1997 |
| JP | 2001213804 A | 8/2001 |
| JP | 2001516214 A | 9/2001 |
| JP | 2005512970 A | 5/2005 |
| JP | 2007196364 A | 8/2007 |
| JP | 2009503105 A | 1/2009 |
| JP | 2009185261 A | 8/2009 |
| JP | 2010530872 A | 9/2010 |
| JP | 2013527832 A | 7/2013 |
| JP | 2013532148 A | 8/2013 |
| TW | 202003046 A | 1/2020 |
| TW | 202034958 A | 10/2020 |
| WO | 198605807 A1 | 10/1986 |
| WO | 198807543 A1 | 10/1988 |
| WO | 198901036 A1 | 2/1989 |
| WO | 198911297 A1 | 11/1989 |
| WO | 198912463 A1 | 12/1989 |
| WO | 199206711 A1 | 4/1992 |
| WO | 199311227 A1 | 6/1993 |
| WO | 199312227 A1 | 6/1993 |
| WO | 199317105 A1 | 9/1993 |
| WO | 199405328 A1 | 3/1994 |
| WO | 199411029 A1 | 5/1994 |
| WO | 199601653 A1 | 1/1996 |
| WO | 199640921 A1 | 12/1996 |
| WO | 199704801 A1 | 2/1997 |
| WO | 199840408 A1 | 9/1998 |
| WO | 199856418 A1 | 12/1998 |
| WO | 200127079 A2 | 4/2001 |
| WO | 200170984 A2 | 9/2001 |
| WO | 200170984 A3 | 2/2002 |
| WO | 200211753 A1 | 2/2002 |
| WO | 2002096457 A2 | 12/2002 |
| WO | 2002096457 A3 | 2/2003 |
| WO | 2003009817 A2 | 2/2003 |
| WO | 2003020111 A2 | 3/2003 |
| WO | 2003029295 A1 | 4/2003 |
| WO | 2003037361 A2 | 5/2003 |
| WO | 2003037911 A2 | 5/2003 |
| WO | 2003039485 A2 | 5/2003 |
| WO | 2003070275 A1 | 8/2003 |
| WO | 2003009817 A3 | 11/2003 |
| WO | 2003093422 A2 | 11/2003 |
| WO | 2003037911 A3 | 12/2003 |
| WO | 2003020111 A3 | 1/2004 |
| WO | 2004004639 A2 | 1/2004 |
| WO | 2004004639 A3 | 1/2004 |
| WO | 2004007557 A2 | 1/2004 |
| WO | 2003039485 A3 | 2/2004 |
| WO | 2004016286 A2 | 2/2004 |
| WO | 2003037361 A3 | 3/2004 |
| WO | 2004007557 A3 | 4/2004 |
| WO | 2004039842 A2 | 5/2004 |
| WO | 2004041296 A2 | 5/2004 |
| WO | 2004041302 A1 | 5/2004 |
| WO | 2003093422 A3 | 7/2004 |
| WO | 2004016286 A3 | 7/2004 |
| WO | 2004041296 A3 | 7/2004 |
| WO | 2004055164 A2 | 7/2004 |
| WO | 2004064870 A2 | 8/2004 |
| WO | 2004071439 A2 | 8/2004 |
| WO | 2004039842 A3 | 9/2004 |
| WO | 2004094475 A2 | 11/2004 |
| WO | 2004110363 A2 | 12/2004 |
| WO | 2005000896 A2 | 1/2005 |
| WO | 2005001038 A2 | 1/2005 |
| WO | 2005004793 A2 | 1/2005 |
| WO | 2005000896 A3 | 2/2005 |
| WO | 2004094475 A3 | 3/2005 |
| WO | 2005020927 A2 | 3/2005 |
| WO | 2005025623 A2 | 3/2005 |
| WO | 2004064870 A3 | 4/2005 |
| WO | 2004071439 A3 | 7/2005 |
| WO | 2005004793 A3 | 7/2005 |
| WO | 2005072126 A2 | 8/2005 |
| WO | 2005079766 A2 | 9/2005 |
| WO | 2005079766 A3 | 10/2005 |
| WO | 2005020927 A3 | 11/2005 |
| WO | 2005025623 A3 | 12/2005 |
| WO | 2005118646 A2 | 12/2005 |
| WO | 2005001038 A3 | 2/2006 |
| WO | 2006014965 A2 | 2/2006 |
| WO | 2006044908 A2 | 4/2006 |
| WO | 2004110363 A3 | 5/2006 |
| WO | 2006065533 A2 | 6/2006 |
| WO | 2006044908 A3 | 8/2006 |
| WO | 2006121168 A1 | 11/2006 |
| WO | 2007008600 A2 | 1/2007 |

(56) References Cited

FOREIGN PATENT DOCUMENTS

| | | |
|---|---|---|
| WO | 2007019232 A2 | 2/2007 |
| WO | 2006014965 A3 | 3/2007 |
| WO | 2005072126 A3 | 5/2007 |
| WO | 2007056352 A2 | 5/2007 |
| WO | 2007059782 A1 | 5/2007 |
| WO | 2006065533 A3 | 6/2007 |
| WO | 2007019232 A3 | 6/2007 |
| WO | 2007076091 A2 | 7/2007 |
| WO | 2007076091 A3 | 7/2007 |
| WO | 2007097810 A2 | 8/2007 |
| WO | 2007097810 A3 | 11/2007 |
| WO | 2005118646 A3 | 1/2008 |
| WO | 2007008600 A3 | 1/2008 |
| WO | 2008030260 A2 | 3/2008 |
| WO | 2008030260 A3 | 3/2008 |
| WO | 2008100805 A2 | 8/2008 |
| WO | 2008100805 A3 | 10/2008 |
| WO | 2008137382 A1 | 11/2008 |
| WO | 2009002425 A2 | 12/2008 |
| WO | 2007056352 A3 | 4/2009 |
| WO | 2009048967 A1 | 4/2009 |
| WO | 2004055164 A3 | 7/2009 |
| WO | 2009002425 A3 | 12/2009 |
| WO | 2010059787 A1 | 5/2010 |
| WO | 2010066803 A2 | 6/2010 |
| WO | 2010081004 A1 | 7/2010 |
| WO | 2010066803 A3 | 8/2010 |
| WO | 2011119487 A2 | 9/2011 |
| WO | 2011157741 A2 | 12/2011 |
| WO | 2011157741 A3 | 3/2012 |
| WO | 200127079 A3 | 4/2013 |
| WO | 2011119487 A3 | 5/2013 |
| WO | 2013173223 A1 | 11/2013 |
| WO | 2013173337 A2 | 11/2013 |
| WO | 2014047221 A1 | 3/2014 |
| WO | 2014177771 A1 | 11/2014 |
| WO | 2015075201 A1 | 5/2015 |
| WO | 2015075477 A1 | 5/2015 |
| WO | 2013173337 A3 | 6/2015 |
| WO | 2015088847 A1 | 6/2015 |
| WO | 2015126903 A1 | 8/2015 |
| WO | 2015177360 A1 | 11/2015 |
| WO | 2016032927 A1 | 3/2016 |
| WO | 2017019846 A1 | 2/2017 |
| WO | 2017024465 A1 | 2/2017 |
| WO | 2017025051 A1 | 2/2017 |
| WO | 2017040790 A1 | 3/2017 |
| WO | 2017042352 A1 | 3/2017 |
| WO | 2017055547 A1 | 4/2017 |
| WO | 2017071625 A1 | 5/2017 |
| WO | 2017087280 A1 | 5/2017 |
| WO | 2017106656 A1 | 6/2017 |
| WO | 2017133540 A1 | 8/2017 |
| WO | 2017166804 A1 | 10/2017 |
| WO | 2018036472 A1 | 3/2018 |
| WO | 2018103017 A1 | 6/2018 |
| WO | 2019089973 A1 | 5/2019 |
| WO | 2019136309 A1 | 7/2019 |
| WO | 2019173523 A1 | 9/2019 |
| WO | 2019217455 A1 | 11/2019 |
| WO | 2019217457 A1 | 11/2019 |
| WO | 2020037024 A1 | 2/2020 |
| WO | 2020092210 A1 | 5/2020 |
| WO | 2021089794 A1 | 5/2021 |
| WO | 2021090721 A1 | 5/2021 |

OTHER PUBLICATIONS

Almagro, J.C. et al. (Jan. 4, 2018). "Progress and Challenges in the Design and Clinical Development of Antibodies for Cancer Therapy." Front. Immunol. 8(1751):1-19.

AYD56882—(Aug. 19, 2010). "Human Anti-TF IgG Antibody 014 VH Protein Sequence," SEQ ID 5, 2 pages.

AYD56926—(Aug. 19, 2020). "Human Anti-TF IgG Antibody 098 VH Protein Sequence," SEQ ID 49, 2 pages.

AYD56930—(Aug. 19, 2010). "Human Anti-TF IgG Antibody 111 VH Protein Sequence," SEQ ID 53, 2 pages.

AYD56938—(Aug. 19, 2010). "Human Anti-TF IgG Antibody 114 VL Protein Sequence," SEQ ID 61, 2 pages.

AYD56982—(Aug. 19, 2010). "Human Anti-TF IgG Antibody 098 VL Protein Sequence," SEQ ID 105, 2 pages.

Beck, A. (Mar.-Apr. 2011, e-pub. Mar. 1, 2011). "Biosimilar, Biobetter and Next Generation Therapeutic Antibodies," Mabs. 3(2):107-110.

Borcoman, E, et al. (Jan. 3, 2017). "Pembrolizumab in Cervical Cancer—Latest Evidence and Clinical Usefulness," Ther. Adv. Med. Oncol. 9(6):431-439.

Brown, M. et al. (1996). "Tolerance to Single, but Not Multiple, Amino Acid Replacements in Antibody VH CDR2," J. Immunol. 156:3285-3291.

Champiat, S. et al. (Apr. 2016, e-pub. Dec. 28, 2015). "Management of Immune Checkpoint Blockades Dysimmune Toxicities: A Collaborative Position Paper," Ann. Oncol. 27(4):559-574.

Doronina, S.O. et al. (Aug. 2003). "Erraturm: Development of Potent Monoclonal Antibody Auristatin Conjugates for Cancer Therapy," Nat. Biotechnol. 21(8):941.

Eaton, J.S. et al. (2015). "Ocular Adverse Events Associated with Antibody-Drug Conjugates in Human Clinical Trials," Journal of Ocular Pharmacology and Therapeutics 31(10):589-604.

Edwards, B.M. et al. (Nov. 14, 2003). "The Remarkable Flexibility of the Human Antibody Repertoire; Isolation of Over One Thousand Different Antibodies to a Single Protein, BLyS," J. Mol. Biol. 334(1):103-118.

FDA (2006). "Requirements on Content and Format of Labeling for Human Prescription Drug and Biological Products Final Rule and Notices," 71(15):3922-3997, 76 pages.

Fessas, P. et al. (Apr. 2017). "A Molecular and Preclinical Comparison of the PD-1-Targeted T-Cell Checkpoint Inhibitors Nivolumab and Pembrolizumab," Seminar on Oncology 44(2):136-140.

Gencore Version 4.6.3. (1993-2023, run on: Jun. 28, 2023). "OM Protein-Protein Search, Using SW Model," 2 pages.

Gencore Version 4.6.3. (1993-2023, run on: Jun. 28, 2023). "OM Protein-Protein Search, Using SW Model," Perfect Score 616, 2 pages.

Goel, M. et al. (2004). "Plasticity within the Antigen-Combining Site May Manifest as Molecular Mimicry in the Humoral Immune Response," J. Immunol. 173(12):7358-7367.

González-Rodríguez, E. et al. (Jul. 2016, e-pub. Jun. 15, 2016). "Spanish Group for Cancer Immuno-Biotherapy (GETICA). Immune Checkpoint Inhibitors: Review and Mangement of Endocrine Adverse Events," The Oncologist 21(7):804-816.

Howard, D. et al. (2016). "Antibody-Drug Conjugates and Other Nanomedicines: The Frontier of Gynaecological Cancer Treatment," Interface Focus 6:20160054, 13 pages.

Ilie, M. et al. (2016, e-pub. Feb. 25, 2016). "Assessment of the PD-L1 Status by Immunohistochemistry: Challenges and Perspectives for Therapeutic Strategies in Lung Cancer Patients," Virchows Archiv. 468:511-525.

International Priliminary Report on Patentability, issued May 10, 2022, for PCT Application No. PCT/EP2020/081314, 9 pages.

International Search Report and Written Opinion, mailed Feb. 16, 2021, filed Nov. 6, 2022, for PCT Application No. PCT/EP2020/081314, 12 pages.

Kanyavuz, A. et al. (Jun. 2019, e-pub. Feb. 4, 2019). "Breaking the Law: Unconventional Strategies for Antibody Diversification," Nat. Rev. Immunol 19(6):355-368.

Lescar, J. et al. (Jul. 30, 1995). "Crystal Structure of a Cross-Reaction Complex Between Fab F9.13.7 and Guinea Fowl Lysozyme," The Journal of Biological Chemistry 276(30):18067-18076.

Linardou, H. et al. (Jul. 2016). "Toxicity Management of Immunotherapy for Patients with Metastatic Melanoma," Ann. Transl. Med. 4(14):272, 11 pages.

Lloyd, C. et al. (2009, e-pub. Oct. 29, 2008). "Modelling the Human Immune Response: Performance of a 1011 Human Antibody Repertoire Against a Broad Panel of Therapeutically Relevant Antigens," Protein Engineering, Design & Selection 22(3):159-168.

(56) References Cited

OTHER PUBLICATIONS

Lo, C. (Oct. 26, 2017). "Conjunctivitis," Retrieved from the Internet: https://www.drclementlo.com/health-update/72-conjunctivitis.html, 3 pages.
Nair, A.B. et al. (2016). "A Simple Practice Guide for Dose Conversion Between Animals and Humans," Journal of Basic and Clinical Pharmacy 7:27-31.
Rentero, I. et al. (2011). "Screening of Large Molecule Diversities by Phage Display," Chimia (Aarau) 65(11):843-845.
TFOS (2017). "A Patient's Guide to Artificial Tears," retrieved from the Internet:https://www.tearfilm.org/dettnews-a_patients_guide_to_artificial_tears/5523_5519/eng, 3 pages.
U.S. Appl. No. 18/065,196, filed Dec. 13, 2022, Valbjorn et al. (Copy not submitted herewith pursuant to the waiver of 37 C.F.R. § 1.98(a)(2)(iii) issued by the Office on Sep. 21, 2004).
U.S. Appl. No. 18/526,959, filed Dec. 1, 2023, Satijn et al. (Copy not submitted herewith pursuant to the waiver of 37 C.F.R. § 1.98(a)(2)(iii) issued by the Office on Sep. 21, 2004).
Vaede, D. et al. (Sep. 2010, e-pub. Sep. 15, 2010) "Prservatives in Eye Drops: Toward Awareness of Their Toxicity," J. Fr. Ophtalmol. 33(7):505-524, 4 pages. English Abstract.
Vanderstraeten, A. et al. (Jun. 2014, e-pub. Mar. 22, 2014). "Mapping the Immunosuppressive Environment in Uterine Tumors: Implications for Immunotherapy," Cancer Immunol. Immunother 63(6):545-557.
Vergote, I. et al. (2017, e-pub. Aug. 31, 2017). "A Phase IIa Study of Tisotumab Vedotin (HuMax®-TF-ADC) in Patients With Relapsed, Recurrent and/or Metastatic Cervical Cancer," ESMO, Madrid Annals of Oncology 28(5): Abstract 9310, 6 pages.
Yang, W. et al. (Aug. 2013). "Increased Expression of Programmed Death (PD)-1 and its Ligand PL-L1 Correlates with Impaired Cell-Mediated Immunity in High-Rish Human Papillomavirus-Related Cervical Intraepithelial Neoplasia," Immunology 139(4):513-522.
Zhang, Q. et al. (2012). "Reduced Expression of Tissue Factor Pathway Inhibitor-2 Contributes to Apoptosis and Angiogenesis in Cervical Cancer," Journal of Experimental & Clinical Cancer Research 31:1, 9 pages.
Abdulkadir, S. et al. (Apr. 2000). "Tissue Factor Expression and Angiogenesis in Human Prostate Carcinoma," Human Pathology 31(4):443-447.
ADCETRIS. (Nov. 2018). "Highlights of Prescribing Information. ADCETRIS® (Brentuximab Vedotin) for Injection, for Intravenous Use Initial U.S. Approval: 2011," ADCETRIS 42 pages.
Alley, S.C. et al. (2019). "Tisotumab Vedotin Induces Anti-Tumor Activity Through MMAE-Mediated, Fc-Mediated, and Fab-Mediated Effector Functions in Vitro," AACR (2019) American Abstract #221, Association for Cancer Research—110th Annual Meeting, 1 page.
Alley, S.C. et al. (Jun. 2013, e-pub. Apr. 6, 2013). "Analytical and Bioanalytical Technologies for Characterizing Antibody-Drug Conjugates,", Current Opinion in Chemical Biology 17(3):406-411.
Alley, S.C. et al. (Mar. 2008, e-pub. Mar. 4, 2008), "Contribution of Linker Stability to the Activities of Anticancer Immunoconjugates," Bioconjugate Chem. 19(3):759-765.
Amirkhosravi, A. et al. (1996). "The Importance of Platelets in the Expression of Monocyte Tissue Factor AntigenMeasured by a New Whole Blood Flow Cytometric Assay," Thrombosis and Haemostasis 75(1):87-95.
Anonymous (Aug. 19, 2021). "NCT03786081 Safety and Efficacy of Tisotumab Vedotin Monotherapy & in Combination With Other Cancer Agents in Subjects With Cervical Cancer," 9 pages.
Anonymous (Sep. 19, 2017). "ENGOT-cx1 Randomized Phase II of paclitaxel-carboplatin +/-Nintedanib Ongoing Trials—Status Update," 12 pages.
Aras, O. et al. (2004). "Induction and Microparticle- and Cell-Associated Intravascular Tissue Factor in Human Endotoxemia," Blood 103(12):4545-4553.
Aydin, F. et al., (2013). "Measurements of Tumor Size Using CT and PET Compared to Histopathological Size in Non-Small Cell Lung Cancer," Diagn. Interv. Radiol. 19(4):271-278.
Bartlett, N. et al. (2009). "Complete Remissions With Weekly Dosing of SGN-35, a Novel Antibody-Drug Conjugate (ADC) Targeting CD30 in a Phase I Dose-Escalation Study in Patients With Relapsed or Refractory Hodgkin Lymphoma (HL) or Systemic Anaplastic Large Cell Lymphoma (sALCL)," ASCO Abstract No. 8500, J. Cin. Oncol. 27:15S, 3 pages.
Bartlett, N.L. et al. (Feb. 15, 2008, e-pub. Dec. 13, 2007). "A Phase I Multidose Study of SGN-30 Immunotherapy in Patients With Refractory or Recurrent CD30+ Hematologic Malignancies," Blood 111:1848-1854.
Bauer, K.M. (2015). "Transitioning HuMax-TF-ADC Into the Clinic—Maximizing Clinical Knowledge in Early Stage Development," World ADC Summit, 27 pages.
Bauer, M.K. (2015). "Clinical Perspective of ADC Development," PEGS Boston, 27 pages.
Bhatt, P. et al. (2016, e-pub. Feb. 6, 2016). "Rol of Antibodies in Diagnosis and Treatment of Ovarian Cancer: Basic Approach and Clinical Status," Journal of Controlled Release 226:148-167.
Bird, R.E. et al. (1988). "Single-Chain Antigen-Binding Proteins," Science 242(4877):423-426.
Bizzarri, M. et al. (2016, Jul. 23, 2016). "Pharmacodynamics and Pharmacokinetics of Inositol(s) in Health and Disease," Expert Opin. Biol Ther. 12(10):1181-1196.
Blank, S. (2020). "InnovaTV 208: New Weekly Dosing Cohort in the Phase 2 Study of Tisotumab Vedotin in Platinum-Resistant Ovarian Cancer," ESMO, 1 page.
Blank, S.V. et al. (Mar. 2021). "innova TV 208: New Weekly Dosing Cohort in Phase 2 Study of Tisotumab Vedotin in Platinum-Resistant Ovarian Cancer," SGO, 2 pages. Abstract.
Breen, E.D. et al. (Sep. 2001). "Effect of Moisture on the Stability of a Lyophilized Humanized Monoclonal Antibody Formulation," 18(9):1345-1353.
Breij, E. (2013). "An Antibody-Drug Conjugate Targeting Tissue Factor With Broad Anti-Tumor Efficacy in Xenograft Models With Heterogeneous Tissue Factor Expression," Genmab, 1 page.
Breij, E. (2013). "Development of an Auristatin-Conjugated Therapeutic Antibody Against Tissue Factor for the Treatment of Solid Tumors," World ADC Summit, Frankfort, 33 pages.
Breij, E. (Dec. 17, 2013). "An Antibody-Drug Conjugate Targeting Tissue Factor With Broad Anti-Tumor Efficacy in Xenograft Models With Heterogeneous Tissue Factor Expression," Dutch Society for Immunology Annual Meeting, 16 pages.
Breij, E. (May 17-19, 2014). "Pre-Clinical Development of a Therapeutic Antibody-Drug Conjugate Targeting Tissue Factor," Informa Empowered Antibodies Congress: Antibody-Drug Conjugates, Barcelona, 46 pages.
Breij, E. (May 18-19, 2015). "Targeting Solid Cancers Using Antibody-Drug Conjugates Against the Novel ADC Targets Tissue Factor and AXL," World ADC Summit, London, 41 pages.
Breij, E. (Oct. 25, 2013). "Pre-Clinical Development of a Therapeutic Antibody-Drug Conjugate Targeting Tissue Factor," GTC Antibody & Protein Therapeutics Conference, San Diego, 47 pages.
Breij, E. et al. (2013). "Use of an Antibody-Drug Conjugate Targeting Tissue Factor to Induce Complete Tumor Regression in Xenograft Models With Heterogeneous Target Expression," ASCO 2013. 2 pages.
Breij, E.C.W. et al. (Apr. 6, 2013). "Abstract 1234: An Antibody-Drug Tissue Factor With Broad Anti-Tumor Efficacy in Xenograft Models With Heterogeneous Tissue Factor Expression," Cancer Research 73(Suppl. 1):1-3.
Burova, E. et al. (May 2017). "Characterization of the Anti-PD-1 Antibody REGN2810 and Its Antitumor Activity in Human PD-1 Knock-In Mice," Mol Cancer Ther. 16(5):861-870.
Calvert et al. (Nov. 1989). "Carboplatin Dosage: Prospective Evaluation of a Simple Formula Based on Renal Function." J. Clin. Oncol. 7(11):1748-1756.
Calvo et al. (Feb. 2018). Journal of Clinical Oncology 36(5 suppl.):58-58, 2 pages.
Candelaria, M. et al. (Dec. 2009). "Lack in Efficacy for Imatinib Mesylate as Second-Line Treatment of Recurrent or Metastatic

(56) References Cited

OTHER PUBLICATIONS

Cervical Cancer Expressing Platelet-Derived Growth Factor Receptor Alpha," Int. J. Gynecol. Cancer 19(9):1632-1637.
Carter, D. (Mar. 2014). "New Global Survey Shows an Increasing Cancer Burden," Am. J. Nurs. 114(3):17, 1 page.
Carter, M.C. et al. (Aug. 2, 1985). "Instability of Succinyl Ester Linkages in O2-Monosuccinyl Cyclic AMP-Protein Conjugates at Neutral pH." Journal of Immunological Methods 81(2):245-257.
Chen, C. et al. (Apr. 2005). "Characterization of Human Tissue Factor (TF)-Specific Monoclonal Antibodies Prepared USing a Rapid Immunization Protocol," Hybridoma 24(2):78-85.
Chen, J. et al. (Jun. 1993). "Immunoglobulin Gene Rearrangement in B Cell Deficient Mice Generated by Targeted Deletion of the JH Locus," International Immunology. 5(6):647-656.
Chen, T. et al. (1993). "Development of a Stable Lyophilized Formulation for a Monoclonal Antibody-Doxorubicin Conjugate," Pharmaceutical Research 10(10 Suppl.): p. S90, 1 page.
Chen, Z. et al. (Jan. 1995). "Differential Expression of Human Tissue Factor in Normal Mammary; Epithelial Cells and in Carcinomas," Molecular Medicine 1(2):153-160.
Chothia, C. et al. (Dec. 21-28, 1989). "Conformations of Immunoglobulin Hypervariable Regions," Nature 342(6252):877-883.
Chothia, C. et al. (Oct. 5, 1992). "Structural Repertoire of the Human VH Segments," J Mol Biol 227(3):799-817.
Chu, A.J. (2005). "Tissue Factor Mediates Inflammation," Archives of Biochemistry and Biophysics 440:123-132.
Clackson, T. et al. (Aug. 15, 1991). "Making Antibody Fragments Using Phage Display Libraries," Nature 352:624-628.
ClinicalTrial NCT02001623 "Tisotumab Vedotin (HuMax®-TF-ADC) Safety Study in Patients With Solid Tumors," retreived from https://clinicaltrials.gov/ct2/show/NCT02001623, last visited Dec. 31, 2019, 8 pages.
ClinicalTrial NCT02001623 (Sep. 22, 2016). "Tisotumab Vedotin (HuMax®-TF-ADC) Safety Study in Patients With Solid Tumors," 7 pages.
ClinicalTrial.gov. (2015). "HuMax®-TF-ADC Safety Study in Patients With Solid Tumors," Clinical Trials NCT02552121, 5 pages.
ClinicalTrials.gov. (Jul. 11, 2011), "A Phase I Dose Escalation Study of SGN-35 Alone and in Combination With Gemcitabine for CD30-Postive Malignancies," Clinical Trials NCT00649584, 4 pages.
Cocco, E. et al. (Jun. 22, 2011). "Expression of Tissue Factor in Adenocarcinoma and Squamous Cell Carcinoma of the Uterine Cervix: Implications for Immunotherapy With Hi-Con1, a Factor VII-Iggfc Chimeric Protein Targeting Tissue Factor," BMC Cancer 11:263, 10 pages.
Coleman, R.L. (2020). "Tisotumab Vedotin (TV) in Previously Treated Recurrent or Metastatic Cervical Cancer (r/mCC): Results From the Phase 2 InnovaTV 204/GOG-3023/ENGOT-cx6 Study," Virtual ESMO 2020, 17 pages.
Coleman, R.L. et al. (2018). "Abstract TPS5601—Poster 327b, a Single Arm, Phase 2, Multicenter, International Trial of Tisotumab Vedotin (HuMax® TF ADC) in Previously Treated, Recurrent or Metastatic Cervical Cancer," ASCO 2018, 1 page.
Coleman, R.L. et al. (2021, e-pub. Apr. 9, 2021). "Efficacy and Safety of Tisotumab Vedotin in Previously Treated Recurrent or Metastatic Cervical Cancer (InnovaTV 204/GOG-3023/ENGOT-cx6): A Multicentre, Open-Label, Single-Arm, Phase 2 Study," Lancet Oncol. 22:609-619.
Colman, P.M. (1994). "Effects of Amino Acid Sequence Changes on Antibody-Antigen Interactions" Research in Immunology 145:33-36.
Concin, N. et al (2017). "A Phase IIa study of Tisotumab Vedotin (HuMax®-TF-ADC) in patients with Relapsed, Recurrent and/or Metastatic Cervical Cancer: Updated Safety and Efficacy," ESGO 2017, 1 page.
Concin, N. et al. (2018). "A Phase IIa Study of Tisotumab Vedotin in Patients With Previously Treated Recurrent or Metastatic Cervical Cancer: Updated Analysis of Full Cervical Expansion Cohort," ESMO (2018) European Society for Medical Oncology 43rd Congress—ESMO 2018.

Connor, J. M. et al. (Jan. 25, 2018). "Brentuximabl Vedotin With Chemotherapy for Stage III or IV Hodgkin's Lymphoma," N. Eng. J. Med. 378(4):331-344.
Coronel, J. et al. (2009, e-pub. Oct. 28, 2008). "Weekly Topotecan as Second- or Third-Line Treatment in Patients With Recurrent or Metastatic Cervical Cancer," Med. Oncol. 26(2):210-214.
Das, C.J. et al., (Jul.-Sep. 2018). "Positron Emission Tomography in Prostate Cancer: An Update on State of the Art," Indian J. Urol. 34(3):172-179.
De Bono, J.S. (Mar. 2019, e-pub. Feb. 7, 2019). "Tisotumab vedotin in Patients With Advanced or Metastatic Solid Tumours (InnovaTV 201): A First-In-Human, Multicentre, Phase 1-2 Trial," Lancet Oncol. 20(3):383-393.
De Goeij, B. (2014). "High Turnover of Tissue Factor Enables Efficient Intracellular Delivery of Antibody-Drug Conjugates," MAM 2014, Mykonos, 38 pages.
De Goeij, B. (2015). Targeting Solid Cancers Using Antibody-Drug Conjugate Against the Novel ADC Target Tissue Factor HuMax®-TF-ADC, a Preclinical and FIH Study, IBC Antibody Engineering and Therapeutics, 23 pages.
De Goeij, B. et al. (2015, e-pub. Feb. 27, 2015). "High Turnover of Tissue Factor Enables Efficient Intracellular Delivery of Antibody-Drug Conjugates," Molecular Cancer Therapeutics 14:1130-1140.
Doronina, S.O. et al. (Jul. 2003). "Development of Potent Monoclonal Antibody Auristatin Conjugates for Cancer Therapy," Nat. Biotechnol. 21(7):778-784.
Doronina, S.O. et al. (Jan. 2006). "Enhanced Activity of Monomethylauristatin F Through Monoclonal Antibody Delivery: Effects of Linker Technology on Efficacy and Toxicity," Bioconjug. Chem. 17(1):114-124.
Doronina, S.O. et al. (Oct. 2008, e-pub. Sep. 20, 2008). "Novel Peptide Linkers for Highly Potent Antibody—Auristain Conjugate," Bloconguate Chem. 19:1960-1963.
Drake, T.A. et al. (1989). "Selective Cellular Expression of Tissue Factor in Human Tissues," American Journal of Pathology 134(5):1087-1097.
drugs.com. (Jun. 2008). "Seattle Genetics Reports Multiple Complete and Partial Responses With SGN-35 in Patients With Lymphoma," Drugs.Com, 3 pages.
Dubowchik, G.M. et al. (Aug. 1999). "Receptor-Mediated and Enzyme-Dependent Targeting of Cytotoxic Anticancer Drugs," Pharm. Therapeutics 83(2):67-123.
Egorina, E.M. et al. (2005). "Intracellular and Surface Distribution of Monocyte Tissue Factor, Application to Intersubject Variability," Arterioscler. Thromb. Vase. Biol. 25:1493-1498, 13 pages.
Fanale, M. et al. (2009). "The Antibody-Drug Conjugate Brentuximab Vedotin (SGN-35) Induced Multiple Objective Responses in Patients With Relapsed or Refractory CD30-Positive Lymphomas in a Phase 1 Weekly Dosing Study," Blood 114:2731, 5 pages.
Fiorica, J.V. et al. (Nov. 2009, e-pub. Sep. 2, 2009). "A Phase II Evaluation of Weekly Topotecan as a Single Agent Second Line Therapy in Persistent or Recurrent Carcinoma of the Cervix: A Gynecologic Oncology Group Study," Gynecol. Oncol. 115(2):285-289.
Fleck, R. et al. (1990). "Localization of Human Tissue Factor Antigen by Immunostaining with Monospecific, Polyclonal Anti-Human Tissue Factor Antibody," Thrombosis Research 59:421-437.
Forero, A. et al. (2005). "Leukemia, Lymphoma, Myeloma, and Transplantation (Adult). Initial Phase II Results of SGN-30 (Anti-CD30 Monoclonal Antibody) in Patients With Refractory or Recurrent Systemic Anaplastic Large Cell Lymphoma (ALCL)," Journal of Clinical Oncology Abstract No. 6601, 1 page.
Francisco, J.A. et al. (Aug. 15, 2003, e-pub. May 8, 2003). "cAC10-vcMMAE, an Anti-CD30-Monomethyl Auristatin E Conjugate With Potent and Selective Antitumor Activity," Blood 102:1458-1465.
Gaffney, D. et al. (2018, e-pub. Oct. 6, 2018). "Too Many Women Are Dying From Cervi Cancer: Problems and Solutions," Gynecologic Oncology 151(3):547-554.
Garcia, A.A. et. al. (Aug. 2007). "Phase II Clinical Trial of Docetaxel in Refractory Squamous Cell Carcinoma of the Cervix: A Gynecologic Oncology Group Study," Am. J. Clin. Oncol. 30(4):428-431.

(56) References Cited

OTHER PUBLICATIONS

Genmab (2011). "Development of ADCs against Tissue Factor for the treatment of Solid Tumors," World ADC Summit, Oct. 25-28, 2011, San Francisco, slideshow, 22 pages.
Gerritsen, A. (2013). "Bioanalysis of Antibody-Auristatin Conjugates in Primate Studies," 6th Monoclonal Antibodies Workshop, Basel, 28 pages.
Gerritsen, A. (Jun. 2012). "In Vitro Screening Approaches for Antibody Drug Conjugate Candidates," 2nd Annual Antibodies Congress, Berlin Jun. 13-14, 2012, 29 pages.
Gerritsen, A. (Jun. 29-Jul. 3, 2015). "Bioanalysis in ADC Development," Global Bioconference, Incheon, Korea, 1 page.
Gessler, F. et al. (2010). "Inhibition of Tissue Factor/Protease-Activated Receptor-2 Signaling Limits Proliferation, Migration, and Invasion ofMalignantGlioma Cells," Neuroscience 165:1312-1322.
Goh, V. et al. (2014). "Perfusion CT Imaging of Colorectal Cancer," Br. J. Radiol. 87(1034):20130811, 9 pages.
Goldberg, R.M. et al. (Jan. 2007). "The Continuum of Care: A Paradigm for the Management of Metastatic Colorectal Cancer," Oncologist 12(1):38-50.
Gray, E. (2020). "Tisotumab Vedotin Shows Immunomodulatory Activity Through Induction of Immunogenic Cell Death," SITC, 1 page.
Gruber, I.V. et al. (Jul. 5, 2013). "Measurement of Tumour Size With Mammography, Sonography and Magnetic Resonance Imaging as Compared to Histological Tumour Size in Primary Breast Cancer," BMC Cancer 13:328, 8 pages.
Haeuw, J-F. et al. (Dec. 2009). "Immunoconjugates, Drug-Armed Antibodies to Fight Against Cancer," Med. Sci 25:1046-1052, English Abstract Only.
Hamblett, K.J. et al. (Oct. 15, 2004). "Effects of Drug Loading on the Antitumor Activity of a Monoclonal Antibody Drug Conjugate," Clin. Cancer Res. 10:7063-7070.
Hamblett, K.J. et al. (2005). "SGN-35, an Anti-CD30 Antibody-Drug Conjugate, Exhibits Potent Antitumor Actrivity for the Treatement of CD30+ Malignancies," Blood 106:610. (Abstract Only).
Hamers-Casterman, C. et al. (Jun. 3, 1993). "Naturally Occurring Antibodies Devoid of Light Chains," Nature 363:446-448.
Hamid, O. et al. (Jul. 11, 2013, e-pub. Jun. 2, 2013). "Safety and Tumor Responses With Lambrolizumab (Anti-PD-1) in Melanoma," N. Engl. J. Med. 369(2):134-144, 18 pages.
Hamid, O. et al. (Jun. 2013, e-pub. Feb. 19, 2013). "Anti-Programmed Death-1 and Anti-Programmed Death-Ligand 1 Antibodies in Cancer Therapy," Expert Opin. Biol. Ther. 13(6):847-861. Abstract Submitted.
Hanker, L.C. et al. (Oct. 2012, e-pub. Aug. 21, 2012). "The Impact of Second to Sixth Line Therapy on Surviaval of Relapsed Ovarian Cancer After Primary Taxane/Platinum-Based Therapy," Ann. Oncol. 23(10):2605-2612.
Harlow, E. et al. (1988). Antibodies a Laboratory Manual, Table of Contents only, 9 pages.
Harris, J.R. et al. (2019). "Tisotumab Vedotin—A Novel Tissue Factor-Targeting Antibody-Drug Conjugate for the Treatment of Advanced Solid Tumors," PEGS Boston, 32 pages.
Harris, J.R. et al. (2019). "Tisotumab Vedotin—A Novel Tissue Factor-Targeting Antibody-Drug Conjugate for the Treatment of Advanced Solid Tumors," PEGS Boston, Abstract, 1 page.
Harris, R.E. et al. (Apr. 2005). "Aspirin, Ibuprofen, and Other Non-Steroidal Anti-Inflammatory Drugs in Cancer Prevention: A Critical Review of Non-Selective COX-2 Blockade (Review)," Oncol. Rep. 3(4):559-583.
Hemmingsen, P. (Jun. 2015). "Overcoming the Challenges of Your Supply Chain," Empowered Antibodies Congress, Barcelona, 30 pages.
Hermsen, M.A. et al (Jan. 1996). "Centromeric Breakage as a Major Cause of Cytogenetic Abnormalities in Oral Squamous Cell Carcinoma," Genes Chromosomes Cancer 15(1):1-9.
Hillemanns, P. et al. (2016, e-pub. Aug. 22, 2016). "Epidemiology and Early Detection of Cervical Cancer," Oncol. Res. Treat. 39(9):501-506.

Hjortoe, G.M. et al. (2004). "Tissue Factor-Factor VIIa-Specific Up-Regulation of IL-8 Expression in MDA-MB-231 Cells Is Mediated by PAR-2 and Results in Increases Cell Migration," Blood 103(8):3029-3037.
Hobbs, J.E. et al. (2007). "Alternatively Spliced Human Tissue Factor Promotes Tumor Growth and Angiogenesis in a Pancreatic Cancer Tumor Model," Thrombosis Res. 120(Suppl. 2):S13-S21.
Hodi, F.S. et al. (Jun. 5, 2010). "Improved Survival with Ipilimumab in Patients with Metastatic Melanoma," N. Engl. J. Med. 363:711-723.
Holden, S.N. et al. (2008). "A Phase I Study of Weekly Dosing of Trastuzumab-DM1 (T-DM1) in Patients With Advanced," ASCO Poster 1029, 1 page.
Hollebecque, A. et al. (Jun. 2-6, 2017). "Abstract 5504: An Open-Label, Multicohort, Phase I/II Study of Nivolumab in Patients With Virus-Associated Tumors (Checkmate 358: Efficacy and Safety in Recurrent or Metastatic Cervical, Vaginal and Vulvar Cancers," Presented at: ASCO Annual Meeting; Chicago, 4 pages.
Holt, L.J. et al. (Nov. 2003) "Domain Antibodies: Proteins for Therapy," Trends in Biotechnology 21(11):484-490.
Homesley, H.D. et al. (Feb. 2008, e-pub. Feb. 29, 2008). "A Phase II Trial of Weekly 1-Hour Paclitaxel as Second-Line Therapy for Endometrial and Cervical Cancer," Int. J. Clin. Oncol, 13(1):62-65.
Hong, D.S. et al. (2019). "Tisotumab Vedotin in Patients With Previously Treated Recurrent or Metastatic Cervical Cancer: Updated Safety and Efficacy Results From the Full Cervical Cohort of the Phase II InnovaTV 201 Study (NCT02001623," SGO Society of Gynecologic Oncology, 18 pages.
Hong, D.S. et al. (2019). "Tisotumab Vedotin in Patients With Previously Treated Recurrent or Metastatic Cervical Cancer: Updated Safety and Efficacy Results From the Full Cervical Cohort of the Phase II innovaTV 201 Study," SGO Society of Gynecologic Oncology, Abstract, 2 pages.
Hong, D.S. et al. (2019). "InnovaTV 207: Open Label Phase 2 Study of Tisotumab Vedotin for Locally Advanced or Metastatic Disease in Solid Tumors—TIP," ASCO American Society of Clinical Oncology—55th Annual Meeting, Poster, 1 page.
Hong, D.S. et al. (2021). "Efficacy and Safety of Tisotumab Vedotin in Patients With Head and Neck Squamous Cell Carcinoma: Resulats From a Phase II Cohort," Mutidisplinary Thoracic Cancers Symposium, 2 pages.
Hong, D.S. et al. (2021). "innovaTV 207: New Dosing Cohort in the Open Label Phase 2 Study of Tisotumab Vedotin in Solid Tumors," Poster, 1 page.
Hong, D.S. et al. (Mar. 15, 2020, e-pub. Dec. 3, 2019). "Tisotumab Vedotin in Patients With Previously Treated Recurrent or Metastatic Cervical Cancer," Clinical Cancer Research 26(6):1220-1228.
Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.
Houtkamp, M. (Apr. 25, 2017). "Target Expression Correlates to ADC Efficacy in Mouse Tumor Models," International Symposium for Tissue Phenomics, 29 pages.
Houtkamp, M. (Feb. 11, 2015). "Pre-Clinical Efficacy of an Antibody-Drug Conjugate Targeting TF in Solid Tumor PDX Models," CrownBio Symposium: Translation Tools in Oncology Drug Development, 20 pages.
Huang, J. et al. (Mar. 15, 2018, e-pub. Jan. 22, 2018). "Safety, Activity, and Biomarkers of SHR-1210, an Anti-PD-1 Antibody, for Patients with Advanced Esophageal Carcinoma," Clinical Cancer Research 24(6):1296-1304.
Huang, X. et al. (1997). "Tumor Infarction in Mice by Antibody-Directed Targeting of Tissue Factor to Tumor Vasculature," Science 275(5299):547-550.
Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
International Preliminary Report on Patentability and Written Opinion for Application No. PCT/EP2011/059917, 12 pages, dated Dec. 19, 2012.

(56) References Cited

OTHER PUBLICATIONS

International Preliminary Report on Patentability issued Apr. 27, 2021, for PCT Application No. PCT/US2019/058300, filed Oct. 28, 2019, 8 pages.
International Preliminary Report on Patentability issued Feb. 16, 2021, for PCT Application No. PCT/US2019/046467, filed Aug. 14, 2019, 6 pages.
International Preliminary Report on Patentability issued May 5, 2020, for PCT Application No. PCT/US2018/58771, filed Nov. 1, 2018, 5 pages.
International Preliminary Report on Patentability issued Nov. 10, 2020, for PCT Application No. PCT/US2019/031166, filed May 7, 2019, 6 pages.
International Preliminary Report on Patentability, issued Nov. 10, 2020, for PCT Application No. PCT/US2019/31168, 7 pages.
International Preliminary Report on Patentability, PCT/EP2014/075326, dated May 24, 2016, 8 pages.
International Search Report and Written Opinion for Application No. PCT/EP2009/066755, dated Jun. 28, 2010.
International Search Report and Written Opinion of the International Searching Authority, mailed Aug. 19, 2019, for PCT Application No. PCT/US2019/031166, filed May 7, 2019, 9 pages.
International Search Report and Written Opinion of the International Searching Authority, mailed Feb. 1, 2019, for PCT Application No. PCT/US2018/58771, filed Nov. 1, 2018, 12 pages.
International Search Report and Written Opinion of the International Searching Authority, mailed Feb. 10, 2020, for PCT/US2019/058300, filed Oct. 28, 2019, 16 pages.
International Search Report and Written Opinion of the International Searching Authority, mailed Nov. 22, 2019, for PCT Application No. PCT/US2019/046467, filed Aug. 14, 2019, 9 pages.
International Search Report and Written Opinion, for Application No. PCT/EP2011/059917, 19 pages, dated Dec. 23, 2011.
International Search Report and Written Opinion, mailed Sep. 24, 2019, for PCT Application No. PCT/US2019/31168, 11 pages.
International Search Report and Written Opinion, PCT/EP2014/075326, dated Mar. 10, 2015, 13 pages.
Jackson, D. et al. (2008). "A Human Antibody-Drug Conjugate Targeting EphA2 Inhibits Tumor Growth in vivo," Cancer Res. 68(22):9367-9374.
Janeway, C.A. et al. (1997). Immunobiology, 3rd edition Garland Press, pp. 3.1-3.11, 14 pages.
Jiang, Y. et al. (2019, e-pub. Mar. 19, 2019). "PD-1 and PD-L1 in Cancer Immunotherapy: Clinical Implications and Future Considerations," Human Vaccines & Immunotherapeutics 15(5):1111-1122.
Johnson, G. et al. (2003). "The Kabat Database and a Bioinformatics Example," Methods in Molecular Biology 248:11-25, 15 pages.
Johnson, M.L. et al. (Feb. 10, 2018). "Abstract 212: Phase I Trial of the Programmed Death Receptor 1 (PD-1) Inhibitor, BI 754091, in Patients (Pts) With Advanced Solid Tumors," Journal of Clinical Oncology 36(5 suppl.):212, 2 page.
Kerwin, B.A. (Aug. 2008). "Polysorbates 20 and 80 Used in the Formulation of Protein Biotherapeutics: Structure and Degradation Pathways," Journal of Pharmaceutical Sciences 97(8):2924-2935.
Kirchhofer, D. et al. (2000). "Epitope Location on Tissue Factor Determines the Anticoagulant Potency of Monoclonal Anti-tissue Factor Antibodies," Thromb. Haemnost. 84:1072-1081.
Lassen, U. et al. (2015). "A Phase I, First-in-Human Study to Evaluate the Tolerability, Pharmacokinetics and Preliminary Efficacy of HuMax®-Tissue Factor-ADC (TF-ADC) in Patients with Solid Tumors," ASCO Poster 2570, 1 page.
Lassen, U. et al. (May 30, 2015). "A Phase I, First-in-Human Study to Evaluate the Tolerability, Pharmacokinetics and Preliminary Efficacy of HuMax®-Tissue Factor-ADC (TF-ADC) in Patients with Solid Tumors," ASCO, Abstract 6 pages.
Lee, E.K. et al (2019, e-pub. Mar. 28, 2019). "Antibody-Drug Conjugates in Gynecologic Malignancies," Gynecologic Oncology 153:694-702.

Mackman, N. et al. (2007), "Role of the Extrinsic Pathway of Blood Coagulation in Hemostasis and Thrombosis," Arterioscler. Thromb. Vase. Biol. 27:1687-1693.
Mahdi, H. et al. (2019). "Phase 2 Trial of Tisotumab Vedotin in Platinum-Resistant," ASCO American Society of Clinical Oncology—55th Annual Meeting, Poster 421A, 1 page.
Mahdi, H. et al. (May 20, 2019). "Phase 2 Trial of Tisotumab Vedotin in Platinum-Resistant Ovarian Cancer (innovaTV 208)," Journal of Clinical Oncology 37(15 suppl.):Abstract TPS5602, 4 pages. Abstract Only.
Mandal, S.K. et al. (2006). "Cellular Localization and Trafficking of Tissue Factor," Blood 107:4746-4753.
Marquina, G. et al. (2018, e-pub. Apr. 2, 2018). "Targeted Agents in Cervical Cancer: Beyond Bevacizumab." Current Oncology Reports 20(5):1-10.
McDermott, D.F. et al. (Jul. 21, 2013). "PD-1 as a Potential Target in Cancer Therapy," Cancer Medicine 2(5):662-673.
McDonagh, C.F. et al. (2006, e-pub. Apr. 27, 2006). "Engineered Antibody-Drug Conjugates With Defined Sites and Stoichiometries of Drug Attachment," Prot. Engr. Design & Selection 19(7):299-307.
McLachlan, J. et al. (Mar. 2017, e-pub. Nov. 9, 2016). "The Impact of Systemic Therapy Beyond First-line Treatment for Advanced Cervical Cancer," Clin. Oncol. (R. Coll. Radiol.) 29(3):153-160.
Miller, D.S. et al. (Jul. 2008, e-pub. May 5, 20008). "Evaluation of Pemetrexed (Alimta, LY231514) as Second Line Chemotherapy in Persistent or Recurrent Carcinoma of the Cervix: A Phase II Study of the Gynecologic Oncology Group," Gynecol. Oncol. 110(1):65-70.
Milsom, C.C. et al. (2008). "Tissue Factor Regulation by Epidermal Growth Factor Receptor and Epithelial-to-Mesenchymal Transitions: Effect on Tumor Initiation and Angiogenesis," Cancer Res. 68(24):10068-10076.
Monk, B.J. et al. (2021). "Tisotumab Vedotin (TV) + Bevacizumab or Pembrolizumab or Carboplatin in Recurrent/Metastatic Cervical Cancer (r/mCC): Phase 1b/2 ENGOT-Cx8/GOG-3024/innovaTV 205 Study Dose-Escalation Results," International Gynecologic Cancer Society, 12 pages.
Monk, B.J. et al. (2021). "Tisotumab Vedotin (TV) + Bevacizumab or Pembrolizumab or Carboplatin in Recurrent/Metastatic Cervical Cancer (r/mCC): Phase 1b/2 ENGOT-Cx8/GOG-3024/innovaTV 205 Study Dose-Escalation Results," International Gynecologic Cancer Society, 4 pages.
Morris, G.E. (1996), "Epitope Mapping Protocols," Methods in Molecular Biology 66:1-12.
Morrissey, J.H. et al. (1988). "Monoclonal Antibody Analysis of Purified and Cell-associated Tissue Factor," Thrombosis Research 52:247-261.
Muggia, F.M. et al. (Feb. 2004). "Evaluation of Vinorelbine in Persistent or Recurrent Squamous Cell Carcinoma of the Cervix: A Gynecologic Oncology Group Study," Gynecol. Oncol. 92(2):639-643.
Myers, E.W. et al. (Mar. 1988). Optimal Alignments in Liner Space, Cabios 4(1):11-17.
Mylotarg®. (Aug. 2017). "Mylotarg® (gemtuzumab ozgamicin for Injection). For Intravenous Use Only," Wyeth Pharmaceuticals Inc, 20 pages.
Nagayama, A.K. et al. (Dec. 2017). "Antibody-Drug Conjugates for the Treatment of Solid Tumors: Clinical Experience and Latest Developments," Targeted Oncology 12(6):719-739.
Naing, A. et al. (May 20, 2016), "Abstract 3060: A First-In-Human Phase I Study of the Anti-PD-1 Antibody PDR001 in Patients With Advanced Solid Tumors," Journal of Clinical Oncology 34(15 suppl):3060, 2 pages.
Naing, A. et al. (Oct. 1, 2016). Annals of Oncology 27(suppl 6):1072, 1 page.
NCI's Surveillance, Epidemiology, and End Results Program (SEER) publication SEER Cancer Statistic's Review 1973-1997, 2 pages.
Needleman, S. B. et al. (1970). "A General Method Applicable to the Search for Similarities in the Amino Acid sequence of Two Proteins," J. Mol. Biol. 48:443-453.

(56) References Cited

OTHER PUBLICATIONS

Ngo, C.V. et al. (2007). "CNTO 859, A Humanized Anti-Tissue Factor Monoclonal Antibody, is a Potent Inhibitor of Breast Cancer Metastasis and Tumor Growth in Xenograft Models," Int. J. Cancer 120:1261-1267.
Nooij, R.P. et al. (2018). "Functional MRI for Treatment Evaluation in Patients with Head and Neck Squamous Cell Carcinoma: A Review of the Literature from a Radiologist Perspective," Curr. Radiol. Rep. 6(1):2, 15 pages.
Nyen, T.V. et al. (2018). "Modeling Endometrial Cancer: Past, Present, and Future," Int. J. Mol. Sci. 19(8):2348, 18 pages.
Oflazoglu, E. et al. (2008, e-pub. May 8, 2008). "Combination of the Anti-CD30-Auristatin-E Antibody-Drug Conjugate (SGN-35) With Chemotherapy Improves Antitumour Activity in Hodgkin Lymphoma," BJH 142:69-73.
Okeley, N.M. et al. (2006). "Specific Tumor Targeting and Potent Bystander Killing With SG-35, an Anti-CD30 Antibody Drug Conjugate," Blood, Abstract 231, 1 page.
Park, I.-H. et al. (2018). "Surveillance or Resection After Chemoradiation in Esophageal Cancer," Ann. Transl. Med. 6(4):82, 7 pages.
Parren, P. (2012). "Development of an Auristatin-Conjugated Therapeutic Antibody Against Tissue Factor for the Treatment of Solid Tumors," 3rd Annual World ADC Series, 29 pages.
Parren, P. (2013). "Pre-Clinical Development of a Therapeutic Antibody Drug Conjugate Targeting Tissue Factor," World ADC, San Francisco, CA, 34 pages.
Parren, P. (2015). "Companion Diagnostics (CDx) in Antibody-Drug Conjugate Development," CTMM-TI Pharma Launch Event, abstract, 1 page.
Parren, P. (2016). "Developing Antibody Drug Conjugates for the Treatment of Solid Cancers," PEGS Shanghai, China, 32 pages.
Parren, P. (Apr. 6, 2015). "Current and Future Trends in Antibody Therapeutics," PEGS EU, abstract 1 page.
Parren, P. (Nov. 28, 2012). "Building a Novel Portfolio of ADCs," 8th Annual European Antibody Congress, 31 pages.
Parren, P. (Oct. 2014). "Progressing ADCs for the Treatment of Solid Cancers," World ADC, 28 pages.
Paul, W.E. (1993). Fundamental Immunology, 3d ed. Raven Press. p. 242.
Paul, W.E. ed. (1989). Fundamental Immunology: Second Edition, Raven Press, New York, pp. 332-337.
Philips, G. K. et al. (2014, e-pub. Oct. 16, 2014). "Therapeutic Uses of Anti-PD-1 and Anti-PD-L1 Antibodies," International Immunology 27(1):39-46.
Phillips, G.D.L. et al. (Nov. 15, 2008). "Targeting HER2-Positive Breast Cancer with Trastuzumab-DM1, an Antibody-Cytotoxic Drug Conjugate," Cancer Res 68:(22):9280-9290.
Pinter-Brown, L.C. (2008, e-pub. Nov. 3, 2008). "SGN-30: A Basis for the Effective Treatment of CD30 Positive Hematopoietic Malignancies," Expert Opinion on Investigational Drugs 17(12):1883-1887.
Polson, A.G. et al. (2010). "Anti-CD22-MCC-DM1: An Antibody-Drug Conjugate With a Stable Linker for the Treatment of Non-Hodgkin's Lymphoma," Leukemia 24:1566-1573.
Portolano, S. et al. (Feb. 1, 1993). "Lack of Promiscuity in Autoantigen-Specific H and L Chain Combinations as Revealed by Human H and L Chain "Roulete"," J. Immunol. 150(3):880-887.
Presta, L. et al. (2001). "Generation of a Humanized, High Affinity Anti-Tissue Factor Antibody for Use as a Novel Antithrombotic Therapeutic," Thromb. Haemost. 85:379-389.
Presta, L.G. et al. (Oct. 15, 1997). "Humanization of an Anti-Vascular Endothelial Growth Factor Monoclonal Antibody for the Therapy of Solid Tumors and Other Disorders," Cancer Res. 57:4593-4599.
Pujade-Lauraine, E. et al. (2011). "Updated of Randomized Trials in Recurrent Disease," J. Ann. Oncol. 22 Suppl. viii 61-viii 64, 4 pages.
Pujade-Lauraine, E. et al. May 1, 2014, e-pub. Mar. 17, 2014). "Bevacizumab Combined With Chemotherapy for Platinum-Resistant Recurrent Ovarian Cancer: The Aurelia Open-Label Randomized Phase III Trial," J. Clin. Oncol. 32(13):1302-1308.
Revets, H. et al , (Jan. 2005). "Nanobodies as Noveal Agents for Cancer Therapy." Expert Opin Biol Ther. 5(1) :111-124.
Rice, P. et al. (Jun. 1, 2000). "EMBOSS: The European Molecular Biology Open Software Suite," Trends Genet. 16(6):276-277.
Roberts, J.T. et al. (May 2006). "Long-Term Survival Results of a Randomized Trial Comparing Gemcitabine/Cisplatin and Methotrexate/Vinblastine/doxorubicin/Cisplatin in Patients With Locally Advanced and Metastatic Bladder Cancer," Annals of Oncology 17(Supplement 5):v118-v122, with Retraction vol. 22, issue 11, p. 2536, (Nov. 1, 2011), total 8 pages.
Rose, P.G. et al. (Aug. 2006, e-pub. Feb. 14, 2006). "Evaluation of Pegylated Liposomal Doxorubicin (Doxil) as Second-Line Chemotherapy of Squamous Cell Carcinoma of the Cervix: A Phase II Study of the Gynecologic Oncology Group," Gynecol. Oncol. 102(2):210-213.
Rowland, A.J. et al. (1993). "Preclinical Investigation of the Antitumour Effects of Anti-CD19-idarubicin Immunoconjugates," Cancer Immunology Immunotherapy 37(3):195-202.
Roy, M.L. et al. (1991). "The Effects of Formulation and Moisture on the Stability of a Freeze-Dried Monoclonal Antibody—Vinca Conjugate: A Test of the WLF Glass Transition Theory," Developments in Biological Standardization 74:323-340.
Rudikoff, S. et al. (Mar. 1982). "Single Amino Acid Substitution Altering Antigen-Binding Specificity," Proc. Natl. Acad. Sci. USA 79:1979-1983.
Rustin, G.J. et al. (Feb. 2011). "Definitions for Response and Progression in Ovarian Cancer Clinical Trials Incorporating recist 1.1 and CA 125 Agreed by the Gynecological Cancer Intergroup (GCIG)," Int. J. Gynecol. Cancer 21(2):419-423.
Ryan, M.C. et al. (2010). "Targeting Pancreatic and Ovarian Carcinomas Using the Auristatin-Based Anti-CD70 Antibody-Drug Conjugate SGN-75," British Journal of Cancer 103:676-684.
Sabbatini, P.J. et al. (2007, e-pub. Jul. 18, 2007). "Pilot Study of a Heptavalent Vaccine-Keyhole Limpet Hemocyanin Conjugate Plu QS21 in Patients With Epithelial Ovarian, Fallopian Tube, or Peritoneal Cancer," Clinical Cancer Research 13:4170-4177.
Sanderson, R.J. et al. (Jan. 15, 2005). "In vivo Drug-Linker Stability of an Anti-CD30 Dipeptide-Linked Auristatin Immunoconjugate," Clin. Cancer Res. 11:843-852.
Satijn, D. (2013). "Development of an Auristatin-Conjugated Therapeutic Antibody Against Tissue Factor for the Treatment of Solid Tumors," Empowered Antibodies, ADCs-Barcelona, 30 pages.
Satijn, D. (Jun. 17-18, 2015). "Targeting Solid Cancers Using Antibody-Drug Conjugate Against the Novel ADC Target Tissue Factor, a Preclinical and FIH Study," Empowered Antibodies Congress, Barcelona, 38 pages.
Schellens, J.H.M. et al. (May 20, 2017). "Pembrolixumab for Previously Treated Advanced Cervical Squamous Cell Cancer: Preliminary Results From the Phase 2 Keynote-158 Study," J Clin Oncol. 35(Suppl.):Abstract 5514, 4 pages.
Scher, H.I. et al. (Mar. 1, 2008). "Design and End Points of Clinical Trials for Patients With Progressive Prostate Cancer and Castrate Levels of Testosterone: Recommendations of the Prostate Cancer Clinical Trials Working Group," J. Clin. Oncol. 26(7):1148-1159.
Schilder, R.J. et al. (Jan. 2005). "Evaluation of Gemcitabine in Previously Treated Patients With Non-Squamous Cell Carcinoma of the Cervix: A Phase II Study of the Gynecologic Oncology Group," Gynecol. Oncol. 96(1):103-107.
SeattleGenetics. (2008). "SGN-35: Antibody-Drug Conjugate," Seattle Genetics 1 page.
SeattleGenetics. (2009). "Seattle Genetics Reports Positive Data From Phase I Weekly-Dosing Clinical Trial of Brentuximab Vedotin (SGN-35) in Lymphoma," SeatttleGenetics New Release 2 pages.
SEER Cancer Statistics Review, (1975-2011), 5 pgs.
Selva, C. et al. (Feb. 2013) et al. "Trehalose Preserves the Integrity of Lyophilized Phycoerythrin-Antihuman CD8 Antibody Conjugates and Enhances Their Thermal Stability in Flow Cytometric Assays," Journal of Pharmaceutical Sciences 102(2):649-659.

(56) References Cited

OTHER PUBLICATIONS

Senter, P. et al. (2004). "Immunoconjugates Comprised of Drugs With Impaired Cellular Permeability: A New Approach to Targeted Therapy," Proc. Amer. Assoc. Cancer Res. 45:Abstract No. 623, 2 pages.
Serio, R.N (2012). "Toward an Integrative Analysis of the Tumor Microenvironment in Ovarian Epithelial Carchinoma," Cancer Microenvironment 5:173-183.
Sheriff, S. et al. (Sep. 1996). "Redefining the Minimal Antigen-Binding Fragment," Nature Struct. Biol. 3(9):733-736.
Singh, S.R. et al. (Jun. 2012, e-pub. Feb. 24, 2012). "Effect of Polysorbate 80 Quality on Photostability of a Monocional Antibody," AAPS PharmSciTech 13(2):422-430.
Sjöblom, T. et al. (Oct. 13, 2006). "The Consensus Coding Sequences of Human Breast and Colorectal Cancers," Science 314:268-274.
Slaughter, K. et al. (Aug. 2016, e-pub. May 25, 2016). "Primary and Acquired Platinum-Resistance Among Women With High Grade Serous Ovarian Cancer," Gyriecol. Oncol. 142(2):225-230.
Stephan, J.P. et al. (Mar. 2011). "Challenges in Developing Bioanalytical Assays for Characterization of Antibody-Drug Conjugates," Bioanalysis 3(6):677-700.
Sun, M.M.C. et al. (Sep./Oct. 2005). "Reduction-Alkylation Strategies for the Modification of Specific Monoclonal Antibody Disulfides," Bioconjug. Chem. 16(5):1282-1290, 22 pages.
Topalian, S.L. et al. (Apr. 1, 2014, e-pub. Mar. 3, 2014). "Survival, Durable Tumor Remission, and Long-Term Safety in Patients With Advanced Melanoma Receiving Nivolumab," J. Clin. Oncol. 32(10):1020-1030.
Topalian, S.L. et al. (Apr. 2012, e-pub. Jan. 9, 2012). "Targeting the PD-1/B7-H1 (PD-L1) Pathway to Activate Anti-Tumor Immunity," Curr. Opin Immunol. 24(2):207-212, 11 pages.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Torfs, S. et al. (Jun. 2012, e-pub. Feb. 7, 2012). "Evaluation of Paclitaxel/Carboplatin in a Dose Dense or Weekly Regimen in 66 Patients With Recurrent or Primary Metastatic Cervical Cancer," Lur. J. Cancer 48(9):1332-1340.
Traynor, K. (Jun. 22, 2010). "Pharmacy News. Gemtuzumab Withdrawn From U.S. Market," ASHP 2 pages.
U.S. Appl. No. 63/045,448, filed Jun. 29, 2020, Rangwala et al. (Copy not submitted herewith pursuant to the waiver of 37 C.F.R. § 1.98(a)(2)(III) issued by the Office on Sep. 21, 2004).
U.S. Appl. No. 63/094,571, filed Oct. 21, 2020, Rangwala et al. (Copy not submitted herewith pursuant to the waiver of 37 C.F.R. § 1.98(a)(2)(III) issued by the Office on Sep. 21, 2004).
Van Bueren, J.L. (Mar. 18, 2015). "Alignment of Antibody Drug Conjugate—CDx Co-Development," World CDx Meeting, Berlin; Germany, 24 pages.
Van De Winkel, J. (Jan. 23, 2012). "Pre-clinical Pipeline and Technology: HuMax-TF-ADC Aimed at the Clinic" Post ASH, 11 pages.
Vergote, I. et al. (2020). "Phase Ib/II Trial of Tisotumab Vedotin (TV) Bevacizumab (BEV), Pembrolizumab (PEM), or Carboplatin (CBP) in Recurrent or Metastatic Cervical Cancer (innovaTV) 205/ENGOT-cx8/GOG-3024)," Journal of Clinical Oncology 38(15):TPS6095-TPS6095, Abstract 266, 1 page.
Vergote, I. et al. (2017). "A Phase IIa Study of Tisotumab Vedotin (HuMax®-TF-ADC) in Patients With Relapsed, Recurrent and/or Metastatic Cervical Cancer," ESMO, Madrid, 16 pages.
Vergote, I. et al. (2019). "Phase 1/2 Trial of Tisotumab Vedotin Plus Bevacizumab, Pembrolizumab, or Carboplatin in Recurrent or Metastatic Cervical Cancer (innovaTV 205)-TIP," ESMO (2019) European Society for Medical Oncology 44th Congress—Poster 205 ESMO, 1 page.
Vergote, I. et al. (2020). "Phase Ib/II Trial of Tisotumab Vedotin (TV) ± Bevacizumab (BEV), Pembrolizumab (PEM), or Carboplatin (CBP) in Recurrent or Metastatic Cervical Cancer (innovaTV 205/ENGOT-cx8/GOG-3024) TIP," ASCO American Society of Clinical Oncology—56th Annual Meeting, 1 page.
Vergote, I. et al. (2021). "Tisotumab Vedotin + Carboplatin in First-Line or + Pembrolizumab in Previously Treated Recurrent/ Metastatic Cervical Cancer: Interim Results of ENGOT-Cx8/GOG-3024/innovaTV 205," ESMO, 9 pages.
Vergote, I. et al. (2021). "Tisotumab Vedotin vs Investigator's Choice Chemotherapy in Second- or Third-Line Recurrent or Metastatic Cervical Cancer (innovaTV 301/ENGOT CX12/GOG 3057)," American Society of Clinical Onocology, Abstract, 1 page.
Vergote, I. et al. (2021). "Tisotumab Vedotin vs Investigator's Choice Chemotherapy in Second- or Third-Line Recurrent or Metastatic Cervical Cancer (innovaTV 301/ENGOT CX12/GOG 3057)," American Society of Clinical Onocology, Abstract, 2 page.
Vergote, I. et al. (Jul. 26, 2021). "Tisotumab Vedotin + Carboplatin in First-Line or + Pembrolizumab in Previously Treated Recurrent/ Metastatic Cervical Cancer: Interim Results of ENGOT-Cx8/GOG-3024/innovaTV 205," ESMO, 4 pages.
Vergote, I.B. (Oct. 1, 2019). "Phase I/II Trial of Tisotumab Vedotin Plus Bevacixumab, Pembrolizumab, or Carboplatin in Recurrent or Metastatic Cervical Cancer (innovaTV 205/ENGOT-cx8)—ScienceDirect," Annals of Oncology 30(5):v433-v434.
Verma, S. et al. (2012). "Trastuzumab Emtansine for HER2-Positive Advanced Breast Cancer," The New England Journal of Medicine 367(19):1783-1791.
Versteeg, H.H. et al. (2008). "Inhibition of Tissue Factor Signaling Suppresses Tumor Growth," Blood 111:190-199.
Vine, A.K. (2009). "Recent Advances in Haemostasis and Thrombosis," Retina 29:1-7.
Vlachostergios, P.J. et al. (2018). "Antibody-Drug Conjugates in Bladder Cancer," Bladder Cancer 4(3):247-259.
Vázquez-Rey, M. et al. (2011, e-pub. Apr. 7, 2011). "Aggregates in Monoclonal Antibody Manufacturing Process," Biotech, Bioeng. 108(7):1494-1508.
Wahl, A.F. et al. (Jul. 1, 2002). "The Anti-CD30 Monoclonal Antibody SGN-30 Promotes Growth Arrest and DNA Fragmentation in Vitro and Affects Antitumor Activity in Models of Hodgkin's Disease," Cancer Research 62:3736-3742.
Wakankar, A. et al. (Mar.-Apr. 2011, e-pub. Mar. 1, 2011). "Analytical Methods for Physicochemical Characterization of Antibody Drug Conjugates," MAbs 3(2):161-172.
Wakankar, A.A. et al. (Sep. 15, 2010). "Physicochemical Stability of the Antibody-5 Drug Conjugate Trastuzumab-DM1: Changes due to Modification and Conjugation Processes," Bioconjugate Chemistry 21(9):1588-1595.
Wang, B. et al. (2005). "Radiotherapy of Human Xenograft NSCLC Tumors in Nude Mice with a 90Y-Labeled Anti-Tissue Factor Antibody," Cancer Biotherapy & Radiopharmaceuticals 20(3):300-309.
Ward, E.S. et al. (Oct. 12, 1989). "Binding Activities of a Repertoire of Single Immunoglobulin Variable Domains Secreted From *Escherichia coli*," Nature 341:544-554.
Wolfgang, C.L. et al. (Sep. 2013). "Recent Progress in Pancreatic Cancer," CA Cancer J. Clin. 63(5)318-348, 62 pages.
Written Opinion mailed on Mar. 9, 2010, for PCT Application No. PCT/US10/20504, filed on Jan. 8, 2010, 5 pages.
Xu. J.L. et al. (Jul. 2000). "Diversity in the CDR3 Region of VH Is Sufficient for Most Antibody Specificities," Immunity 13:37-45.
Yonemori, K. et al. (2021). "Tisotumab Vedotin in Japanese Patients With Recurrent or Metastatic Cervical Cancer: Results From the Phase 1/2 innovaTV 206 Study," Japan Society of Gynecologic Oncology, 3 pages.
Yonemori, K. et al. (2021). "Tisotumab Vedotin in Japanese Patients With Recurrent or Metastatic Cervical Cancer: Results From the Phase 1/2 innovaTV 206 Study," Japan Society of Gynecologic Oncology, 7 pages.
Younes, A. et al. (2007). "A Novel Antibody-Drug Conjugate, SGN-35 (AntiCD30-Auristatin), Induces Objective Responses in Patients With Relapsed or Refractory Hodgkin Lymphoma Preliminary Results of a Phase I Tolerability Study," 7the International Symposium on Hodgkin Lymphoma, Cologne, Nov. 4-7, 2007, 1 page.
Younes, A. et al. (2008). "Multiple Complete Responses in a Phase 1 Does-Escalation Study of the Antibody-Drug Conjugate SGN-35

(56) References Cited

OTHER PUBLICATIONS in Patients with Relapsed or Refractory CD30-Postivie Lymphomas," Blood ASH Annual Meeting Abstract 1006, 2 pages.
Younes, A. et al. (2008). "Objective Responses in a Phase I Dose-Escalation Study of SGN-35, a Novel Antibody-Drug Conjugate (ADC) Targeting CD30, in Patients With Relapsed or Refractory Hodgkin Lymphoma," Abstract No. 8526, 44th ASCO Annual Meeting, May 30-Jun. 3, 2008, 1 page.
Younes, A. et al. (Dec. 2013, e-pub. Nov. 15, 2013). "Brentuximab Vedotin Combines With ABDV or AVD for Patients With Newly Diagnosed Hodgkin's Lymphoma: A Phase 1, Open-Label. Does-Escalation Study," Lancet Oncol. 14:1348-1356.
Younes, A. et al. (Nov. 4, 2010). "Brentuximab Vedotin (SGN-35) for Relapsed CD30-Positive Lymphomas," New England Journal of Medicine 363(19):1812-1821.
Youssef, S. et al. (Jul. 2017). "Abstract 2667: In vitro Properties and Pre-Clinical Activity of PF-06801591, a High-Affinity Engineered Anti-Human PD-1," Cancer Res 77(13 Suppl):Abstract 2667, 4 pages.
Yu, J.L. et al. (2005). "Oncogenic events Regulate Tissue Factor Expression in Colorectal Cancer Cells: Implications for Tumor Progression and Angiogenesis," Blood 105:1734-1741.
Yu, S.S. et al. (Jun. 2017). "Immunotherapy in Uropthelial Cancer, Part 1: T-Cell Checkpoint Inhibition in Advanced or Metastatic Disease," Clinical Advances in Haematology & Oncology 15(6):466-477.
Zhang, Z. (Dec. 31, 2007). "Pharmacy", Higher Education Press, A pp. 173-174, With English Translation, 7 pages.
Zhao, H. et al. (Sep. 2002) "Preparation and Identification of Monoclonal Antibodies Against Human Recombinant Soluble Tissue Factor", Chinese Journal of Hematology 23(9):489-491. (Google translation).
Burotto, M. et al. (2015). "Phase II Clinical Trial of Ixabepilone in Metastatic Cervical Carcinoma," Oncologist 20:725-726.
Candelaria, M. et al. (Dec. 2009). "Lack in Efficacy for Imatinib Mesylate as Second-Line Treatment of Recurrent or Metastatic Cervical Cancer Expressing Platelet-Derived Growth Factor Receptor Alpha," Int. J. Gynecol. Cancer 19(9):1632-1637. Abstract Submitted.
Chen, J. et al. (Jun. 1993). "Immunoglobulin Gene Rearrangement in B Cell Deficient Mice Generated by Targeted Deletion of the JH Locus," International Immunology. 5(6):647-656. Abstract Submitted.
Chenard-Poirier, M. et al. (Sep. 2017). "D36A Phase I/II Safety Study of Tisotumab Vedotin (HuMax®-TF-ADC) in Patients With Solid Tumours," ESMO 36A—Abstract 1184P—28(Supp.5):420.
Coronel, J. et al. (2009, e-pub. Oct. 28, 2008). "Weekly Topotecan as Second- or Third-Line Treatment in Patients With Recurrent or Metastatic Cervical Cancer," Med. Oncol, 26(2):210-214. Abstract Submitted.
Fiorica, J.V. et al. (Nov. 2009, e-pub. Sep. 2, 2009). "A Phase II Evaluation of Weekly Topotecan as a Single Agent Second Line Therapy in Persistent or Recurrent Carcinoma of the Cervix: A Gynecologic Oncology Group Study," Gynecol. Oncol. 115(2):285-289. Abstract Submitted.
Garcia, A.A. et al. (Aug. 2007). "Phase II Clinical Trial of Docetaxel in Refractory Squamous Cell Carcinoma of the Cervix: A Gynecologic Oncology Group Study," Am. J. Clin. Oncol. 30(4):428-431. Abstract Submitted.
Genmab Announces Preliminary Cervical Cancer Data from Tisotumab Vedotin Phase I/II Study. Company Announcement, Copenhagen, Denmark; Jun. 16, 2017—Genmab A/S, 2 pages.
Hillemanns, P. et al. (2016, e-pub. Aug. 22, 2016). "Epidemiology and Early Detection of Cervical Cancer," Oncol. Res. Treat. 39(9):501-506. Abstract Submitted.

Hobbs, J.E. et al. (2007). "Alternatively Spliced Human Tissue Factor Promotes Tumor Growth and Angiogenesis in a Pancreatic Cancer Tumor Model," Thrombosis Res. 120(Suppl. 2):S13-S21. Abstract Submitted.
Homesley, H.D. et al. (Feb. 2008, e-pub. Feb. 29, 2008). "A Phase II Trial of Weekly 1-Hour Paclitaxel as Second-Line Therapy for Endometrial and Cervical Cancer," Int. J. Clin. Oncol. 13(1):62-65. Abstract Submitted.
McLachlan, J. et al. (Mar. 2017, e-pub. Nov. 9, 2016). "The Impact of Systemic Therapy Beyond First-line Treatment for Advanced Cervical Cancer," Clin. Oncol. (R. Coll. Radiol.) 29(3):153-160. Abstract Submitted.
Miller, D.S. et al. (Jul. 2008, e-pub. May 5, 20008). "Evaluation of Pemetrexed (Alimta, LY231514) as Second Line Chemotherapy in Persistent or Recurrent Carcinoma of the Cervix: A Phase II Study of the Gynecologic Oncology Group," Gynecol. Oncol. 110(1):65-70. Abstract Submitted.
Monk, B.J. et al. (Mar. 1, 2009, e-pub. Jan. 12, 2009). "Phase II Trial of Bevacizumab in the Treatment of Persistent or Recurrent Squamous Cell Carcinoma of the Cervix: A Gynecologic Oncology Group Study," J. Clin. Oncol. 27(7):1069-1074.
Muggia, F.M. et al. (Feb. 2004). "Evaluation of Vinorelbine in Persistent or Recurrent Squamous Cell Carcinoma of the Cervix: A Gynecologic Oncology Group Study," Gynecol. Oncol. 92(2):639-643. Abstract Submitted.
Rose, P.G. et al. (Augst 2006, e-pub. Feb. 14, 2006). "Evaluation of Pegylated Liposomal Doxorubicin (Doxil) as Second-Line Chemotherapy of Squamous Cell Carcinoma of the Cervix: A Phase II Study of the Gynecologic Oncology Group," Gynecol, Oncol. 102(2):210-213. Abstract Submitted.
Russell, S.J. et al. (Mar. 11, 1993). "Retroviral Vectors Displaying Functional Antibody Fragments," Nucl. Acids Research 21(5):1081-1085.
Santin, A.D. et al. (Sep. 2011). "Phase II Trial of Cetuximab in the Treatment of Persistent or Recurrent Squamous or Non-Squamous Cell Carcinoma of the Cervix: A Gynecologic Oncology Group Study," Gynecol. Oncol. 122(3):495-500, 17 pages.
Schilder, R.J. et al. (Jan. 2005). "Evaluation of Gemcitabine in Previously Treated Patients With Non-Squamous Cell Carcinoma of the Cervix: A Phase II Study of the Gynecologic Oncology Group," Gynecol. Oncol. 96(1):103-107. Abstract Submitted.
Tewari, K.S. et al. (Feb. 20, 2014). "Improved Survival With Bevacizumab in Advanced Cervical Cancer," N Engl J Med. 370(8):734-743, 14 pages.
Torfs, S. et al. (Jun. 2012, e-pub. Feb. 7, 2012). "Evaluation of Paclitaxel/Carboplatin in a Dose Dense or Weekly Regimen in 66 Patients With Recurrent or Primary Metastatic Cervical Cancer," Eur. J. Cancer 48(9):1332-1340. Abstract Submitted.
U.S. Appl. No. 16/880,241, filed May 21, 2002, for Verploegen et al. (Copy not submitted herewith pursuant to the waiver of 37 C.F.R. § 1.98(a)(2)(III) issued by the Office on Sep. 21, 2004).
Cohen, J.G. et al. (2017, e-pub. May 10, 2017). "Evaluation of Venous Thrombosis and Tissue Factor in Epithelial Ovarian Cancer," Gynecologic Oncology 146:146-152.
De Bono, J.S. (Mar. 2019, e-pub. Feb. 7, 2019). "Supplementary Appendix," The Lancet Oncology pp. 1-142.
Kobayashi-Kato, M. et al. (2018, e-pub. Apr. 13, 2019). "Platinum-Free Interval Affects Efficacy of Following Treatment for Platinum-Refractory or -Resistant Ovarian Cancer," Cancer Chemotherapy and Pharmacology 84:33-39.
Perkins, V. et al. (Jan. 2020). "Incorporation of Whole Pelvic Radiation Into Treatment of Stage IVB Cervical Cancer: A Novel Treatment Strategy," Gynecol Oncol. 156(1):100-106, 15 pages.
Prat, J. (2014). "Staging Classification for Cancer of the Ovary, Fallopian Tube, and Peritoneum," International Journal of Gynecology and Obstetrics 124:1-5.
SeattleGenetics (Sep. 8, 2017). "Seatle Genetics Highlights Promising Data with Tisotumab Vedotin in Cervical Cancer at ESMO 2017 Congress," BusinessWire, 3 pages.

* cited by examiner

METHODS OF TREATING CANCER WITH A COMBINATION OF A PLATINUM-BASED AGENT AND AN ANTI-TISSUE FACTOR ANTIBODY-DRUG CONJUGATE

CROSS-REFERENCE TO RELATED APPLICATIONS

This application is a national stage application under 35 U.S.C. § 371 of International Application No. PCT/US2019/023218, filed internationally on Mar. 20, 2019, which claims priority to U.S. Provisional Application No. 62/646,256 filed Mar. 21, 2018 and U.S. provisional Application No. 62/753,730 filed on Oct. 31, 2018 the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 761682000600SEQLIST.TXT, date recorded: Sep. 10, 2020, size: 6 KB).

TECHNICAL FIELD

The present invention relates to methods of treating cancer, such as bladder cancer and cervical cancer, with a combination of a platinum-based agent and an anti-Tissue Factor (anti-TF) antibody-drug conjugate.

BACKGROUND

Tissue factor (TF), also called thromboplastin, factor III or CD142 is a protein present in subendothelial tissue, platelets, and leukocytes necessary for the initiation of thrombin formation from the zymogen prothrombin. Thrombin formation ultimately leads to the coagulation of blood. TF enables cells to initiate the blood coagulation cascade, and it functions as the high-affinity receptor for the coagulation factor VIIa (FVIIa), a serine protease. The resulting complex provides a catalytic event that is responsible for initiation of the coagulation protease cascades by specific limited proteolysis. Unlike the other cofactors of these protease cascades, which circulate as nonfunctional precursors, TF is a potent initiator that is fully functional when expressed on cell surfaces.

TF is the cell surface receptor for the serine protease factor VIIa (FVIIa). Binding of FVIIa to TF starts signaling processes inside the cell, said signaling function playing a role in angiogenesis. Whereas angiogenesis is a normal process in growth and development, as well as in wound healing, it is also a fundamental step in the transition of tumors from a dormant state to a malignant state. When cancer cells gain the ability to produce proteins that participate in angiogenesis (i.e., angiogenic growth factors), these proteins are released by the tumor into nearby tissues, thereby stimulating new blood vessels to sprout from existing healthy blood vessels toward and into the tumor. Once new blood vessels enter the tumor, the tumor can rapidly expand its size and invade local tissue and organs. Through the new blood vessels, cancer cells may further escape into the circulation and lodge in other organs to form new tumors, also known as metastasis.

TF expression is observed in many types of cancer, including cervical cancer, and is associated with more aggressive disease. Furthermore, human TF also exists in a soluble alternatively-spliced form, asHTF. It has been found that asHTF promotes tumor growth (Hobbs et al., 2007, Thrombosis Res. 120(2): S13-S21).

Platinum-based agents are alkylating agents which bind covalently to DNA and cross-link DNA strands, resulting in inhibition of DNA synthesis and function as well as inhibition of transcription. Single agent carboplatin has been an option for first-line recurrent or metastatic disease for several decades. In a phase 2 trial of single agent carboplatin for recurrent or metastatic squamous carcinoma of the uterine cervix, the overall response rate was 15% (6/41) with major toxic effects including nausea and vomiting (48%), anemia (47%), leukopenia (38%), and thrombocytopenia (22%) (Weiss et al., 1990, Gynecol. Oncol. 39, 332-336). The addition of paclitaxel was assessed in the phase 3 trial of cisplatin with or without paclitaxel, which demonstrated significant improvement in PFS in subjects with stage IVB, recurrent, or persistent squamous cell carcinoma of the cervix; furthermore response rates were substantially higher with the combination regimen. Objective responses (OR) occurred in 19% (6% complete plus 13% partial) of subjects receiving cisplatin versus 36% (15% complete plus 21% partial) receiving carboplatin+paclitaxel (P=0.002). The median PFS was 2.8 and 4.8 months, respectively, for cisplatin versus carboplatin+paclitaxel (P<0.001). There was no difference in median survival (8.8 months vs 9.7 months) at the time of data cutoff (Moore et al, 2004). Despite the efficacy gains observed with cisplatin, the toxicity profile for this agent is worse than carboplatin. Interchangeability of these 2 agents has been assessed in multiple trials including the phase 3 trial, JCOG050. This trial demonstrated similar efficacy between the combination of cisplatin and paclitaxel as compared to carboplatin+paclitaxel (Median OS 18.3 months vs 17.5 months, respectively; HR 0.994 (90% CI, 0.79 to 1.25; P=0.032), and is considered a standard of care option for patients with stage IVB, recurrent or persistent cervical carcinoma (Kitagawa et al., 2015, J. Clin. Oncol. 33, 2129-2135).

Bladder cancer is a life-threatening and progressive disease, which usually begins in the lining of the epithelial lining (i.e., the urothelium) of the urinary bladder. Invasive bladder cancer may spread to lymph nodes, other organs in the pelvis (causing problems with kidney and bowel function), or other organs in the body, such as the liver and lungs. Standard treatments for bladder cancer are surgery, radiation therapy, chemotherapy, and biological therapy. Bladder cancer is the fifth most common cancer diagnosis in the US. Because patients have a high risk of recurrence and progression, bladder cancer is the most expensive cancer to treat on a per patient lifetime basis. Despite its incidence and prevalence, bladder cancer research is woefully underfunded, resulting in little progress in improving the treatment of bladder cancer.

Cervical cancer poses a significant medical problem worldwide with an estimated incidence of more than 500,000 new cases and 250,000 deaths annually. See Tewari et al., 2014, N Engl J Med., 370:734-743. In the Europe Union, approximately 34,000 new cases of cervical cancer and 13,000 deaths occur annually. See Hillemanns et al., 2016, Oncol. Res. Treat. 39:501-506. The main types of cervical cancer are squamous cell carcinoma and adenocarcinoma. Long-lasting infections with human papillomavirus (HPV) type 16 and 18 cause most cases of cervical cancer. The standard for first-line therapy of cervical cancer was a platinum-based therapy plus a taxane-based therapy. Bevacizumab, an anti-VEGF antibody, was approved by the U.S.

Food and Drug Administration for use in combination with chemotherapy for the treatment of cervical cancer, which had improved overall survival in clinical trials. First-line (1 L) treatment for advanced cervical cancer is comprised of bevacizumab combined with paclitaxel plus a platinum (e.g., cisplatin or carboplatin) or paclitaxel plus topotecan. Despite a 48% objective response rate (ORR) and a median overall survival (OS) of approximately 18 months, unfortunately almost all patients relapse after this 1 L treatment. See Tewari et al., 2014, *N Engl J Med.*, 370:734-743. For second-line (2 L) treatment, no approved therapy is available and patients are often treated with single agent modalities including, but not limited to: pemetrexed, topotecan, docetaxel, nab-paclitaxel, vinorelbine and in some cases bevacizumab. A meta-analysis of single agent treatment demonstrates a modest response rate of only 10.9% (i.e., 60 responders out of 552 patients) and median overall survivals (OS) of approximately 7 months. See e.g., Burotto et al., 2015, *Oncologist* 20:725-726; Candelaria et al., 2009, *Int. J. Gynecol. Cancer.* 19:1632-1637; Coronel et al., 2009, *Med. Oncol.* 26:210-214; Fiorica et al., 2009, *Gynecol. Oncol.* 115:285-289; Garcia et. al., 2007, *Am. J Clin. Oncol.* 30-428-431; Goncalves et al., 2008, *Gynecol. Oncol.* 108: 42-46; Homesley et al., 2008, *Int. J Clin. Oncol.* 13:62-65; McLachlan et al., 2017, *Clin. Oncol.* (R. Coll. Radiol.) 29:153-160; Miller et al., 2008, *Gynecol. Oncol.* 110:65-70; Monk et al., 2009, *J Clin. Oncol.* 27:1069-1074; Muggia et al., 2004, *Gynecol. Oncol.* 92:639-643; Rose et al., 2006, *Gynecol. Oncol.* 102:210-213; Santin et al., 2011, *Gynecol. Oncol.* 122:495-500; Schilder et al., 2005, *Gynecol. Oncol.* 96:103-107; and Torfs et al., 2012, *Eur. J Cancer.* 48:1332-1340. The five year relative survival for stage IV cervical cancer is only 15%, demonstrating a high need for improved therapy against cervical cancer.

There remains a need for combination therapies with an acceptable safety profile and high efficacy for the treatment of cancer, in particular for the treatment of bladder cancer and cervical cancer. The present invention meets this need by providing methods of treating cancer, such as bladder cancer and cervical cancer, with a combination of a platinum-based agent and an anti-Tissue Factor (anti-TF) antibody-drug conjugate.

All references cited herein, including patent applications, patent publications, and scientific literature, are herein incorporated by reference in their entirety, as if each individual reference were specifically and individually indicated to be incorporated by reference.

SUMMARY

Provided herein is a method of treating cancer in a subject, the method comprising administering to the subject a platinum-based agent and an antibody-drug conjugate that binds to tissue factor (TF), wherein the antibody-drug conjugate comprises an anti-TF antibody or an antigen-binding fragment thereof conjugated to a monomethyl auristatin or a functional analog thereof or a functional derivative thereof. In some embodiments, the antibody-drug conjugate is administered at a dose ranging from about 0.9 mg/kg to about 2.1 mg/kg. In some embodiments, the antibody-drug conjugate is administered at a dose of about 1.3 mg/kg. In some embodiments, the antibody-drug conjugate is administered at a dose of 1.3 mg/kg. In some embodiments, the antibody-drug conjugate is administered at a dose of about 2.0 mg/kg. In some embodiments, the antibody-drug conjugate is administered at a dose of 2.0 mg/kg. In some of any of the embodiments herein, the antibody-drug conjugate is administered once about every 1 week, once about every 2 weeks, once about every 3 weeks or once about every 4 weeks. In some of any of the embodiments herein, the antibody-drug conjugate is administered once about every 3 weeks. In some of any of the embodiments herein, the antibody-drug conjugate is administered once every 3 weeks. In some of any of the embodiments herein, the platinum-based agent is administered at a dose between about AUC=4 and about AUC=6. In some of any of the embodiments herein, the platinum-based agent is administered a dose of about AUC=5. In some of any of the embodiments herein, the platinum-based agent is administered a dose of AUC=5. In some of any of the embodiments herein, the platinum-based agent is administered once about every 1 week, once about every 2 weeks, once about every 3 weeks or once about every 4 weeks. In some of any of the embodiments herein, the platinum-based agent is administered once about every 3 weeks. In some of any of the embodiments herein, the platinum-based agent is administered once every 3 weeks. In some of any of the embodiments herein, the cancer is bladder cancer. In some of any of the embodiments herein, the cancer is cervical cancer. In some of any of the embodiments herein, the subject is not a candidate for curative therapy. In some of any of the embodiments herein, curative therapy comprises radiotherapy and/or exenterative surgery. In some of any of the embodiments herein, the subject has not received prior systemic therapy for the cervical cancer. In some of any of the embodiments herein, the cervical cancer is an adenocarcinoma, an adenosquamous carcinoma or a squamous cell carcinoma. In some of any of the embodiments herein, the cervical cancer is an advanced stage cervical cancer. In some of any of the embodiments herein, the advanced stage cervical cancer is a stage 3 or stage 4 cervical cancer. In some of any of the embodiments herein, the advanced stage cervical cancer is metastatic cervical cancer. In some of any of the embodiments herein, the cervical cancer is recurrent cervical cancer. In some of any of the embodiments herein, the monomethyl auristatin is monomethyl auristatin E (MMAE). In some of any of the embodiments herein, the anti-TF antibody or antigen-binding fragment thereof of the antibody-drug conjugate is a monoclonal antibody or a monoclonal antigen-binding fragment thereof. In some of any of the embodiments herein, the anti-TF antibody or antigen-binding fragment thereof of the antibody-drug conjugate comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme. In some of any of the embodiments herein, the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8. In some of any of the embodiments herein, the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8. In some of any of the embodiments herein, the anti-TF antibody of the antibody-drug conjugate is tisotumab. In some of any of the embodiments herein, the antibody-drug conjugate further comprises a linker between the anti-TF antibody or antigen-binding fragment thereof and the monomethyl auristatin. In some of any of the embodiments herein, the linker is a cleavable peptide linker. In some of any of the embodiments herein, the cleavable peptide linker has a formula: -MC-vc-PAB-, wherein:
a) MC is:

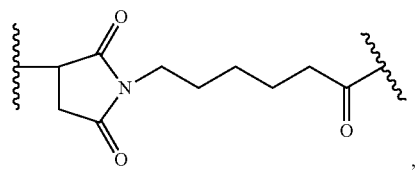 [SMILES: *C(=O)CCCCCN1C(=O)CC(*)C1=O]

, b) vc is the dipeptide valine-citrulline, and
c) PAB is:

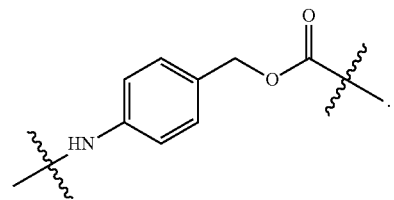 [SMILES: *Nc1ccc(COC(*)=O)cc1]

.

In some of any of the embodiments herein, the linker is attached to sulphydryl residues of the anti-TF antibody obtained by partial reduction or full reduction of the anti-TF antibody or antigen-binding fragment thereof. In some of any of the embodiments herein, the linker is attached to MMAE, wherein the antibody-drug conjugate has the following structure:

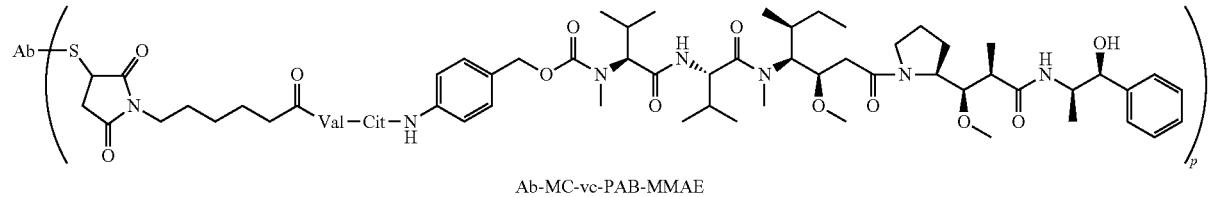

Ab-MC-vc-PAB-MMAE wherein p denotes a number from 1 to 8, S represents a sulphydryl residue of the anti-TF antibody, and Ab designates the anti-TF antibody or antigen-binding fragment thereof. In some of any of the embodiments herein, the average value of p in a population of the antibody-drug conjugates is about 4. In some of any of the embodiments herein, the antibody-drug conjugate is tisotumab vedotin. In some of any of the embodiments herein, the route of administration for the antibody-drug conjugate is intravenous. In some of any of the embodiments herein, the platinum-based agent is selected from the group consisting of carboplatin, cisplatin, oxaliplatin, and nedaplatin. In some of any of the embodiments herein, the platinum-based agent is carboplatin. In some of any of the embodiments herein, the platinum-based agent is cisplatin. In some of any of the embodiments herein, the route of administration for the platinum-based agent is intravenous. In some of any of the embodiments herein, the platinum-based agent and the antibody-drug conjugate are administered sequentially. In some of any of the embodiments herein, the platinum-based agent and the antibody-drug conjugate are administered simultaneously. In some of any of the embodiments herein, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF. In some of any of the embodiments herein, one or more therapeutic effects in the subject is improved after administration of the antibody-drug conjugate and the platinum-based agent relative to a baseline. In some of any of the embodiments herein, the one or more therapeutic effects is selected from the group consisting of: size of a tumor derived from the cervical cancer, objective response rate, duration of response, time to response, progression free survival, and overall survival. In some of any of the embodiments herein, the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent. In some of any of the embodiments herein, the objective response rate is at least about 20%, at least about 25%, at least about 30%, at least about 35%, at least about 40%, at least about 45%, at least about 50%, at least about 60%, at least about 70%, or at least about 80%. In some of any of the embodiments herein, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent. In some of any of the embodiments herein, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent. In some of any of the embodiments herein, the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent. In some of any of the embodiments herein, the subject has one or more adverse events and is further administered an additional therapeutic agent to eliminate or reduce the severity of the one or more adverse events. In some of any of the embodiments herein, the subject is at risk of developing one or more adverse events and is further administered an additional therapeutic agent to prevent or reduce the severity of the one or more adverse events. In some of any of the embodiments herein, the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding. In some of any of the embodiments herein, the one or more adverse events is a grade 3 or greater adverse event. In some of any of the embodiments herein, the one or more adverse events is a serious adverse event. In some of any of the embodiments herein, the one or more adverse events is conjunctivitis and/or keratitis and the additional agent is a preservative-free lubricating eye drop, an ocular vasoconstrictor and/or a steroid eye drop. In some of any of the embodiments herein, the subject is a human. In some of any of the embodiments herein, the antibody-drug conjugate is in a pharmaceutical composition comprising the antibody-drug conjugate and a pharmaceutical acceptable carrier. In some of any of the embodiments herein, the platinum-based agent is in a pharmaceutical composition comprising the platinum-based agent and a pharmaceutical acceptable carrier.

Also provided herein is a kit comprising:
(a) a dosage ranging from about AUC=4 to about AUC=6 of a platinum-based agent;
(b) a dosage ranging from about 1.5 mg/kg to about 2.1 mg/kg of an antibody-drug conjugate that binds to tissue factor (TF), wherein the antibody-drug conjugate comprises an anti-TF antibody or an antigen-binding fragment thereof conjugated to a monomethyl auristatin or a functional analog thereof or a functional derivative thereof; and
(c) instructions for using the platinum-based agent and the antibody drug conjugate according to some of any of the embodiments herein. In some embodiments, the platinum-based agent is carboplatin. In some of any of the embodiments herein, the antibody-drug conjugate is tisotumab vedotin.

DETAILED DESCRIPTION

I. Definitions

Figure 1A:
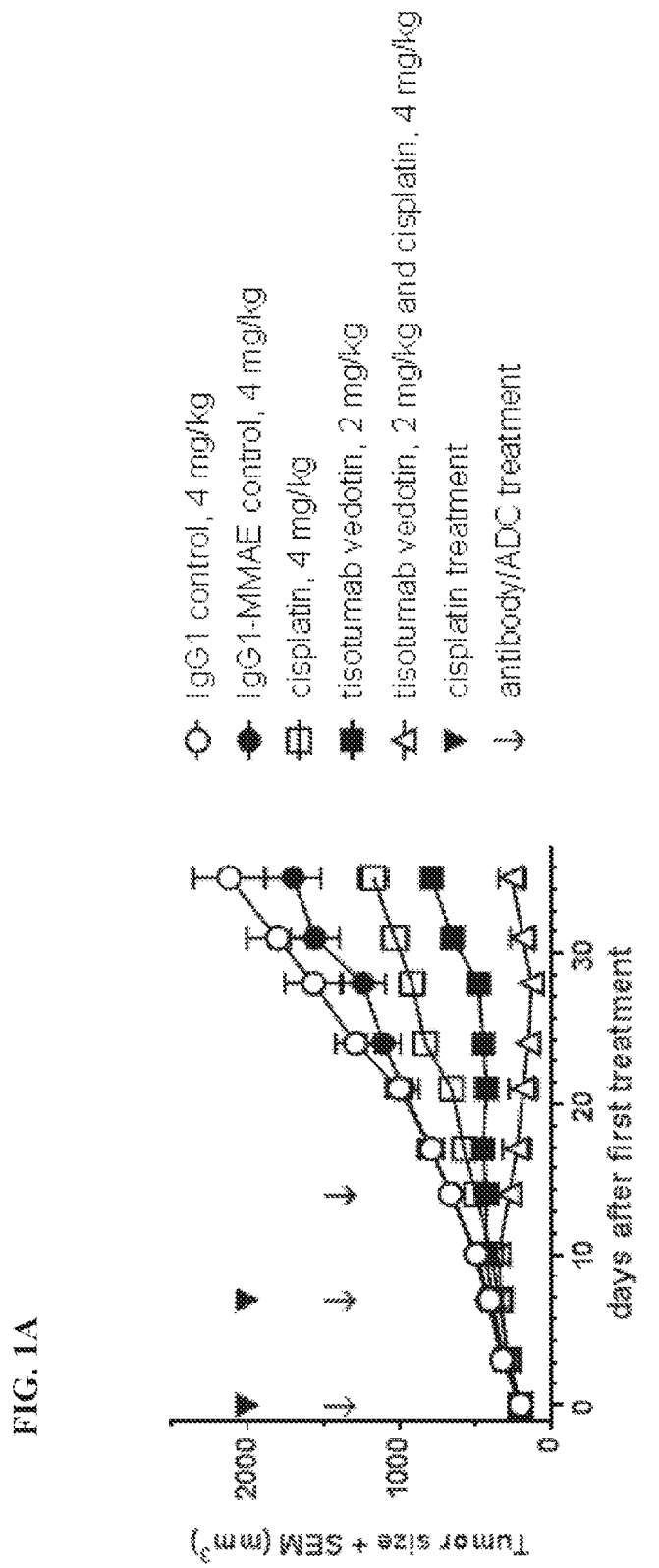
FIG. 1A-E is a series of graphs showing the anti-tumor activity of the combination of tisotumab vedotin and cisplatin in a cervical cancer xenograft mouse model. A) Average tumor size in the mice after treatment with 4 mg/kg IgG1 control (empty black circle), 4 mg/kg IgG1-MMAE control (filled black circle), 4 mg/kg cisplatin (empty black square), 2 mg/kg tisotumab vedotin (filled black square) or 2 mg/kg tisotumab vedotin combined with 4 mg/kg cisplatin (empty black triangle). Black inverted arrow indicates day of administration of tisotumab vedotin dose. Black filled inverted triangle indicates day of administration of cisplatin dose. Tumor burden was assessed by caliper measurements. Error bars indicate standard error of the mean. * indicates p<0.05 of tisotumab vedotin+cisplatin treatment versus single agent treatment. B) Average tumor size in the mice after treatment with 4 mg/kg IgG1 control (empty black circle), 4 mg/kg IgG1-MMAE control (filled black circle), 4 mg/kg cisplatin (empty black square), 4 mg/kg tisotumab vedotin (filled black square) or 4 mg/kg tisotumab vedotin combined with 4 mg/kg cisplatin (empty black triangle). Black inverted arrow indicates day of administration of tisotumab vedotin dose. Black inverted triangle indicates day of administration of cisplatin dose. Tumor burden was assessed by caliper measurements. Error bars indicate standard error of the mean. * indicates p<0.05 of tisotumab vedotin+cisplatin treatment versus single agent treatment. C) Mean tumor size in mice at Day 38 after treatment with 4 mg/kg IgG1 control (Group 01), 4 mg/kg IgG1-MMAE control (Group 02), 4 mg/kg tisotumab vedotin (Group 03), 2 mg/kg tisotumab vedotin (Group 04), 1 mg/kg tisotumab vedotin (Group 05), 0.5 mg/kg tisotumab vedotin (Group 06), 4 mg/kg cisplatin (Group 07), 4 mg/kg tisotumab vedotin combined with 4 mg/kg cisplatin (Group 08), 2 mg/kg tisotumab vedotin combined with 4 mg/kg cisplatin (Group 09), 1 mg/kg tisotumab vedotin combined with 4 mg/kg cisplatin (Group 10), or 0.5 mg/kg tisotumab vedotin combined with 4 mg/kg cisplatin (Group 11). D) Percent tumor free survival with a tumor size cut-off 1000 mm$^3$ in mice treated with 4 mg/kg IgG1-MMAE control (Group 02), 4 mg/kg tisotumab vedotin alone (Group 03), 4 mg/kg tisotumab vedotin combined with 4 mg/kg cisplatin (Group 08), or 4 mg/kg cisplatin alone (Group 07). E) Percent tumor free survival with a tumor size cut-off 1000 mm$^3$ in mice treated with 4 mg/kg IgG1-MMAE control (Group 02), 2 mg/kg tisotumab vedotin alone (Group 04), 2 mg/kg tisotumab vedotin combined with 4 mg/kg cisplatin (Group 09), or 4 mg/kg cisplatin alone (Group 07).
Figure 1B:
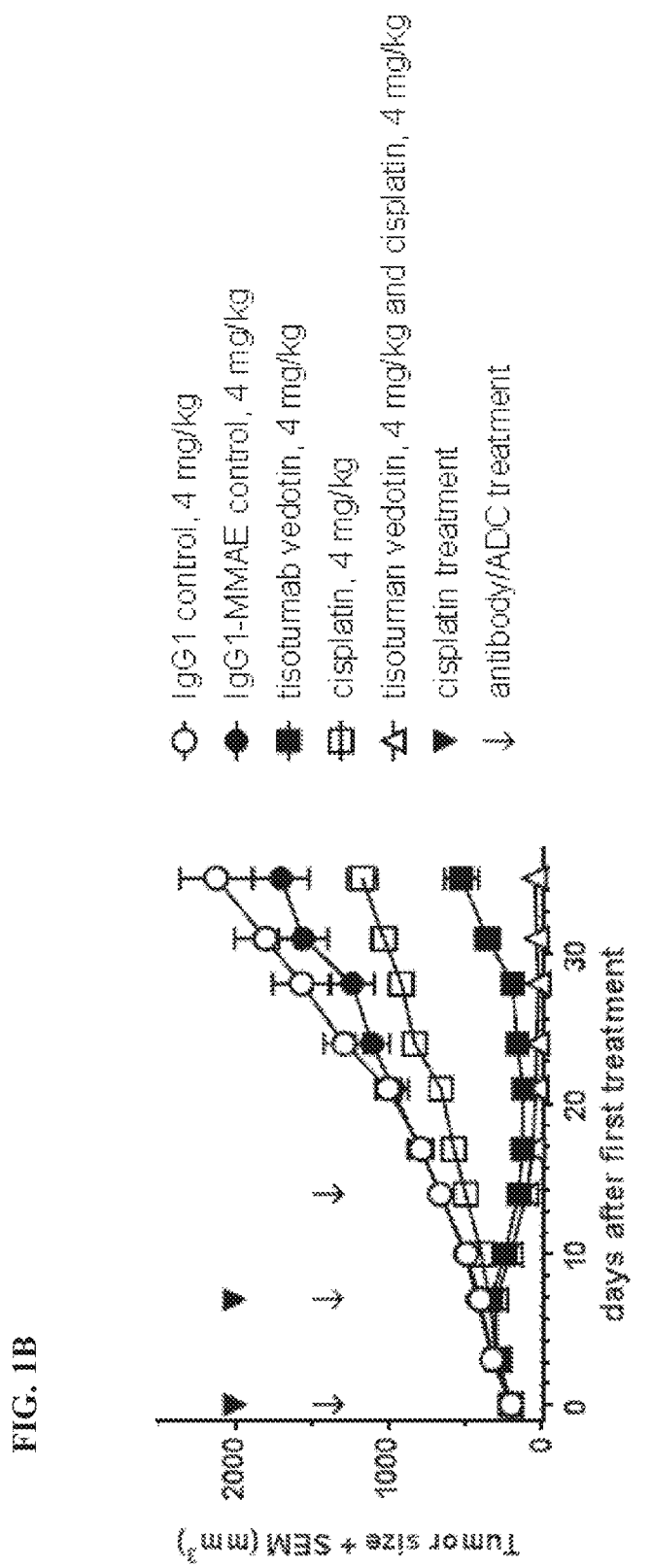
Figure 1C:
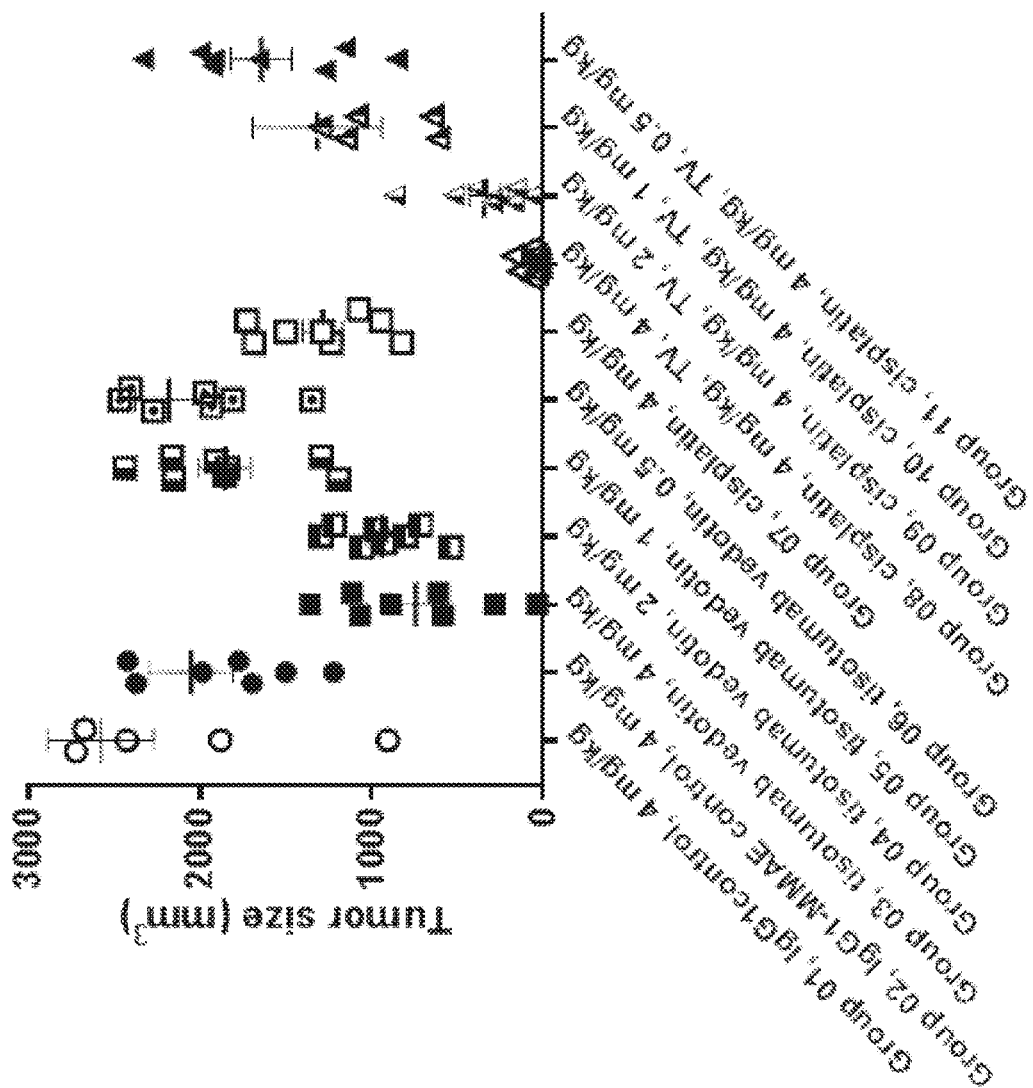

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "tissue factor", "TF", "CD142", "tissue factor antigen", "TF antigen" and "CD142 antigen" are used interchangeably herein, and, unless specified otherwise, include any variants, isoforms and species homologs of human tissue factor which are naturally expressed by cells or are expressed on cells transfected with the tissue factor gene. In some embodiments, tissue factor comprises the amino acid sequence found under Genbank accession NP_001984.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. The heavy chains are generally inter-connected via disulfide bonds in the so-called "hinge region." Each light chain typically is comprised of a light chain variable region (abbreviated herein as $V_L$ or VL) and a light chain constant region ($C_L$ or CL). The light chain constant region typically is comprised of one domain, $C_L$. The CL can be of κ (kappa) or λ (lambda) isotype. The terms "constant domain" and "constant region" are used interchangeably herein. Unless stated otherwise, the numbering of amino acid residues in the constant region is according to the EU-index as described in Kabat et al., Sequences of Proteins of Immunological Interest, 5th Ed. Public Health Service, National Institutes of Health, Bethesda, MD. (1991). An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). The terms "complementarity determining regions" and "CDRs," synonymous with "hypervariable regions" or "HVRs" are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each $V_H$ and $V_L$, three CDRs and four FRs are typically arranged from amino-terminus to carboxy-terminus in the following order: FR1, CDR1, FR2, CDR2, FR3, CDR3, FR4 (See also Chothia and Lesk J. Mot. Biol., 195, 901-917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, multispecific antibody or similar molecule.

The term "monoclonal antibody" as used herein refers to a preparation of antibody molecules that are recombinantly produced with a single primary amino acid sequence. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

An "isolated antibody" refers to an antibody that is substantially free of other antibodies having different antigenic specificities (e.g., an isolated antibody that binds specifically to TF is substantially free of antibodies that bind specifically to antigens other than TF). An isolated antibody that binds specifically to TF can, however, have cross-reactivity to other antigens, such as TF molecules from different species. Moreover, an isolated antibody can be substantially free of other cellular material and/or chemicals. In one embodiment, an isolated antibody includes an antibody conjugate attached to another agent (e.g., small molecule drug). In some embodiments, an isolated anti-TF antibody includes a conjugate of an anti-TF antibody with a small molecule drug (e.g., MMAE or MMAF).

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g.

murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

An "anti-antigen antibody" refers to an antibody that binds to the antigen. For example, an anti-TF antibody is an antibody that binds to the antigen TF.

An "antigen-binding portion" or antigen-binding fragment" of an antibody refers to one or more fragments of an antibody that retain the ability to bind specifically to the antigen bound by the whole antibody. Examples of antibody fragments (e.g., antigen-binding fragment) include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

100 times the fraction $X/Y$ where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % sequence identity of A to B will not equal the % sequence identity of B to A.

As used herein, the terms "binding", "binds" or "specifically binds" in the context of the binding of an antibody to a pre-determined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "ADC" refers to an antibody-drug conjugate, which in the context of the present invention refers to an anti-TF antibody, which is coupled to a drug moiety (e.g., MMAE or MMAF) as described in the present application.

The abbreviations "vc" and "val-cit" refer to the dipeptide valine-citrulline.

The abbreviation "PAB" refers to the self-immolative spacer:

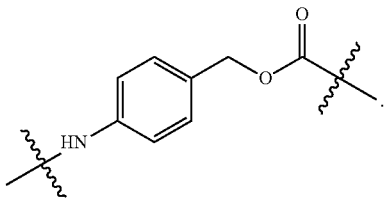 [SMILES: *Nc1ccc(COC(*)=O)cc1]

The abbreviation "MC" refers to the stretcher maleimidocaproyl:

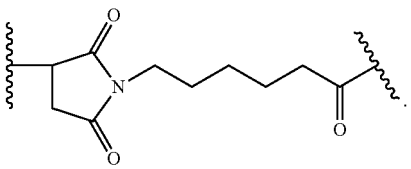 [SMILES: *C(=O)CCCCCN1C(=O)CC(*)C1=O]

The term "Ab-MC-vc-PAB-MMAE" refers to an antibody conjugated to the drug MMAE through a MC-vc-PAB linker.

A "platinum-based agent" refers to a molecule or a composition comprising a molecule containing a coordination complex comprising the chemical element platinum and useful as a chemotherapy drug. Platinum-based agents generally act by inhibiting DNA synthesis and some have alkylating activity. Platinum-based agents encompass those that are currently being used as part of a chemotherapy regimen, those that are currently in development, and those that may be developed in the future.

A "cancer" refers to a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor. For example, a "tumor derived from" a cervical cancer refers to a tumor that is the result of a metastasized cervical cancer.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is cancer.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, by at least about 95%, by at least about 96%, by at least about 97%, by at least about 98%, or by at least about 99% in a treated subject(s) (e.g., one or more treated subjects) relative to an untreated subject(s) (e.g., one or more untreated subjects). In some embodiments, a therapeutically effective amount of an anti-cancer agent inhibits cell growth or tumor growth by 100% in a treated subject(s) (e.g., one or more treated subjects) relative to an untreated subject(s) (e.g., one or more untreated subjects).

In other embodiments of the disclosure, tumor regression can be observed and continue for a period of at least about 20 days, at least about 30 days, at least about 40 days, at least about 50 days, or at least about 60 days. Notwithstanding these ultimate measurements of therapeutic effectiveness, evaluation of immunotherapeutic drugs must also make allowance for "immune-related response patterns".

A therapeutically effective amount of a drug (e.g., an anti-TF antibody-drug conjugate or a platinum-based agent) includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

As used herein, "subtherapeutic dose" means a dose of a therapeutic compound (e.g., an anti-TF antibody-drug conjugate or a platinum-based agent) that is lower than the usual or typical dose of the therapeutic compound when administered alone for the treatment of a hyperproliferative disease (e.g., cancer).

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration that is at least the same as the treatment duration, or at least 1.5, 2.0, 2.5, or 3 times longer than the treatment duration.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of complete response (CR) rate and partial response (PR) rate.

As used herein, "overall survival" or "OS" refers to the percentage of individuals in a group who are likely to be alive after a particular duration of time.

The term "weight-based dose", as referred to herein, means that a dose administered to a subject is calculated based on the weight of the subject. For example, when a subject with 60 kg body weight requires 2.0 mg/kg of a platinum-based agent or an anti-TF antibody-drug conjugate, one can calculate and use the appropriate amount of the platinum-based agent or anti-TF antibody-drug conjugate (i.e., 120 mg) for administration to said subject.

The use of the term "fixed dose" with regard to a method of the disclosure means that two or more different agents (e.g., a platinum-based agent and an anti-TF antibody-drug conjugate) are administered to a subject in particular (fixed) ratios with each other. In some embodiments, the fixed dose is based on the amount (e.g., mg) of the agents. In certain embodiments, the fixed dose is based on the concentration (e.g., mg/ml) of the agents. For example, a 3:1 ratio of a platinum-based agent to an anti-TF antibody-drug conjugate administered to a subject can mean about 240 mg of the platinum-based agent and about 80 mg of the anti-TF antibody-drug conjugate or about 3 mg/ml of the platinum-based agent and about 1 mg/ml of the anti-TF antibody-drug conjugate are administered to the subject.

The use of the term "flat dose" with regard to the methods and dosages of the disclosure means a dose that is administered to a subject without regard for the weight or body surface area (BSA) of the subject. The flat dose is therefore not provided as a mg/kg dose, but rather as an absolute amount of the agent (e.g., the anti-TF antibody-drug conjugate and/or the platinum-based agent). For example, a subject with 60 kg body weight and a subject with 100 kg body weight would receive the same dose of an antibody or an antibody-drug conjugate (e.g., 240 mg of an anti-TF antibody-drug conjugate or e.g. 750 mg of a platinum-based agent).

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt" as used herein, refers to pharmaceutically acceptable organic or inorganic salts of a compound of the invention. Exemplary salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 4,4'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Administering" or "administration" refer to the physical introduction of a therapeutic agent to a subject, using any of the various methods and delivery systems known to those skilled in the art. Exemplary routes of administration for the anti-TF antibody-drug conjugate and/or platinum-based agent include intravenous, intramuscular, subcutaneous, intraperitoneal, spinal or other parenteral routes of administration, for example by injection or infusion (e.g., intravenous infusion). The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes include a topical, epidermal or mucosal route of administration, for example, intranasally, vaginally, rectally, sublingually or topically. Administration can also be performed, for example, once, a plurality of times, and/or over one or more extended periods.

The terms "baseline" or "baseline value" used interchangeably herein can refer to a measurement or characterization of a symptom before the administration of the therapy (e.g., an anti-TF antibody-drug conjugate as described herein and/or a platinum-based agent as described herein) or at the beginning of administration of the therapy. The baseline value can be compared to a reference value in order to determine the reduction or improvement of a symptom of a disease contemplated herein, such as TF-associated disease contemplated herein (e.g., bladder cancer or cervical cancer). The terms "reference" or "reference value" used interchangeably herein can refer to a measurement or characterization of a symptom after administration of the therapy (e.g., an anti-TF antibody-drug conjugate as described herein and/or a platinum-based agent as described herein). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value: a mean value; or a value as compared to a baseline value.

Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals).

The term "monotherapy" as used herein means that the anti-TF antibody-drug conjugate or platinum-based agent is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:

Is fatal or life-threatening (as used in the definition of a serious adverse event, "life-threatening" refers to an event in which the patient was at risk of death at the time of the event; it does not refer to an event which hypothetically might have caused death if it was more severe.

Results in persistent or significant disability/incapacity

Constitutes a congenital anomaly/birth defect

Is medically significant, i.e., defined as an event that jeopardizes the patient or may require medical or surgical intervention to prevent one of the outcomes listed above. Medical and scientific judgment must be exercised in deciding whether an AE is "medically significant"

Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "once about every week," "once about every two weeks," or any other similar dosing interval terms as used herein mean approximate numbers. "Once about every week" can include every seven days±one day, i.e., every six days to every eight days. "Once about every two weeks" can include every fourteen days±two days, i.e., every twelve days to every sixteen days. "Once about every three weeks" can include every twenty-one days±three days, i.e., every eighteen days to every twenty-four days. Similar approximations apply, for example, to once about every four weeks, once about every five weeks, once about every six weeks, and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. Combination Therapy

The present invention provides anti-TF antibody-drug conjugates that binds to TF for use in the treatment of cancer wherein the antibody-drug conjugate is for administration, or to be administered in combination with a platinum-based agent wherein the antibody-drug conjugate comprises an anti-TF antibody or an antigen-binding fragment thereof conjugated to a monomethyl auristatin or a functional analog thereof or a functional derivative thereof. In another aspect the present invention provides a platinum-based agent for use in the treatment of cancer wherein the platinum-based agent is for administration, or to be administered in combination with an antibody-drug conjugate that binds to TF wherein the antibody-drug conjugate comprises an anti-TF antibody or an antigen-binding fragment thereof conjugated to a monomethyl auristatin or a functional analog thereof or a functional derivative thereof. In some embodiments, the cancer is bladder cancer. In some embodiments, the cancer is cervical cancer. In some embodiments, the cervical cancer is an advanced stage cervical cancer (e.g., stage 3 cervical cancer or stage 4 cervical cancer or metastatic cervical cancer). In some embodiments, the advanced cervical cancer is a metastatic cancer. In some embodiments, the subject has relapsed, recurrent and/or metastatic cervical cancer.

A. Anti-TF Antibody

Generally, anti-TF antibodies of the disclosure bind TF, e.g., human TF, and exert cytostatic and cytotoxic effects on malignant cells, such as bladder cancer cells or cervical cancer cells. Anti-TF antibodies of the disclosure are preferably monoclonal, and may be multispecific, human, humanized or chimeric antibodies, single chain antibodies, Fab fragments, F(ab') fragments, fragments produced by a Fab expression library, and TF binding fragments of any of the above. In some embodiments, the anti-TF antibodies of the disclosure specifically bind TF. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the anti-TF antibodies are antigen-binding fragments (e.g., human antigen-binding fragments) as described herein and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-TF antibodies or antigen-binding fragments thereof are human, murine (e.g., mouse and rat), donkey, sheep, rabbit, goat, guinea pig, camelid, horse, or chicken.

The anti-TF antibodies of the present disclosure may be monospecific, bispecific, trispecific or of greater multi specificity. Multispecific antibodies may be specific for different epitopes of TF or may be specific for both TF as well as for a heterologous protein. See, e.g., PCT publications WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; Kostelny et al., 1992, J. Immunol. 148:1547 1553.

Anti-TF antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementary determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

Numbering of amino acid residues in CDR sequences provided herein are according to the IMGT numbering scheme as described in Lefranc, M. P. et al., Dev. Comp. Immunol., 2003, 27, 55-77. CDR sequences provided herein for the anti-TF antibodies of the anti-TF antibody-drug conjugate are according to the IMGT method as described in Lefranc, M. P. et al., Dev. Comp. Immunol., 2003, 27, 55-77.

In certain embodiments antibodies of the disclosure comprise one or more CDRs of the antibody 011. See WO 2011/157741 and WO 2010/066803. The disclosure encompasses an antibody or derivative thereof comprising a heavy or light chain variable domain, said variable domain comprising (a) a set of three CDRs, in which said set of CDRs are from monoclonal antibody 011, and (b) a set of four framework regions, in which said set of framework regions differs from the set of framework regions in monoclonal antibody 011, and in which said antibody or derivative thereof binds to TF. In some embodiments, said antibody or derivative thereof specifically binds to TF. In certain embodiments, the anti-TF antibody is 011. The antibody 011 is also known as tisotumab.

In one aspect, anti-TF antibodies that compete with tisotumab binding to TF are also provided herein. Anti-TF antibodies that bind to the same epitope as tisotumab are also provided herein.

In one aspect, provided herein is an anti-TF antibody comprising 1, 2, 3, 4, 5, or 6 of the CDR sequences of tisotumab.

In one aspect, provided herein is an anti-TF antibody comprising a heavy chain variable region and a light chain variable region, wherein the heavy chain variable region comprises (i) CDR-H1 comprising the amino acid sequence of SEQ ID NO:1, (ii) CDR-H2 comprising the amino acid sequence of SEQ ID NO:2, and (iii) CDR-H3 comprising the amino acid sequence of SEQ ID NO:3; and/or wherein the light chain variable region comprises (i) CDR-L1 comprising the amino acid sequence of SEQ ID NO:4, (ii) CDR-L2 comprising the amino acid sequence of SEQ ID NO:5, and (iii) CDR-L3 comprising the amino acid sequence of SEQ ID NO:6, wherein the CDRs of the anti-TF antibody are defined by the IMGT numbering scheme.

An anti-TF antibody described herein may comprise any suitable framework variable domain sequence, provided that the antibody retains the ability to bind TF (e.g., human TF). As used herein, heavy chain framework regions are designated "HC-FR1-FR4," and light chain framework regions are designated "LC-FR1-FR4." In some embodiments, the anti-TF antibody comprises a heavy chain variable domain framework sequence of SEQ ID NO:9, 10, 11, and 12 (HC-FR1, HC-FR2, HC-FR3, and HC-FR4, respectively). In some embodiments, the anti-TF antibody comprises a light chain variable domain framework sequence of SEQ ID NO:13, 14, 15, and 16 (LC-FR1, LC-FR2, LC-FR3, and LC-FR4, respectively).

In some embodiments of the anti-TF antibodies described herein, the heavy chain variable domain comprises the amino acid sequence of EVQLLESGGGLVQPGGSLRLS-CAASGFTFSNYAMSWVRQAPGKGLEWVSSISGSGD YTYYTDSVKGRFTISRDNSKNTLYLQMNSLRAED-TAVYYCARSPWGYYLDSWGQG TLVTVSS (SEQ ID NO:7) and the light chain variable domain comprises the amino acid sequence of DIQMTQSPPSLSASAGDRVTIT-CRASQGISSRLAWYQQKPEKAPKSLIYAASSLQSGV PSRFSGSGSGTDFTLTISSLQPEDFATYYCQQYNSYPY-TFGQGTKLEIK (SEQ ID NO:8).

In some embodiments of the anti-TF antibodies described herein, the heavy chain CDR sequences comprise the following:

```
a) CDR-H1
   (GFTFSNYA (SEQ ID NO: 1));

b) CDR-H2
   (ISGSGDYT (SEQ ID NO: 2));
   and c) CDR-H3
   (ARSPWGYYLDS (SEQ ID NO: 3)).
```

In some embodiments of the anti-TF antibodies described herein, the heavy chain FR sequences comprise the following:

a) HC-FR1
(EVQLLESGGGLVQPGGSLRLSCAAS (SEQ ID NO: 9));

b) HC-FR2
(MSWVRQAPGKGLEWVSS (SEQ ID NO: 10));

c) HC-FR3
(YYTDSVKGRFTISRDNSKNTLYLQMNSLRAEDTAVYYC
(SEQ ID NO: 11));
and d) HC-FR4
(WGQGTLVTVSS(SEQ ID NO: 12)).

In some embodiments of the anti-TF antibodies described herein, the light chain CDR sequences comprise the following:

a) CDR-L1
(QGISSR (SEQ ID NO: 4));

b) CDR-L2
(AAS (SEQ ID NO: 5));
and c) CDR-L3
(QQYNSYPYT (SEQ ID NO: 6)).

In some embodiments of the anti-TF antibodies described herein, the light chain FR sequences comprise the following:

a) LC-FR1
(DIQMTQSPPSLSASAGDRVTITCRAS (SEQ ID NO: 13));

b) LC-FR2
(LAWYQQKPEKAPKSLIY (SEQ ID NO: 14));

c)
LC-FR3
(SLQSGVPSRFSGSGSGTDFTLTISSLQPEDFATYYC
(SEQ ID NO: 15));
and d) LC-FR4
(FGQGTKLEIK (SEQ ID NO: 16)).

In some embodiments, provided herein is an anti-TF antibody that binds to TF (e.g., human TF), wherein the antibody comprises a heavy chain variable region and a light chain variable region, wherein the antibody comprises:
(a) heavy chain variable domain comprising:
(1) an HC-FR1 comprising the amino acid sequence of SEQ ID NO:9;
(2) an CDR-H1 comprising the amino acid sequence of SEQ ID NO:1;
(3) an HC-FR2 comprising the amino acid sequence of SEQ ID NO:10;
(4) an CDR-H2 comprising the amino acid sequence of SEQ ID NO:2;
(5) an HC-FR3 comprising the amino acid sequence of SEQ ID NO:11;
(6) an CDR-H3 comprising the amino acid sequence of SEQ ID NO:3; and
(7) an HC-FR4 comprising the amino acid sequence of SEQ ID NO:12,
and/or
(b) a light chain variable domain comprising:
(1) an LC-FR1 comprising the amino acid sequence of SEQ ID NO:13;
(2) an CDR-L1 comprising the amino acid sequence of SEQ ID NO:4;
(3) an LC-FR2 comprising the amino acid sequence of SEQ ID NO:14;
(4) an CDR-L2 comprising the amino acid sequence of SEQ ID NO:5;
(5) an LC-FR3 comprising the amino acid sequence of SEQ ID NO:15;
(6) an CDR-L3 comprising the amino acid sequence of SEQ ID NO:6; and
(7) an LC-FR4 comprising the amino acid sequence of SEQ ID NO:16.

In one aspect, provided herein is an anti-TF antibody comprising a heavy chain variable domain comprising the amino acid sequence of SEQ ID NO:7 or comprising a light chain variable domain comprising the amino acid sequence of SEQ ID NO:8. In one aspect, provided herein is an anti-TF antibody comprising a heavy chain variable domain comprising the amino acid sequence of SEQ ID NO:7 and comprising a light chain variable domain comprising the amino acid sequence of SEQ ID NO:8.

In some embodiments, provided herein is an anti-TF antibody comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:7 contains substitutions (e.g., conservative substitutions), insertions, or deletions relative to the reference sequence and retains the ability to bind to a TF (e.g., human TF). In certain embodiments, a total of 1 to 10 amino acids have been substituted, inserted and/or deleted in SEQ ID NO:7. In certain embodiments, substitutions, insertions, or deletions (e.g., 1, 2, 3, 4, or 5 amino acids) occur in regions outside the CDRs (i.e., in the FRs). In some embodiments, the anti-TF antibody comprises a heavy chain variable domain sequence of SEQ ID NO:7 including post-translational modifications of that sequence. In a particular embodiment, the heavy chain variable domain comprises one, two or three CDRs selected from: (a) CDR-H1 comprising the amino acid sequence of SEQ ID NO:1, (b) CDR-H2 comprising the amino acid sequence of SEQ ID NO:2, and (c) CDR-H3 comprising the amino acid sequence of SEQ ID NO:3.

In some embodiments, provided herein is an anti-TF antibody comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:8 contains substitutions (e.g., conservative substitutions), insertions, or deletions relative to the reference sequence and retains the ability to bind to a TF (e.g., human TF). In certain embodiments, a total of 1 to 10 amino acids have been substituted, inserted and/or deleted in SEQ ID NO:8. In certain embodiments, substitutions, insertions, or deletions (e.g., 1, 2, 3, 4, or 5 amino acids) occur in regions outside the CDRs (i.e., in the FRs). In some embodiments, the anti-TF antibody comprises a light chain variable domain sequence of SEQ ID NO:8 including post-translational modifications of that sequence. In a particular embodiment, the light chain variable domain comprises one, two or three CDRs selected from: (a) CDR- L1 comprising the amino acid sequence of SEQ ID NO:4, (b) CDR-L2 comprising the amino acid sequence of SEQ ID NO:5, and (c) CDR-L3 comprising the amino acid sequence of SEQ ID NO:6.

In some embodiments, the anti-TF antibody comprises a heavy chain variable domain as in any of the embodiments provided above, and a light chain variable domain as in any of the embodiments provided above. In one embodiment, the antibody comprises the heavy chain variable domain sequence of SEQ ID NO:7 and the light chain variable domain sequence of SEQ ID NO:8, including post-translational modifications of those sequences.

In some embodiments, the anti-TF antibody of the anti-TF antibody-drug conjugate comprises: i) a heavy chain CDR1 comprising the amino acid sequence of SEQ ID NO: 1, a heavy chain CDR2 comprising the amino acid sequence of SEQ ID NO: 2, a heavy chain CDR3 comprising the amino acid sequence of SEQ ID NO: 3; and ii) a light chain CDR1 comprising the amino acid sequence of SEQ ID NO: 4, a light chain CDR2 comprising the amino acid sequence of SEQ ID NO: 5, and a light chain CDR3 comprising the amino acid sequence of SEQ ID NO: 6, wherein the CDRs of the anti-TF antibody are defined by the IMGT numbering scheme.

In some embodiments, the anti-TF antibody of the anti-TF antibody-drug conjugate comprises: i) an amino acid sequence having at least 85% sequence identity to a heavy chain variable region comprising the amino acid sequence of SEQ ID NO: 7, and ii) an amino acid sequence having at least 85% sequence identity to a light chain variable region comprising the amino acid sequence of SEQ ID NO: 8.

In some embodiments, the anti-TF antibody of the anti-TF antibody-drug conjugate is a monoclonal antibody.

In some embodiments, the anti-TF antibody of the anti-TF antibody-drug conjugate is tisotumab, which is also known as antibody 011 as described in WO 2011/157741 and WO 2010/066803.

Anti-TF antibodies of the present invention may also be described or specified in terms of their binding affinity to TF (e.g., human TF). Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$M, $10^{-8}$M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

There are five classes of immunoglobulins: IgA, IgD, IgE, IgG and IgM, having heavy chains designated α, δ, ε, γ and μ, respectively. The γ and a classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The antibodies also include derivatives that are modified, i.e., by the covalent attachment of any type of molecule to the antibody such that covalent attachment does not prevent the antibody from binding to TF or from exerting a cytostatic or cytotoxic effect on HD cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

B. Antibody-Drug Conjugate Structure

In some aspects, the anti-TF antibody-drug conjugates described herein comprise a linker between an anti-TF antibody or antigen-binding fragment thereof as described herein and a cytostatic or cytotoxic drug. In some embodiments the linker is a non-cleavable linker. In some embodiments the linker is a cleavable linker.

In some embodiments, the linker is a cleavable peptide linker comprising maleimido caproyl (MC), the dipeptide valine-citrulline (vc) and p-aminobenzylcarbamate (PAB). In some embodiments, the cleavable peptide linker has the formula: MC-vc-PAB-, wherein:

a) MC is:

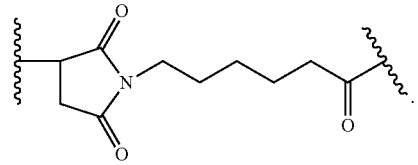 [SMILES: *C(=O)CCCCCN1C(=O)CC(*)C1=O]

b) vc is the dipeptide valine-citrulline, and
c) PAB is:

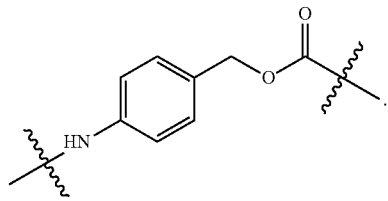 [SMILES: *Nc1ccc(COC(*)=O)cc1]

In some embodiments, the linker is a cleavable peptide linker comprising maleimido caproyl (MC). In some embodiments, the cleavable peptide linker has the formula: MC-, wherein:

a) MC is:

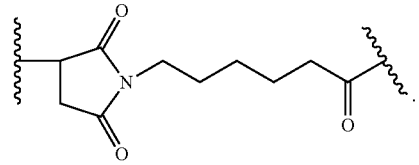 [SMILES: *C(=O)CCCCCN1C(=O)CC(*)C1=O]

In some embodiments, the linker is attached to sulphydryl residues of the anti-TF antibody or antigen-binding fragment thereof obtained by partial or full reduction of the anti-TF antibody or antigen-binding fragment thereof. In some embodiments, the linker is attached to sulphydryl residues of the anti-TF antibody or antigen-binding fragment thereof obtained by partial reduction of the anti-TF antibody or antigen-binding fragment thereof. In some embodiments, the linker is attached to sulphydryl residues of the anti-TF antibody or antigen-binding fragment thereof obtained by full reduction of the anti-TF antibody or antigen-binding fragment thereof.

In some aspects, the anti-TF antibody-drug conjugates described herein comprise a linker as described herein between an anti-TF antibody or antigen-binding fragment thereof as described herein and a cytostatic or cytotoxic drug. Auristatins have been shown to interfere with microtubule dynamics, GTP hydrolysis and nuclear and cellular division (See Woyke et al (2001) *Antimicrob. Agents and Chemother.* 45(12): 3580-3584) and have anti-cancer (See U.S. Pat. No. 5,663,149) and antifungal activity (See Pettit et al., (1998) *Antimicrob. Agents and Chemother.* 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023. In some embodiments of the anti-TF antibody-drug conjugates described herein, the cytostatic or cytotoxic drug is an auristatin or a functional analog thereof (e.g., functional peptide thereof) or a functional derivative thereof. In some embodiments, the auristatin is a monomethyl auristatin or a functional analog thereof (e.g., functional peptide thereof) or a functional derivative thereof.

In one embodiment, the auristatin is monomethyl auristatin E (MMAE):

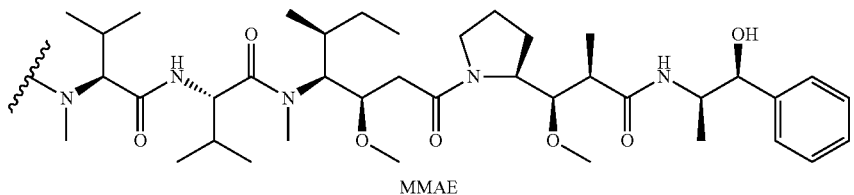 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE wherein the wavy line indicates the attachment site for the linker.

In one embodiment, the auristatin is monomethyl auristatin F (MMAF):

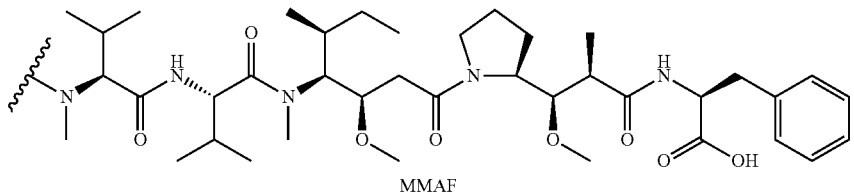

MMAF wherein the wavy line indicates the attachment site for the linker.

In one embodiment, the cleavable peptide linker has the formula: MC-vc-PAB-, and is attached to MMAE. The resulting linker-auristatin, MC-vc-PAB-MMAE is also designated vcMMAE. The vcMMAE drug linker moiety and conjugation methods are disclosed in WO2004010957, U.S. Pat. Nos. 7,659,241, 7,829,531 and 7,851,437. When vcMMAE is attached to an anti-TF antibody or antigen-binding fragment thereof as described herein, the resulting structure is:

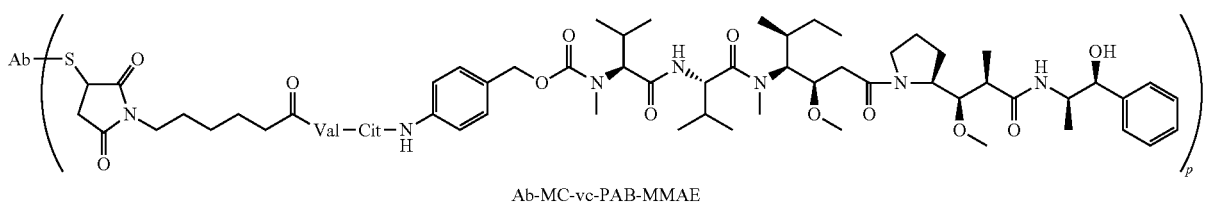

Ab-MC-vc-PAB-MMAE wherein p denotes a number from 1 to 8, e.g., 1, 2, 3, 4, 5, 6, 7 or 8, e.g., p may be from 3-5, S represents a sulphydryl residue of the anti-TF antibody and Ab designates an anti-TF antibody or antigen-binding fragment thereof as described herein. In one embodiment, the average value of p in a population of antibody-drug conjugates is about 4. In some embodiments, p is measured by hydrophobic interaction chromatography (HIC), for example by resolving drug-loaded species based on the increasing hydrophobicity with the least hydrophobic, unconjugated form eluting first and the most hydrophobic, 8-drug form eluting last with the area percentage of a peak representing the relative distribution of the particular drug-loaded antibody-drug conjugate species. See Ouyang, J., 2013, Antibody-Drug Conjugates, Methods in Molecular Biology (Methods and Protocols). In some embodiments, p is measured by reversed phase high-performance liquid chromatography (RP-HPLC), for example by first performing a reduction reaction to completely dissociate the heavy and light chains of the ADC, then separating the light and heavy chains and their corresponding drug-loaded forms on an RP column, where the percentage peak are from integration of the light chain and heavy chain peaks, combined with the assigned drug load for each peak, is used to calculate the weighted average drug to antibody ration. See Ouyang, J., 2013, Antibody-Drug Conjugates, Methods in Molecular Biology (Methods and Protocols).

In one embodiment, the cleavable peptide linker has the formula: MC-vc-PAB-, and is attached to MMAF. The resulting linker-auristatin, MC-vc-PAB-MMAF is also designated vcMMAF. In another embodiment, a non-cleavable linker MC is attached to MMAF. The resulting linker-auristatin MC-MMAF is also designated mcMMAF. Both the vcMMAF and mcMMAF drug linker moieties and conjugation methods are disclosed in WO2005081711 and U.S. Pat. No. 7,498,298. When vcMMAF or mcMMAF is attached to an anti-TF antibody or antigen-binding fragment thereof as described herein, the resulting structure is:

ment platinum and useful as a chemotherapy drug. In some embodiments, the platinum-based agent binds covalently to DNA and cross-links strands, inhibits DNA synthesis, and/or inhibits transcript. Platinum-based agents encompass those that are currently being used as part of a chemotherapy regimen, those that are currently in development, and those that may be developed in the future. Platinum-based agents include, but are not limited to, carboplatin, cisplatin, oxaliplatin, nedaplatin, triplatin tetranitrate, phenanthriplatin, picoplatin and satraplatin. In some embodiments, the platinum-based agent is carboplatin, cisplatin, oxaliplatin or nedaplatin. In some embodiments, the platinum-based agent is carboplatin. In some embodiments, the platinum-based agent is cisplatin. In some embodiments, the platinum-based agent is oxaliplatin. In some embodiments, the platinum-based agent is nedaplatin.

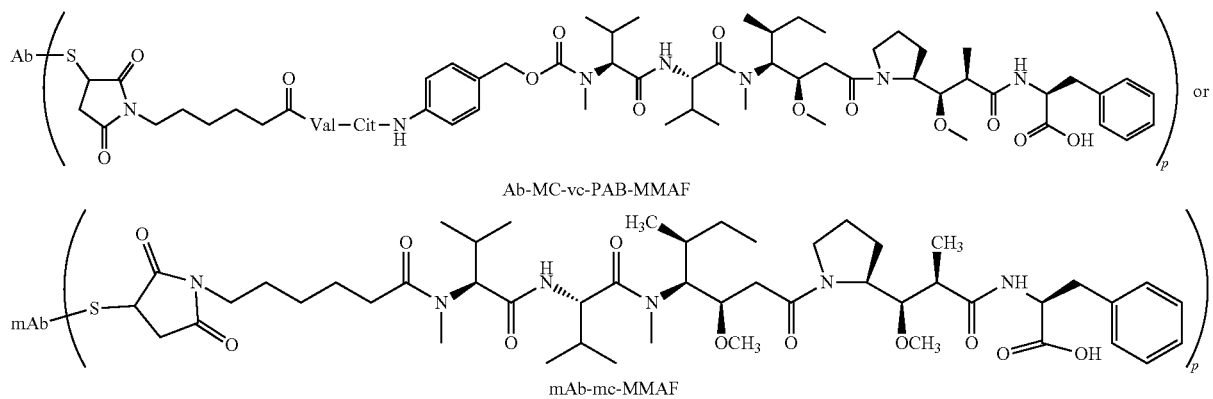

Ab-MC-vc-PAB-MMAF mAb-mc-MMAF wherein p denotes a number from 1 to 8, e.g., 1, 2, 3, 4, 5, 6, 7 or 8, e.g., p may be from 3-5, S represents a sulphydryl residue of the anti-TF antibody and Ab or mAb designates an anti-TF antibody or antigen-binding fragment thereof as described herein. In one embodiment, the average value of p in a population of antibody-drug conjugates is about 4. In some embodiments, p is measured by hydrophobic interaction chromatography (HIC), for example by resolving drug-loaded species based on the increasing hydrophobicity with the least hydrophobic, unconjugated form eluting first and the most hydrophobic, 8-drug form eluting last with the area percentage of a peak representing the relative distribution of the particular drug-loaded antibody-drug conjugate species. See Ouyang, J., 2013, Antibody-Drug Conjugates, Methods in Molecular Biology (Methods and Protocols). In some embodiments, p is measured by reversed phase high-performance liquid chromatography (RP-HPLC), for example by first performing a reduction reaction to completely dissociate the heavy and light chains of the ADC, then separating the light and heavy chains and their corresponding drug-loaded forms on an RP column, where the percentage peak are from integration of the light chain and heavy chain peaks, combined with the assigned drug load for each peak, is used to calculate the weighted average drug to antibody ration. See Ouyang, J., 2013, Antibody-Drug Conjugates, Methods in Molecular Biology (Methods and Protocols).

In one embodiment, the antibody-drug conjugate is tisotumab vedotin.

C. Platinum-Based Agent

Generally, a platinum-based agent of the disclosure is a molecule or a composition comprising a molecule containing a coordination complex comprising the chemical ele- D. Nucleic Acids, Host Cells and Methods of Production In some aspects, also provided herein are nucleic acids encoding an anti-TF antibody or antigen-binding fragment thereof as described herein. Further provided herein are vectors comprising the nucleic acids encoding an anti-TF antibody or antigen-binding fragment thereof as described herein. Further provided herein are host cells expressing the nucleic acids encoding an anti-TF antibody or antigen-binding fragment thereof as described herein. Further provided herein are host cells comprising the vectors comprising the nucleic acids encoding an anti-TF antibody or antigen-binding fragment thereof as described herein. Methods of producing an anti-TF antibody, linker and anti-TF antibody-drug conjugate are described in U.S. Pat. No. 9,168,314.

The anti-TF antibodies described herein may be prepared by well-known recombinant techniques using well known expression vector systems and host cells. In one embodiment, the antibodies are prepared in a CHO cell using the GS expression vector system as disclosed in De la Cruz Edmunds et al., 2006, *Molecular Biotechnology* 34; 179-190, EP216846, U.S. Pat. No. 5,981,216, WO 87/04462, EP323997, U.S. Pat. Nos. 5,591,639, 5,658,759, EP338841, U.S. Pat. Nos. 5,879,936, and 5,891,693.

After isolating and purifying the anti-TF antibodies from the cell media using well known techniques in the art, they are conjugated with an auristatin via a linker as described in U.S. Pat. No. 9,168,314.

Monoclonal anti-TF antibodies described herein may e.g. be produced by the hybridoma method first described by Kohler et al., *Nature,* 256, 495 (1975), or may be produced by recombinant DNA methods. Monoclonal antibodies may also be isolated from phage antibody libraries using the techniques described in, for example, Clackson et al., *Nature*, 352, 624-628 (1991) and Marks et al., *J Mol, Biol.*, 222(3):581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody (e.g., anti-TF antibody) of the invention is a human antibody. Human monoclonal antibodies directed against TF may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene minilocus that encodes unrearranged human heavy (μ and γ) and κ light chain immunoglobulin sequences, together with targeted mutations that inactivate the endogenous μ and κ chain loci (Lonberg, N. et al., *Nature*, 368, 856-859 (1994)). Accordingly, the mice exhibit reduced expression of mouse IgM or κ and in response to immunization, the introduced human heavy and light chain transgenes undergo class switching and somatic mutation to generate high affinity human IgG,κ monoclonal antibodies (Lonberg, N. et al. (1994), supra; reviewed in Lonberg, N. *Handbook of Experimental Pharmacology* 113, 49-101 (1994), Lonberg, N. and Huszar. D., *Intern. Rev. Immunol*, Vol. 13 65-93 (1995) and Harding, F. and Lonberg, N. *Ann, N.Y. Acad. Sci* 764:536-546 (1995)). The preparation of HuMAb mice is described in detail in Taylor, L. et al., *Nucleic Acids Research*. 20:6287-6295 (1992), Chen, J. et al., *International Immunology*. 5:647-656 (1993), Tuaillon at al., *J. Immunol*, 152:2912-2920 (1994), Taylor, L. et al., *International Immunology*, 6:579-591 (1994), Fishwild, D. et al., *Nature Biotechnology*, 14:845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al, EMBO J. 12:821-830 (1993)), a CMD disruption in their endogenous heavy chain genes (as described in Example 1 of WO 01/14424), a KCo5 human kappa light chain transgene (as described in Fishwild et al., *Nature Biotechnology*, 14:845-851 (1996)), and a HCo7 human heavy chain transgene (as described in U.S. Pat. No. 5,770,429).

The HCo12 mice have a JKD disruption in their endogenous light chain (kappa) genes (as described in Chen et al., *EMBO J*. 12:821-830 (1993)), a CMD disruption in their endogenous heavy chain genes (as described in Example 1 of WO 01/14424), a KCo5 human kappa light chain transgene (as described in Fishwild et al., *Nature Biotechnology*, 14:845-851 (1996)), and a HCo12 human heavy chain transgene (as described in Example 2 of WO 01/14424).

The HCo17 transgenic mouse strain (see also US 2010/0077497) was generated by coinjection of the 80 kb insert of pHC2 (Taylor et al. (1994) *Int. Immunol.*, 6:579-591), the Kb insert of pVX6, and a ~460 kb yeast artificial chromosome fragment of the yIgH24 chromosome. This line was designated (HCo17) 25950. The (HCo17) 25950 line was then bred with mice comprising the CMD mutation (described in Example 1 of PCT Publication WO 01109187), the JKD mutation (Chen et al, (1993) *EMBO J.* 12:811-820), and the (KC05) 9272 transgene (Fishwild et al. (1996) *Nature Biotechnology*, 14:845-851). The resulting mice express human immunoglobulin heavy and kappa light chain transgenes in a background homozygous for disruption of the endogenous mouse heavy and kappa light chain loci.

The HCo20 transgenic mouse strain is the result of a co-injection of minilocus 30 heavy chain transgene pHC2, the germline variable region (Vh)-containing YAC yIgH10, and the minilocus construct pVx6 (described in WO09097006). The (HCo20) line was then bred with mice comprising the CMD mutation (described in Example 1 of PCT Publication WO 01/09187), the JKD mutation (Chen et al. (1993) *EMBO J.* 12:811-820), and the (KCO5) 9272 trans gene (Fishwild eta). (1996) *Nature Biotechnology*, 14:845-851). The resulting mice express human 10 immunoglobulin heavy and kappa light chain transgenes in a background homozygous for disruption of the endogenous mouse heavy and kappa light chain loci.

In order to generate HuMab mice with the salutary effects of the Balb/c strain, HuMab mice were crossed with KCO05 [MIK] (Balb) mice which were generated by backcrossing the KC05 strain (as described in Fishwild et al. (1996) *Nature Biotechnology*, 14:845-851) to wild-type Balb/c mice to generate mice as described in WO09097006. Using this crossing Balb/c hybrids were created for HCo12, HCo17, and HCo20 strains.

In the KM mouse strain, the endogenous mouse kappa light chain gene has been homozygously disrupted as described in Chen et al., *EMBO J.* 12:811-820 (1993) and the endogenous mouse heavy chain gene has been homozygously disrupted as described in Example 1 of WO 01/09187, This mouse strain carries a human kappa light chain transgene, KCo5, as described in Fishwild et al., *Nature Biotechnology*, 14:845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well-known techniques, Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756, 687, 5,750,172 and 5,741,957.

Further, human antibodies of the present invention or antibodies of the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (See for instance Hoogenboom et al., *J. Mol, Biol.* 227(2):381-388 (1992) (phage display), Vaughan et al., *Nature Biotech,*

14:309 (1996) (phage display), Hanes and Plucthau, *PNAS USA* 94:4937-4942 (1997) (ribosomal display), Parmley and Smith, *Gene,* 73:305-318 (1988) (phage display), Scott, *TIBS.* 17:241-245 (1992), Cwirla et al., *PNAS USA,* 87:6378-6382 (1990), Russel et al., *Nucl. Acids Research,* 21:1081-4085 (1993), Hogenboom et al., *Immunol, Reviews,* 130:43-68 (1992), Chiswell and McCafferty, TIBTECH, 10:80-84 (1992), and U.S. Pat. No. 5,733,743). If display technologies are utilized to produce antibodies that are not human, such antibodies may be humanized.

III. Methods of Treatment

The invention provides methods for treating cancer in a subject with an anti-TF antibody-drug conjugate described herein and a platinum-based agent described herein. In one aspect, the antibody-drug conjugate is tisotumab vedotin. In one aspect, the platinum-based agent is carboplatin. In one aspect, the platinum-based agent is cisplatin. In a particular embodiment, the subject is a human.

In another aspect the present invention provides an antibody-drug conjugate that binds to TF for use in the treatment of cancer wherein the antibody-drug conjugate is for administration, or to be administered in combination with a platinum-based agent wherein the antibody-drug conjugate comprises an anti-TF antibody or an antigen-binding fragment thereof conjugated to a monomethyl auristatin or a functional analog thereof or a functional derivative thereof.

In another aspect the present invention provides a platinum-based agent for use in the treatment of cancer wherein the platinum-based agent is for administration, or to be administered in combination with an antibody-drug conjugate that binds to TF wherein the antibody-drug conjugate comprises an anti-TF antibody or an antigen-binding fragment thereof conjugated to a monomethyl auristatin or a functional analog thereof or a functional derivative thereof.

A. Bladder Cancer

Bladder cancer is the fifth most common cancer diagnosis in the US. The American Cancer Society (ACS) estimated that there were 70980 new patients of bladder cancer in 2009 and that 14330 persons die of bladder cancer each year. ACS also estimated that the bladder cancer morbidity is 1/27 for males and 1/85 for females and that 90% of bladder cancer patients are over 55 years old. Invasive bladder cancer may spread to lymph nodes, other organs in the pelvis (causing problems with kidney and bowel function), or other organs in the body, such as the liver and lungs. Standard treatments for bladder cancer are surgery, radiation therapy, chemotherapy, and biological therapy.

In some aspects, the invention provides methods for treating bladder cancer in a subject with an anti-TF antibody-drug conjugate described herein and a platinum-based agent described herein. In one aspect, the antibody-drug conjugate is tisotumab vedotin. In one aspect, the platinum-based agent is carboplatin. In one aspect, the platinum-based agent is cisplatin. In a particular embodiment, the subject is a human.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the bladder cancer cells from the subject express TF. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the bladder cancer cells from the subject express TF. In some embodiments, the percentage of cells that express TF is determined using immunohistochemistry (IHC). In some embodiments, the percentage of cells that express TF is determined using flow cytometry. In some embodiments, the percentage of cells that express TF is determined using an enzyme-linked immunosorbent assay (ELISA).

B. Cervical Cancer

Cervical cancer remains to be one of the leading causes of cancer-related death in women despite advances in screening, diagnosis, prevention, and treatment. It accounts for ~4% of the total newly diagnosed cancer cases and 4% of the total cancer deaths. See Zhu et al., 2016, *Drug Des. Devel. Ther.* 10:1885-1895. Cervical cancer is the $7^{th}$ most common female cancer worldwide and the $16^{th}$ most common cancer in the European Union. Depending on the stage at initial presentation, cervical cancer will recur in 25-61% of women. See Tempfer et al., 2016, *Oncol. Res. Treat.* 39:525-533. In most cases, recurrent disease is diagnosed within 2 years of the initial treatment and may be observed in various sites. Chemotherapy is the standard treatment for these patients. See Zhu et al., 2016, *Drug Des. Devel. Ther.* 10:1885-1895. The median overall survival exceeds one year now, however, the five year relative survival for stage IV cervical cancer is only 15%, demonstrating the high need for improved methods of treating cervical cancer.

In some aspects, provided herein are methods for treating cervical cancer in a subject with an anti-TF antibody-drug conjugate described herein and a platinum-based agent described herein. In one aspect, the antibody-drug conjugate is tisotumab vedotin. In one aspect, the platinum-based agent is carboplatin. In one aspect, the platinum-based agent is cisplatin. In some embodiments, the subject has not previously received prior systemic therapy for the cervical cancer. In some embodiments, chemotherapy is not considered a prior systemic therapy for the cervical cancer. In some embodiments, radiation therapy is not considered a prior systemic therapy for the cervical cancer. In some embodiments, chemotherapy in combination with radiation therapy is not considered a prior systemic therapy for the cervical cancer. In some embodiments, the subject has been previously treated with chemotherapy and/or radiation therapy. In some embodiments, the subject is not a candidate for curative therapy. In some embodiments, the curative therapy is radiotherapy and/or exenterative therapy. In some embodiments, the curative therapy is radiotherapy. In some embodiments, the curative therapy is exenterative therapy. In a particular embodiment, the subject is a human.

In some embodiments of the methods or uses or product for uses provided herein, the cervical cancer is an adenocarcinoma, an adenosquamous carcinoma, a squamous cell carcinoma, a small cell carcinoma, a neuroendocrine tumor, a glassy cell carcinoma or a villoglandular adenocarcinoma. In some embodiments, the cervical cancer is an adenocarcinoma, an adenosquamous carcinoma or a squamous cell carcinoma. In some embodiments, the cervical cancer is an adenocarcinoma. In some embodiments, the cervical cancer is an adenosquamous carcinoma. In some embodiments, the cervical cancer is a squamous cell carcinoma.

In some embodiments, at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells from the subject express TF. In some embodiments, at least 0.1%, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, or at least 80% of the cervical cancer cells from the subject express TF. In some embodiments, the percentage of cells that express TF is determined using immunohistochemistry (IHC). In some embodiments, the percentage of cells that express TF is determined using flow cytometry. In some embodiments, the percentage of cells that express TF is determined using an enzyme-linked immunosorbent assay (ELISA).

In some embodiments of the methods or uses or product for uses provided herein, the cervical cancer is a stage 0, 1, 2, 3, or 4 cervical cancer. In some embodiments, the cervical cancer is a stage 0, 1A, 1B, 2A, 2B, 3A, 3B, 4A or 4B cervical cancer. In some embodiments, the cervical cancer is staged by the International Federation of Gynecology and Obstetrics (FIGO) staging system. In some embodiments, the staging is based on clinical examination. In some embodiments, in stage 0 cervical cancer the carcinoma is confined to the surface layer (cells lining) the cervix. In some embodiments, in stage 1 cervical cancer the carcinoma has grown deeper into the cervix but has not yet spread beyond it. In some embodiments, in stage 1A cervical cancer the invasive carcinoma can be diagnosed only by microscopy and the deepest invasion is less than 5 mm and the largest extension is less than 7 mm. In some embodiments, in stage 1B cervical cancer the lesions are clinically visible and are limited to the cervix uteri. In some embodiments, in stage 2 cervical cancer the cervical carcinoma has invaded beyond the uterus, but not to the pelvic wall or to the lower third of the vagina. In some embodiments, in stage 2A cervical cancer there is no parametrial invasion. In some embodiments, in stage 2B cervical cancer there is parametrial invasion. In some embodiments, in stage 3 cervical cancer the tumor extends to the pelvic wall and/or involves the lower third of the vagina and/or causes hydronephrosis or non-functioning kidney. In some embodiments, in stage 3A cervical cancer the tumor involves the lower third of the vagina, with no extension to the pelvic wall. In some embodiments, in stage 3B cervical cancer extends to the pelvic wall and/or cause hydronephrosis or non-functioning kidney. In some embodiments, in stage 4 cervical cancer, the carcinoma has extended beyond the true pelvis or has involved the mucosa of the bladder or rectum. In some embodiments, in stage 4A cervical cancer the tumor has spread to adjacent organs. In some embodiments, in stage 4B cervical cancer the tumor has spread to distant organs. In some embodiments, the cervical cancer is an advanced stage cervical cancer. In some embodiments, the advanced stage cervical cancer is a grade 3 or grade 4 cervical cancer. In some embodiments, the advanced stage cervical cancer is metastatic cervical cancer. In some embodiments, the cervical cancer is metastatic and recurrent cervical cancer. In some embodiments, the cervical cancer is metastatic cervical cancer. In some embodiments, the cervical cancer is recurrent cervical cancer.

In some embodiments of the methods or uses or product for uses provided herein, the subject has not received prior systemic therapy for the cervical cancer. In some embodiments, chemotherapy is not considered a prior systemic therapy for the cervical cancer. In some embodiments, radiation therapy is not considered a prior systemic therapy for the cervical cancer. In some embodiments, chemotherapy in combination with radiation therapy is not considered a prior systemic therapy for the cervical cancer. In some embodiments, the subject has been previously treated with chemotherapy and/or radiation therapy. In some embodiments, the subject did not respond to the treatment with chemotherapy and radiation therapy. In some embodiments, the subject received treatment for the cervical cancer with chemotherapy and did not respond to the chemotherapy. In some embodiments, the subject received treatment for the cervical cancer with irradiation and did not respond to the irradiation. In some embodiments, the subject relapsed after treatment with chemotherapy and radiation therapy. In some embodiments, the subject received treatment for the cervical cancer with chemotherapy and relapsed after treatment with the chemotherapy. In some embodiments, the subject received treatment for the cervical cancer with irradiation and relapsed after treatment with irradiation. In some embodiments, the subject experienced disease progression after treatment with chemotherapy and/or radiation therapy. In some embodiments, the subject received treatment for the cervical cancer with chemotherapy and experienced disease progression after treatment with the chemotherapy. In some embodiments, the subject received treatment for the cervical cancer with irradiation and experienced disease progression after treatment with irradiation. In some embodiments, the subject has been previously treated for the cervical cancer with one or more therapeutic agents. In some embodiments, the subject has been previously treated with one or more therapeutic agents and did not respond to the treatment. In some embodiments, the subject has been previously treated with one or more therapeutic agents and relapsed after the treatment. In some embodiments, the subject has been previously treated with one or more therapeutic agents and experienced disease progression during treatment. In some embodiments, the one or more therapeutic agents is selected from the group consisting of a chemotherapeutic agent, pemetrexed, nab-paclitaxel, vinorelbine, bevacizumab, cisplatin, carboplatin, paclitaxel, topotecan, a combination of bevacizumab and paclitaxel, a combination of bevacizumab and cisplatin, a combination of bevacizumab and carboplatin, a combination of paclitaxel and topotecan, a combination of bevacizumab and topotecan, a combination of bevacizumab, cisplatin and paclitaxel, a combination of bevacizumab, carboplatin and paclitaxel, and a combination of bevacizumab, paclitaxel and topotecan. In some embodiments, the one or more therapeutic agents is a chemotherapeutic agent. In some embodiments, the one or more therapeutic agents is bevacizumab. In some embodiments, the one or more therapeutic agents is cisplatin, In some embodiments, the one or more therapeutic agents is carboplatin. In some embodiments, the one or more therapeutic agents is paclitaxel. In some embodiments, the one or more therapeutic agents is topotecan. In some embodiments, the one or more therapeutic agents is a combination of bevacizumab and paclitaxel. In some embodiments, the one or more therapeutic agents is a combination of bevacizumab and cisplatin. In some embodiments, the one or more therapeutic agents is a combination of bevacizumab and carboplatin. In some embodiments, the one or more therapeutic agents is a combination of paclitaxel and topotecan. In some embodiments, the one or more therapeutic agents is a combination of bevacizumab and topotecan. In some embodiments, the one or more therapeutic agents is a combination of bevacizumab, cisplatin and paclitaxel. In some embodiments, the one or more therapeutic agents is a combination of bevacizumab, carboplatin and paclitaxel. In some embodiments, the one or more therapeutic agents is a combination of bevacizumab, paclitaxel and topotecan. In some embodiments, the subject is not a candidate for curative therapy. In some embodiments, the curative therapy is radiotherapy and/or exenterative therapy. In some embodiments, the curative therapy is radiotherapy. In some embodiments, the curative therapy is exenterative therapy. In a particular embodiment, the subject is a human.

C. Routes of Administration

A platinum-based agent described herein and/or anti-TF antibody-drug conjugate or antigen-binding fragment thereof described herein can be administered by any suitable route and mode. Suitable routes of administering a platinum-based agent and/or antibody-drug conjugate of the present invention are well known in the art and may be selected by those of ordinary skill in the art. In one embodiment, the platinum-based agent and/or anti-TF antibody-drug conjugate are administered parenterally. Parenteral administration refers to modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In some embodiments, the route of administration of an anti-TF antibody-drug conjugate or antigen-binding fragment described herein is intravenous injection or infusion. In some embodiments, the route of administration of an anti-TF antibody-drug conjugate or antigen-binding fragment described herein is intravenous infusion. In some embodiments, the route of administration of a platinum-based agent described herein is intravenous injection or infusion. In some embodiments, the route of administration of a platinum-based agent described herein is intravenous infusion.

D. Dosage and Frequency of Administration

In one aspect, the present invention provides for methods of treating a subject with cancer as described herein with a particular dose of an anti-TF antibody-drug conjugate or antigen-binding fragment thereof as described herein and a platinum-based agent as described herein, wherein the subject is administered the antibody-drug conjugate or antigen-binding fragment thereof as described herein and the platinum-based agent as described herein with particular frequencies.

In one embodiment of the methods or uses or product for uses provided herein, an anti-TF antibody-drug conjugate or antigen-binding fragment thereof as described herein is administered to the subject at a dose ranging from about 0.9 mg/kg to about 2.1 mg/kg of the subject's body weight. In certain embodiments, the dose is about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg or about 2.1 mg/kg. In one embodiment, the dose is about 2.0 mg/kg. In certain embodiments, the dose is 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg or 2.1 mg/kg. In one embodiment, the dose is 2.0 mg/kg. In some embodiments, the dose is 2.0 mg/kg and the anti-TF antibody-drug conjugate is tisotumab vedotin. In one embodiment, the dose is about 1.3 mg/kg. In one embodiment, the dose is 1.3 mg/kg. In some embodiments, the dose is 1.3 mg/kg and the anti-TF antibody-drug conjugate is tisotumab vedotin. In some embodiments, for a subject weighing more than 100 kg, the dose of the anti-TF antibody-drug conjugate administered is the amount that would be administered if the subject weighed 100 kg. In some embodiments, for a subject weighing more than 100 kg, the dose of the anti-TF antibody-drug conjugate administered is 65 mg, 90 mg, 130 mg, or 200 mg.

In one embodiment of the methods or uses or product for uses provided herein, an anti-TF antibody-drug conjugate or antigen-binding fragment thereof as described herein is administered to the subject once about every 1 to 4 weeks. In certain embodiments, an anti-TF antibody-drug conjugate or antigen-binding fragment thereof as described herein is administered once about every 1 week, once about every 2 weeks, once about every 3 weeks or once about every 4 weeks. In one embodiment, an anti-TF antibody-drug conjugate or antigen-binding fragment thereof as described herein is administered once about every 3 weeks. In one embodiment, an anti-TF antibody-drug conjugate or antigen-binding fragment thereof as described herein is administered once every 3 weeks. In some embodiments, the dose is about 0.9 mg/kg and is administered once about every 1 week. In some embodiments, the dose is about 0.9 mg/kg and is administered once about every 2 weeks. In some embodiments, the dose is about 0.9 mg/kg and is administered once about every 3 weeks. In some embodiments, the dose is about 0.9 mg/kg and is administered once about every 4 weeks. In some embodiments, the dose is about 1.0 mg/kg and is administered once about every 1 week. In some embodiments, the dose is about 1.0 mg/kg and is administered once about every 2 weeks. In some embodiments, the dose is about 1.0 mg/kg and is administered once about every 3 weeks. In some embodiments, the dose is about 1.0 mg/kg and is administered once about every 4 weeks. In some embodiments, the dose is about 1.1 mg/kg and is administered once about every 1 week. In some embodiments, the dose is about 1.1 mg/kg and is administered once about every 2 weeks. In some embodiments, the dose is about 1.1 mg/kg and is administered once about every 3 weeks. In some embodiments, the dose is about 1.1 mg/kg and is administered once about every 4 weeks. In some embodiments, the dose is about 1.2 mg/kg and is administered once about every 1 week. In some embodiments, the dose is about 1.2 mg/kg and is administered once about every 2 weeks. In some embodiments, the dose is about 1.2 mg/kg and is administered once about every 3 weeks. In some embodiments, the dose is about 1.2 mg/kg and is administered once about every 4 weeks. In some embodiments, the dose is about 1.3 mg/kg and is administered once about every 1 week. In some embodiments, the dose is about 1.3 mg/kg and is administered once about every 2 weeks. In some embodiments, the dose is about 1.3 mg/kg and is administered once about every 3 weeks. In some embodiments, the dose is about 1.3 mg/kg and is administered once about every 4 weeks. In some embodiments, the dose is about 1.4 mg/kg and is administered once about every 1 week. In some embodiments, the dose is about 1.4 mg/kg and is administered once about every 2 weeks. In some embodiments, the dose is about 1.4 mg/kg and is administered once about every 3 weeks. In some embodiments, the dose is about 1.4 mg/kg and is administered once about every 4 weeks. In some embodiments, the dose is about 1.5 mg/kg and is administered once about every 1 week. In some embodiments, the dose is about 1.5 mg/kg and is administered once about every 2 weeks. In some embodiments, the dose is about 1.5 mg/kg and is administered once about every 3 weeks. In some embodiments, the dose is about 1.5 mg/kg and is administered once about every 4 weeks. In some embodiments, the dose is about 1.6 mg/kg and is administered once about every 1 week. In some embodiments, the dose is about 1.6 mg/kg and is administered once about every 2 weeks. In some embodiments, the dose is about 1.6 mg/kg and is administered once about every 3 weeks. In some embodiments, the dose is about 1.6 mg/kg and is administered once about every 4 weeks. In some embodiments, the dose is about 1.7 mg/kg and is administered once about every 1 week. In some embodiments, the dose is about 1.7 mg/kg and is administered once about every 2 weeks. In some embodiments, the dose is about 1.7 mg/kg and is administered once about every 3 weeks. In some embodiments, the dose is about 1.7 mg/kg and is administered once about every 4 weeks. In some embodiments, the dose is about 1.8 mg/kg and is administered once about every 1 week. In some embodiments, the dose is about 1.8 mg/kg and is administered once about every 2 weeks. In some embodiments, the dose is about 1.8 mg/kg and is administered once about every 3 weeks. In some embodiments, the dose is about 1.8 mg/kg and is administered once about every 4 weeks. In some embodiments, the dose is about 1.9 mg/kg and is administered once about every 1 week. In some embodiments, the dose is about 1.9 mg/kg and is administered once about every 2 weeks. In some embodiments, the dose is about 1.9 mg/kg and is administered once about every 3 weeks. In some embodiments, the dose is about 1.9 mg/kg and is administered once about every 4 weeks. In some embodiments, the dose is about 2.0 mg/kg and is administered once about every 1 week. In some embodiments, the dose is about 2.0 mg/kg and is administered once about every 2 weeks. In some embodiments, the dose is about 2.0 mg/kg and is administered once about every 3 weeks. In some embodiments, the dose is about 2.0 mg/kg and is administered once about every 4 weeks. In some embodiments, the dose is about 2.1 mg/kg and is administered once about every 1 week. In some embodiments, the dose is about 2.1 mg/kg and is administered once about every 2 weeks. In some embodiments, the dose is about 2.1 mg/kg and is administered once about every 3 weeks. In some embodiments, the dose is about 2.1 mg/kg and is administered once about every 4 weeks. In some embodiments, the dose is 0.9 mg/kg and is administered once about every 1 week. In some embodiments, the dose is 0.9 mg/kg and is administered once about every 2 weeks. In some embodiments, the dose is 0.9 mg/kg and is administered once about every 3 weeks. In some embodiments, the dose is 0.9 mg/kg and is administered once about every 4 weeks. In some embodiments, the dose is 1.0 mg/kg and is administered once about every 1 week. In some embodiments, the dose is 1.0 mg/kg and is administered once about every 2 weeks. In some embodiments, the dose is 1.0 mg/kg and is administered once about every 3 weeks. In some embodiments, the dose is 1.0 mg/kg and is administered once about every 4 weeks. In some embodiments, the dose is 1.1 mg/kg and is administered once about every 1 week. In some embodiments, the dose is 1.1 mg/kg and is administered once about every 2 weeks. In some embodiments, the dose is 1.1 mg/kg and is administered once about every 3 weeks. In some embodiments, the dose is 1.1 mg/kg and is administered once about every 4 weeks. In some embodiments, the dose is 1.2 mg/kg and is administered once about every 1 week. In some embodiments, the dose is 1.2 mg/kg and is administered once about every 2 weeks. In some embodiments, the dose is 1.2 mg/kg and is administered once about every 3 weeks. In some embodiments, the dose is 1.2 mg/kg and is administered once about every 4 weeks.

In some embodiments, the dose is 1.3 mg/kg and is administered once about every 1 week. In some embodiments, the dose is 1.3 mg/kg and is administered once about every 2 weeks. In some embodiments, the dose is 1.3 mg/kg and is administered once about every 3 weeks. In some embodiments, the dose is 1.3 mg/kg and is administered once about every 4 weeks. In some embodiments, the dose is 1.4 mg/kg and is administered once about every 1 week. In some embodiments, the dose is 1.4 mg/kg and is administered once about every 2 weeks. In some embodiments, the dose is 1.4 mg/kg and is administered once about every 3 weeks. In some embodiments, the dose is 1.4 mg/kg and is administered once about every 4 weeks. In some embodiments, the dose is 1.5 mg/kg and is administered once about every 1 week. In some embodiments, the dose is 1.5 mg/kg and is administered once about every 2 weeks. In some embodiments, the dose is 1.5 mg/kg and is administered once about every 3 weeks. In some embodiments, the dose is 1.5 mg/kg and is administered once about every 4 weeks. In some embodiments, the dose is 1.6 mg/kg and is administered once about every 1 week. In some embodiments, the dose is 1.6 mg/kg and is administered once about every 2 weeks. In some embodiments, the dose is 1.6 mg/kg and is administered once about every 3 weeks. In some embodiments, the dose is 1.6 mg/kg and is administered once about every 4 weeks. In some embodiments, the dose is 1.7 mg/kg and is administered once about every 1 week. In some embodiments, the dose is 1.7 mg/kg and is administered once about every 2 weeks. In some embodiments, the dose is 1.7 mg/kg and is administered once about every 3 weeks. In some embodiments, the dose is 1.7 mg/kg and is administered once about every 4 weeks. In some embodiments, the dose is 1.8 mg/kg and is administered once about every 1 week. In some embodiments, the dose is 1.8 mg/kg and is administered once about every 2 weeks. In some embodiments, the dose is 1.8 mg/kg and is administered once about every 3 weeks. In some embodiments, the dose is 1.8 mg/kg and is administered once about every 4 weeks. In some embodiments, the dose is 1.9 mg/kg and is administered once about every 1 week. In some embodiments, the dose is 1.9 mg/kg and is administered once about every 2 weeks. In some embodiments, the dose is 1.9 mg/kg and is administered once about every 3 weeks. In some embodiments, the dose is 1.9 mg/kg and is administered once about every 4 weeks. In some embodiments, the dose is 2.0 mg/kg and is administered once about every 1 week. In some embodiments, the dose is 2.0 mg/kg and is administered once about every 2 weeks. In some embodiments, the dose is 2.0 mg/kg and is administered once about every 3 weeks. In some embodiments, the dose is 2.0 mg/kg and is administered once about every 4 weeks. In some embodiments, the dose is 2.1 mg/kg and is administered once about every 1 week. In some embodiments, the dose is 2.1 mg/kg and is administered once about every 2 weeks. In some embodiments, the dose is 2.1 mg/kg and is administered once about every 3 weeks. In some embodiments, the dose is 2.1 mg/kg and is administered once about every 4 weeks. In some embodiments, the dose is 2.0 mg/kg and is administered once about every 3 weeks (e.g., ±3 days). In some embodiments, the dose is 2.0 mg/kg and is administered once every 3 weeks. In some embodiments, the dose is 2.0 mg/kg and is administered once every 3 weeks and the antibody-drug conjugate is tisotumab vedotin. In some embodiments, the dose is 2.0 mg/kg and is administered once every 3 weeks and the antibody-drug conjugate is tisotumab vedotin and the dose is decreased to 1.3 mg/kg if one or more adverse events occur. In some embodiments, the dose is 1.3 mg/kg and is administered once every 3 weeks. In some embodiments, the dose is 1.3 mg/kg and is administered once every 3 weeks and the antibody-drug conjugate is tisotumab vedotin. In some embodiments, the dose is 1.3 mg/kg and is administered once every 3 weeks and the antibody-drug conjugate is tisotumab vedotin and the dose is decreased to 0.9 mg/kg if one or more adverse events occur.

In one embodiment of the methods or uses or product for uses provided herein, an anti-TF antibody-drug conjugate or antigen-binding fragment thereof as described herein is administered to the subject at a flat dose ranging from about 50 mg to about 200 mg such as at a flat dose of about 50 mg or a flat dose of about 60 mg or a flat dose of about 70 mg or a flat dose of about 80 mg or a flat dose of about 90 mg or a flat dose of about 100 mg or a flat dose of about 110 mg or a flat dose of about 120 mg or a flat dose of about 130 mg or a flat dose of about 140 mg or a flat dose of about 150 mg or a flat dose of about 160 mg or a flat dose of about 170 mg or a flat dose of about 180 mg or a flat dose of about 190 mg or a flat dose of about 200 mg. In some embodiments, the flat dose is administered to the subject once about every 1 to 4 weeks. In certain embodiments, the flat dose is administered to the subject once about every 1 week, once about every 2 weeks, once about every 3 weeks or once about every 4 weeks. In some embodiments, the flat dose is administered to the subject once about every 3 weeks (e.g., ±3 days). In some embodiments, the flat dose is administered to the subject once every 3 weeks. In some embodiments, the flat dose is administered to the subject once every 3 weeks and the antibody-drug conjugate is tisotumab vedotin.

In one embodiment of the methods or uses or product for uses provided herein, an anti-TF antibody-drug conjugate or antigen-binding fragment thereof as described herein is administered to the subject at a flat dose ranging from 50 mg to 200 mg such as at a flat dose of 50 mg or a flat dose of 60 mg or a flat dose of 70 mg or a flat dose of 80 mg or a flat dose of 90 mg or a flat dose of 100 mg or a flat dose of 110 mg or a flat dose of 120 mg or a flat dose of 130 mg or a flat dose of 140 mg or a flat dose of 150 mg or a flat dose of 160 mg or a flat dose of 170 mg or a flat dose of 180 mg or a flat dose of 190 mg or a flat dose of 200 mg. In some embodiments, the flat dose is administered to the subject once about every 1 to 4 weeks. In certain embodiments, the flat dose is administered to the subject once about every 1 week, once about every 2 weeks, once about every 3 weeks or once about every 4 weeks. In some embodiments, the flat dose is administered to the subject once about every 3 weeks (e.g., ±3 days). In some embodiments, the flat dose is administered to the subject once every 3 weeks. In some embodiments, the flat dose is administered to the subject once every 3 weeks and the antibody-drug conjugate is tisotumab vedotin.

In one embodiment of the methods or uses or product for uses provided herein, a platinum-based agent described herein, such as carboplatin, is administered to the subject at a dose based on the Calvert formula:

$$\text{Platinum-based agent dose (mg)} = (\text{Target AUC}) \times (\text{GFR} + 25)$$

wherein AUC stands for "area under the concentration versus time curve" (AUC is expressed in mg/mL·min) and GFR stands for "glomular filtration rate" (GFR is expressed in mL/min). In some embodiments, GFR is estimated by calculated creatine clearance. In some embodiments, serum creatine is measured by the IDMS method. In some embodiments, the platinum-based agent described herein, such as carboplatin, is administered at a dose between about AUC=4 and about AUC=6. In some embodiments, the dose of the platinum-based agent described herein, such as carboplatin, is about any of AUC=4, AUC=4.5, AUC=5, AUC=5.5, or AUC=6. In some embodiments, the dose of the platinum-based agent described herein, such as carboplatin, is about AUC=5. In some embodiments, the dose of the platinum-based agent described herein, such as carboplatin, is AUC=5. In some embodiments, the dose is about AUC=4 and is administered once about every 1 week. In some embodiments, the dose is about AUC=4 and is administered once about every 2 week. In some embodiments, the dose is about AUC=4 and is administered once about every 3 week. In some embodiments, the dose is about AUC=4 and is administered once about every 4 week. In some embodiments, the dose is about AUC=4.5 and is administered once about every 1 week. In some embodiments, the dose is about AUC=4.5 and is administered once about every 2 week. In some embodiments, the dose is about AUC=4.5 and is administered once about every 3 week. In some embodiments, the dose is about AUC=4.5 and is administered once about every 4 week. In some embodiments, the dose is about AUC=5 and is administered once about every 1 week. In some embodiments, the dose is about AUC=5 and is administered once about every 2 week. In some embodiments, the dose is about AUC=5 and is administered once about every 3 week. In some embodiments, the dose is about AUC=5 and is administered once about every 4 week. In some embodiments, the dose is about AUC=5.5 and is administered once about every 1 week. In some embodiments, the dose is about AUC=5.5 and is administered once about every 2 week. In some embodiments, the dose is about AUC=5.5 and is administered once about every 3 week. In some embodiments, the dose is about AUC=5.5 and is administered once about every 4 week. In some embodiments, the dose is about AUC=6 and is administered once about every 1 week. In some embodiments, the dose is about AUC=6 and is administered once about every 2 week. In some embodiments, the dose is about AUC=6 and is administered once about every 3 week. In some embodiments, the dose is about AUC=6 and is administered once about every 4 week. In some embodiments, the dose of the platinum-based agent described herein, such as carboplatin, is any of AUC=4, AUC=4.5, AUC=5, AUC=5.5, or AUC=6. In some embodiments, the dose of the platinum-based agent described herein, such as carboplatin, is AUC=5. In some embodiments, the dose of the platinum-based agent described herein, such as carboplatin, is AUC=5. In some embodiments, the dose is AUC=4 and is administered once about every 1 week. In some embodiments, the dose is AUC=4 and is administered once about every 2 week. In some embodiments, the dose is AUC=4 and is administered once about every 3 week. In some embodiments, the dose is AUC=4 and is administered once about every 4 week. In some embodiments, the dose is AUC=4.5 and is administered once about every 1 week. In some embodiments, the dose is AUC=4.5 and is administered once about every 2 week. In some embodiments, the dose is AUC=4.5 and is administered once about every 3 week. In some embodiments, the dose is AUC=4.5 and is administered once about every 4 week. In some embodiments, the dose is AUC=5 and is administered once about every 1 week. In some embodiments, the dose is AUC=5 and is administered once about every 2 week. In some embodiments, the dose is AUC=5 and is administered once about every 3 week. In some embodiments, the dose is AUC=5 and is administered once about every 4 week. In some embodiments, the dose is AUC=5.5 and is administered once about every 1 week. In some embodiments, the dose is AUC=5.5 and is administered once about every 2 week. In some embodiments, the dose is AUC=5.5 and is administered once about every 3 week. In some embodiments, the dose is AUC=5.5 and is administered once about every 4 week. In some embodiments, the dose is AUC=6 and is administered once about every 1 week. In some embodiments, the dose is AUC=6 and is administered once about every 2 week. In some embodiments, the dose is AUC=6 and is administered once about every 3 week. In some embodiments, the dose is AUC=6 and is administered once about every 4 week. In some embodiments, the dose is AUC=5 and is administered once about every 3 weeks (e.g., ±3 days). In some embodiments, the dose is AUC=5 and is administered once every 3 weeks. In some embodiments, the dose is AUC=5 and is administered once every 3 weeks and the platinum-based agent is carboplatin.

In one embodiment of the methods or uses or product for uses provided herein, a platinum-based agent as described herein is administered to the subject at flat dose ranging from about 50 mg to about 900 mg such as at a flat dose of about 50 mg or a flat dose of about 60 mg or a flat dose of about 70 mg or a flat dose of about 80 mg or a flat dose of about 90 mg or a flat dose of about 100 mg or a flat dose of about 120 mg or a flat dose of about 140 mg or a flat dose of about 160 mg or a flat dose of about 180 mg or a flat dose of about 200 mg or a flat dose of about 220 mg or a flat dose of about 240 mg or a flat dose of about 260 mg or a flat dose of about 280 mg or a flat dose of about 300 mg or a flat dose of about 320 mg or a flat dose of about 340 mg or a flat dose of about 360 mg or a flat dose of about 380 mg or a flat dose of about 400 mg or a flat dose of about 420 mg or a flat dose of about 440 mg or a flat dose of about 460 mg or a flat dose of about 480 mg or a flat dose of about 500 mg or a flat dose of about 520 mg or a flat dose of about 540 mg or a flat dose of about 560 mg or a flat dose of about 580 mg or a flat dose of about 600 mg or a flat dose of about 620 mg or a flat dose of about 640 mg or a flat dose of about 660 mg or a flat dose of about 680 mg or a flat dose of about 700 mg or a flat dose of about 720 mg or a flat dose of about 740 mg or a flat dose of about 750 mg or a flat dose of about 760 mg or a flat dose of about 780 mg or a flat dose of about 800 mg or a flat dose of about 820 mg or a flat dose of about 840 mg or a flat dose of about 860 mg or a flat dose of about 880 mg or a flat dose of about 900 mg. In some embodiments of the methods or uses or product for uses provided herein, a platinum-based agent as described herein is administered to the subject at flat dose ranging from 50 mg to 900 mg such as at a flat dose of 50 mg or a flat dose of 60 mg or a flat dose of 70 mg or a flat dose of 80 mg or a flat dose of 90 mg or a flat dose of 100 mg or a flat dose of 120 mg or a flat dose of 140 mg or a flat dose of 160 mg or a flat dose of 180 mg or a flat dose of 200 mg or a flat dose of 220 mg or a flat dose of 240 mg or a flat dose of 260 mg or a flat dose of 280 mg or a flat dose of 300 mg or a flat dose of 320 mg or a flat dose of 340 mg or a flat dose of 360 mg or a flat dose of 380 mg or a flat dose of 400 mg or a flat dose of 420 mg or a flat dose of 440 mg or a flat dose of 460 mg or a flat dose of 480 mg or a flat dose of 500 mg or a flat dose of 520 mg or a flat dose of 540 mg or a flat dose of 560 mg or a flat dose of 580 mg or a flat dose of 600 mg or a flat dose of 620 mg or a flat dose of 640 mg or a flat dose of 660 mg or a flat dose of 680 mg or a flat dose of 700 mg or a flat dose of 720 mg or a flat dose of 740 mg or a flat dose of 750 mg or a flat dose of 760 mg or a flat dose of 780 mg or a flat dose of 800 mg or a flat dose of 820 mg or a flat dose of 840 mg or a flat dose of 860 mg or a flat dose of 880 mg or a flat dose of 900 mg. In some embodiments, the flat dose is 750 mg. In some embodiments, the flat dose is 750 mg and the platinum-based agent is carboplatin. In some embodiments, the flat dose is about 600 mg and is administered once about every 1 week. In some embodiments, the flat dose is about 600 mg and is administered once about every 2 weeks. In some embodiments, the flat dose is about 600 mg and is administered once about every 3 weeks. In some embodiments, the flat dose is about 600 mg and is administered once about every 4 weeks. In some embodiments, the flat dose is about 750 mg and is administered once about every 1 week. In some embodiments, the flat dose is about 750 mg and is administered once about every 2 weeks. In some embodiments, the flat dose is about 750 mg and is administered once about every 3 weeks. In some embodiments, the flat dose is about 750 mg and is administered once about every 4 weeks. In some embodiments, the flat dose is 600 mg and is administered once about every 1 week. In some embodiments, the flat dose is 600 mg and is administered once about every 2 weeks. In some embodiments, the flat dose is 600 mg and is administered once about every 3 weeks. In some embodiments, the flat dose is 600 mg and is administered once about every 4 weeks. In some embodiments, the flat dose is 750 mg and is administered once about every 1 week. In some embodiments, the flat dose is 750 mg and is administered once about every 2 weeks. In some embodiments, the flat dose is 750 mg and is administered once about every 3 weeks. In some embodiments, the flat dose is 750 mg and is administered once about every 4 weeks. In some embodiments, the flat dose is 750 mg and is administered once about every 3 weeks (e.g., ±3 days). In some embodiments, the flat dose is 750 mg and is administered once every 3 weeks. In some embodiments, the flat dose is 750 mg and is administered once every 3 weeks and the platinum-based agent is carboplatin.

In some embodiments of the methods or uses or product for uses provided herein, a platinum-based agent as described herein and an anti-TF antibody-drug conjugate or antigen-binding fragment thereof as described herein are administered to the subject at a fixed dose. In some embodiments, the fixed dose is based on the amount (e.g., mg) of the agents. In certain embodiments, the fixed dose is based on the concentration (e.g., mg/ml) of the agents. In some embodiments, the ratio of the amount (e.g., mg) of the platinum-based agent to the amount (e.g., mg) of the anti-TF antibody-drug conjugate or antigen-binding fragment thereof is about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1. In some embodiments, the ratio of the concentration (e.g., mg/ml) of the platinum-based agent to the concentration (e.g., mg/ml) of the anti-TF antibody-drug conjugate or antigen-binding fragment thereof is about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1. In some embodiments, the ratio of the amount (e.g., mg) of the platinum-based agent to the amount (e.g., mg) of the anti-TF antibody-drug conjugate or antigen-binding fragment thereof is 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100, 1:120, 1:140, 1:160, 1:180, 1:200, 200:1, 180:1, 160:1, 140:1, 120:1, 100:1, 90:1, 80:1, 70:1, 60:1, 50:1, 40:1, 30:1, 20:1, 15:1, 10:1, 9:1, 8:1, 7:1, 6:1, 5:1, 4:1, 3:1, or 2:1. In some embodiments, the ratio of the concentration (e.g., mg/ml) of the platinum-based agent to the concentration (e.g., mg/ml) of the anti-TF antibody-drug conjugate or antigen-binding fragment thereof is 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90, 1:100, 1:120, 1:140, 1:160, 1:180, 1:200, 200:1, 180:1, 160:1, 140:1, 120:1, 100:1, 90:1, 80:1, 70:1, 60:1, 50:1, 40:1, 30:1, 20:1, 15:1, 10:1, 9:1, 8:1, 7:1, 6:1, 5:1, 4:1, 3:1, or 2:1.

In some embodiments, the dose of the anti-TF antibody-drug conjugate is 2.0 mg/kg and is administered once about every 3 weeks (e.g., ±3 days) and the dose of the platinum-based agent is AUC=5 and is administered once about every 3 weeks (e.g., ±3 days). In some embodiments, the dose of the anti-TF antibody-drug conjugate is 2.0 mg/kg and is administered once every 3 weeks and the dose of the platinum-based agent is AUC=5 and is administered once every 3 weeks. In some embodiments, the dose of the anti-TF antibody-drug conjugate is 2.0 mg/kg and is administered once every 3 weeks and the antibody-drug conjugate is tisotumab vedotin and the dose of the platinum-based agent is AUC=5 and is administered once every 3 weeks and the platinum-based agent is carboplatin.

In some embodiments, the dose of the anti-TF antibody-drug conjugate is 1.3 mg/kg and is administered once about every 3 weeks (e.g., ±3 days) and the dose of the platinum-based agent is AUC=5 and is administered once about every 3 weeks (e.g., ±3 days). In some embodiments, the dose of the anti-TF antibody-drug conjugate is 1.3 mg/kg and is administered once every 3 weeks and the dose of the platinum-based agent is AUC=5 and is administered once every 3 weeks. In some embodiments, the dose of the anti-TF antibody-drug conjugate is 1.3 mg/kg and is administered once every 3 weeks and the antibody-drug conjugate is tisotumab vedotin and the dose of the platinum-based agent is AUC=5 and is administered once every 3 weeks and the platinum-based agent is carboplatin.

In some embodiments, an anti-TF antibody-drug conjugate or antigen-binding fragment thereof as described herein and a platinum-based agent as described herein are coadministered. In some embodiments the coadministration is simultaneous or sequential. In some embodiments, an anti-TF antibody-drug conjugate as described herein is administered simultaneously with a platinum-based agent as described herein. In some embodiments, simultaneous means that the anti-TF antibody-drug conjugate and the platinum-based agent are administered to the subject less than one hour apart, such as less than about 30 minutes apart, less than about 15 minutes apart, less than about 10 minutes apart or less than about 5 minutes apart. In some embodiments, an anti-TF antibody-drug conjugate as described herein is administered sequentially with a platinum-based agent as described herein. In some embodiments, sequential administration means that the anti-TF antibody-drug conjugate and the platinum-based agent are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart.

In some embodiments, a method of treatment or use or product for use described herein further comprises the administration of one or more additional therapeutic agents. In some embodiments, the one or more additional therapeutic agents are administered simultaneously with an anti-TF antibody-drug conjugate or antigen-binding fragment thereof as described herein, such as tisotumab vedotin, and a platinum-based agent as described herein, such as carboplatin. In some embodiments, the one or more additional therapeutic agents and an anti-TF antibody-drug conjugate or antigen-binding fragment thereof as described herein, such as tisotumab vedotin, and a platinum-based agent as described herein, such as carboplatin, are administered sequentially.

E. Treatment Outcome

In one aspect, a method of treating cancer with an anti-TF antibody-drug conjugate or antigen-binding fragment thereof as described herein, such as e.g., tisotumab vedotin, and a platinum-based agent as described herein, such as e.g., carboplatin, results in an improvement in one or more therapeutic effects in the subject after administration of the antibody-drug conjugate and/or the platinum-based agent relative to a baseline. In some embodiments, the one or more therapeutic effects is the size of the tumor derived from the cancer (e.g., bladder cancer or cervical cancer), the objective response rate, the duration of response, the time to response, progression free survival, overall survival, or any combination thereof. In one embodiment, the one or more therapeutic effects is the size of the tumor derived from the cancer. In one embodiment, the one or more therapeutic effects is decreased tumor size. In one embodiment, the one or more therapeutic effects is stable disease. In one embodiment, the one or more therapeutic effects is partial response. In one embodiment, the one or more therapeutic effects is complete response. In one embodiment, the one or more therapeutic effects is the objective response rate. In one embodiment, the one or more therapeutic effects is the duration of response. In one embodiment, the one or more therapeutic effects is the time to response. In one embodiment, the one or more therapeutic effects is progression free survival. In one embodiment, the one or more therapeutic effects is overall survival. In one embodiment, the one or more therapeutic effects is cancer regression.

In one embodiment of the methods or uses or product for uses provided herein, response to treatment with an anti-TF antibody-drug conjugate or antigen-binding fragment thereof as described herein, such as e.g., tisotumab vedotin, and a platinum-based agent as described herein, such as e.g., carboplatin, may include the following criteria (RECIST Criteria 1.1):

| | Category | Criteria |
|---|---|---|
| Based on target lesions | Complete Response (CR) | Disappearance of all target lesions. Any pathological lymph nodes must have reduction in short axis to <10 mm. |
| | Partial | ≥30% decrease in the sum of the longest |

| Category | | Criteria |
|---|---|---|
| | Response (PR) | diameter (LD) of target lesions, taking as reference the baseline sum of LDs. |
| | Stable Disease (SD) | Neither sufficient shrinkage to qualify for PR nor sufficient increase to qualify for PD, taking as reference the smallest sum of LDs while in trial. |
| | Progressive Disease (PD) | ≥20% (and ≥5 mm) increase in the sum of the LDs of target lesions, taking as reference the smallest sum of the target LDs recorded while in trial or the appearance of one or more new lesions. |
| Based on non-target lesions | CR | Disappearance of all non-target lesions and normalization of tumor marker level. All lymph nodes must be non-pathological in size (<10 mm short axis). |
| | SD | Persistence of one or more non-target lesion(s) or/and maintenance of tumor marker level above the normal limits. |
| | PD | Appearance of one or more new lesions and/or unequivocal progression of existing non-target lesions. |

In one embodiment of the methods or uses or product for uses provided herein, the effectiveness of treatment with an anti-TF antibody-drug conjugate or antigen-binding fragment thereof described herein, such as e.g., tisotumab vedotin, and a platinum-based agent described herein, such as e.g., carboplatin, is assessed by measuring the objective response rate. In some embodiments, the objective response rate is the proportion of patients with tumor size reduction of a predefined amount and for a minimum period of time. In some embodiments the objective response rate is based upon RECIST v1.1. In one embodiment, the objective response rate is at least about 20%, at least about 25%, at least about 30%, at least about 35%, at least about 40%, at least about 45%, at least about 50%, at least about 60%, at least about 70%, or at least about 80%. In one embodiment, the objective response rate is at least about 20%-80%. In one embodiment, the objective response rate is at least about 30%-80%. In one embodiment, the objective response rate is at least about 40%-80%. In one embodiment, the objective response rate is at least about 50%-80%. In one embodiment, the objective response rate is at least about 60%-80%. In one embodiment, the objective response rate is at least about 70%-80%. In one embodiment, the objective response rate is at least about 80%. In one embodiment, the objective response rate is at least about 85%. In one embodiment, the objective response rate is at least about 90%. In one embodiment, the objective response rate is at least about 95%. In one embodiment, the objective response rate is at least about 98%. In one embodiment, the objective response rate is at least about 99%. In one embodiment, the objective response rate is at least 20%, at least 25%, at least 30%, at least 35%, at least 40%, at least 45%, at least 50%, at least 60%, at least 70%, or at least 80%. In one embodiment, the objective response rate is at least 20%-80%. In one embodiment, the objective response rate is at least 30%-80%. In one embodiment, the objective response rate is at least 40%-80%. In one embodiment, the objective response rate is at least 50%-80%. In one embodiment, the objective response rate is at least 60%-80%. In one embodiment, the objective response rate is at least 70%-80%. In one embodiment, the objective response rate is at least 80%. In one embodiment, the objective response rate is at least 85%. In one embodiment, the objective response rate is at least 90%. In one embodiment, the objective response rate is at least 95%. In one embodiment, the objective response rate is at least 98%. In one embodiment, the objective response rate is at least 99%. In one embodiment, the objective response rate is 100%.

In one embodiment of the methods or uses or product for uses provided herein, response to treatment with an anti-TF antibody-drug conjugate or antigen-binding fragment thereof described herein, such as e.g., tisotumab vedotin, and a platinum-based agent described herein, such as e.g., carboplatin, is assessed by measuring the size of a tumor derived from the cancer (e.g., bladder cancer or cervical cancer). In one embodiment, the size of a tumor derived from the cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the anti-TF antibody-drug conjugate and/or the platinum-based agent. In one embodiment, the size of a tumor derived from the cancer is reduced by at least about 10%-80%. In one embodiment, the size of a tumor derived from the cancer is reduced by at least about 20%-80%. In one embodiment, the size of a tumor derived from the cancer is reduced by at least about 30%-80%. In one embodiment, the size of a tumor derived from the cancer is reduced by at least about 40%-80%. In one embodiment, the size of a tumor derived from the cancer is reduced by at least about 50%-80%. In one embodiment, the size of a tumor derived from the cancer is reduced by at least about 60%-80%. In one embodiment, the size of a tumor derived from the cancer is reduced by at least about 70%-80%. In one embodiment, the size of a tumor derived from the cancer is reduced by at least about 80%. In one embodiment, the size of a tumor derived from the cancer is reduced by at least about 85%. In one embodiment, the size of a tumor derived from the cancer is reduced by at least about 90%. In one embodiment, the size of a tumor derived from the cancer is reduced by at least about 95%. In one embodiment, the size of a tumor derived from the cancer is reduced by at least about 98%. In one embodiment, the size of a tumor derived from the cancer is reduced by at least about 99%. In one embodiment, the size of a tumor derived from the cancer is reduced by at least 10%, at least 15%, at least 20%, at least 25%, at least 30%, at least 35%, at least 40%, at least 45%, at least 50%, at least 60%, at least 70%, or at least 80% relative to the size of the tumor derived from the cancer before administration of the anti-TF antibody-drug conjugate and/or the platinum-based agent. In one embodiment, the size of a tumor derived from the cancer is reduced by at least 10%-80%. In one embodiment, the size of a tumor derived from the cancer is reduced by at least 20%-80%. In one embodiment, the size of a tumor derived from the cancer is reduced by at least 30%-80%. In one embodiment, the size of a tumor derived from the cancer is reduced by at least 40%-80%. In one embodiment, the size of a tumor derived from the cancer is reduced by at least 50%-80%. In one embodiment, the size of a tumor derived from the cancer is reduced by at least 60%-80%. In one embodiment, the size of a tumor derived from the cancer is reduced by at least 70%-80%. In one embodiment, the size of a tumor derived from the cancer is reduced by at least 80%. In one embodiment, the size of a tumor derived from the cancer is reduced by at least 85%. In one embodiment, the size of a tumor derived from the cancer is reduced by at least 90%. In one embodiment, the size of a tumor derived from the cancer is reduced by at least 95%. In one embodiment, the size of a tumor derived from the cancer is reduced by at least 98%. In one embodiment, the size of a tumor derived from the cancer is reduced by at least 99%. In one embodiment, the size of a tumor derived from the cancer is reduced by 100%. In one embodiment, the size of a tumor derived from the cancer is measured by magnetic resonance imaging (MRI). In one embodiment, the size of a tumor derived from the cancer is measured by computed tomography (CT). In some embodiments, the size of a tumor derived from a cervical cancer is measured by pelvic examination. See Choi et al., 2008, *J Gynecol. Oncol.* 19(3):205. In some embodiments, the size of a tumor derived from a bladder cancer is measured by cystoscopy or cytology. See US 2017/0181988. In some embodiments, the size of the tumor derived from the cancer is reduced relative to the size of the tumor before administration of the anti-TF antibody drug conjugate and the platinum-based agent. In some embodiments, the size of the tumor derived from the cancer is reduced relative to the size of the tumor before administration of the anti-TF antibody drug conjugate. In some embodiments, the size of the tumor derived from the cancer is reduced relative to the size of the tumor before administration of the platinum-based agent.

In one embodiment of the methods or uses or product for uses provided described herein, response to treatment with an antibody-drug conjugate or antigen-binding fragment thereof described herein, such as e.g., tisotumab vedotin, and a platinum-based agent described herein, such as e.g., carboplatin, promotes regression of a tumor derived from the cancer (e.g., bladder cancer or cervical cancer). In one embodiment, a tumor derived from the cancer regresses by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the anti-TF antibody-drug conjugate and/or platinum-based agent. In one embodiment, a tumor derived from the cancer regresses by at least about 10% to about 80%. In one embodiment, a tumor derived from the cancer regresses by at least about 20% to about 80%. In one embodiment, a tumor derived from the cancer regresses by at least about 30% to about 80%. In one embodiment, a tumor derived from the cancer regresses by at least about 40% to about 80%. In one embodiment, a tumor derived from the cancer regresses by at least about 50% to about 80%. In one embodiment, a tumor derived from the cancer regresses by at least about 60% to about 80%. In one embodiment, a tumor derived from the cancer regresses by at least about 70% to about 80%. In one embodiment, a tumor derived from the cancer regresses by at least about 80%. In one embodiment, a tumor derived from the cancer regresses by at least about 85%. In one embodiment, a tumor derived from the cancer regresses by at least about 90%. In one embodiment, a tumor derived from the cancer regresses by at least about 95%. In one embodiment, a tumor derived from the cancer regresses by at least about 98%. In one embodiment, a tumor derived from the cancer regresses by at least about 99%. In one embodiment, a tumor derived from the cancer regresses by at least 10%, at least 15%, at least 20%, at least 25%, at least 30%, at least 35%, at least 40%, at least 45%, at least 50%, at least 60%, at least 70%, or at least 80% relative to the size of the tumor derived from the cancer before administration of the anti-TF antibody-drug conjugate and/or platinum-based agent. In one embodiment, a tumor derived from the cancer regresses by at least 10% to 80%. In one embodiment, a tumor derived from the cancer regresses by at least 20% to 80%. In one embodiment, a tumor derived from the cancer regresses by at least 30% to 80%. In one embodiment, a tumor derived from the cancer regresses by at least 40% to 80%. In one embodiment, a tumor derived from the cancer regresses by at least 50% to 80%. In one embodiment, a tumor derived from the cancer regresses by at least 60% to 80%. In one embodiment, a tumor derived from the cancer regresses by at least 70% to 80%. In one embodiment, a tumor derived from the cancer regresses by at least 80%. In one embodiment, a tumor derived from the cancer regresses by at least 85%. In one embodiment, a tumor derived from the cancer regresses by at least 90%. In one embodiment, a tumor derived from the cancer regresses by at least 95%. In one embodiment, a tumor derived from the cancer regresses by at least 98%. In one embodiment, a tumor derived from the cancer regresses by at least 99%. In one embodiment, a tumor derived from the cancer regresses by 100%. In one embodiment, regression of a tumor is determined by measuring the size of the tumor by magnetic resonance imaging (MRI). In one embodiment, regression of a tumor is determined by measuring the size of the tumor by computed tomography (CT). In some embodiments, regression of a tumor is determined by measuring the size of the tumor by pelvic examination. See Choi et al., 2008, 1 Gynecol. Oncol. 19(3):205. In some embodiments, the size of a tumor derived from a bladder cancer is measured by cystoscopy or cytology. See US 2017/0181988. In some embodiments, the tumor derived from the cancer regresses relative to the size of the tumor before administration of the anti-TF antibody drug conjugate and the platinum-based agent. In some embodiments, the tumor derived from the cancer regresses relative to the size of the tumor before administration of the anti-TF antibody drug conjugate. In some embodiments, the tumor derived from the cancer regresses relative to the size of the tumor before administration of the platinum-based agent.

In one embodiment of the methods or uses or product for uses described herein, response to treatment with an anti-TF antibody-drug conjugate or antigen-binding fragment thereof described herein, such as e.g., tisotumab vedotin, and a platinum-based agent described herein, such as e.g., carboplatin, is assessed by measuring the time of progression free survival after administration of the anti-TF antibody-drug conjugate and/or the platinum-based agent. In some embodiments, the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate and/or the platinum-based agent. In some embodiments, the subject exhibits progression-free survival of at least about 6 months after administration of the anti-TF antibody-drug conjugate and/or the platinum-based agent. In some embodiments, the subject exhibits progression-free survival of at least about one year after administration of the anti-TF antibody-drug conjugate and/or the platinum-based agent. In some embodiments, the subject exhibits progression-free survival of at least about two years after administration of the anti-TF antibody-drug conjugate and/or the platinum-based agent. In some embodiments, the subject exhibits progression-free survival of at least about three years after administration of the anti-TF antibody-drug conjugate and/or the platinum-based agent. In some embodiments, the subject exhibits progression-free survival of at least about four years after administration of the anti-TF antibody-drug conjugate and/or the platinum-based agent. In some embodiments, the subject exhibits progression-free survival of at least about five years after administration of the anti-TF antibody-drug conjugate and/or the platinum-based agent. In some embodiments, the subject exhibits progression-free survival of at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-TF antibody-drug conjugate and/or the platinum-based agent. In some embodiments, the subject exhibits progression-free survival of at least 6 months after administration of the anti-TF antibody-drug conjugate and/or the platinum-based agent. In some embodiments, the subject exhibits progression-free survival of at least one year after administration of the anti-TF antibody-drug conjugate and/or the platinum-based agent. In some embodiments, the subject exhibits progression-free survival of at least two years after administration of the anti-TF antibody-drug conjugate and/or the platinum-based agent. In some embodiments, the subject exhibits progression-free survival of at least three years after administration of the anti-TF antibody-drug conjugate and/or the platinum-based agent. In some embodiments, the subject exhibits progression-free survival of at least four years after administration of the anti-TF antibody-drug conjugate and/or the platinum-based agent. In some embodiments, the subject exhibits progression-free survival of at least five years after administration of the anti-TF antibody-drug conjugate and/or the platinum-based agent. In some embodiments, response to treatment is assessed by measuring the time of progression free survival after administration of the anti-TF antibody-drug conjugate and the platinum-based agent. In some embodiments, response to treatment is assessed by measuring the time of progression free survival after administration of the anti-TF antibody-drug conjugate. In some embodiments, response to treatment is assessed by measuring the time of progression free survival after administration of the platinum-based agent.

In one embodiment of the methods or uses or product for uses described herein, response to treatment with an anti-TF antibody-drug conjugate or antigen-binding fragment thereof described herein, such as e.g., tisotumab vedotin, and a platinum-based agent described herein, such as e.g., carboplatin, is assessed by measuring the time of overall survival after administration of the anti-TF antibody-drug conjugate and/or the platinum-based agent. In some embodiments, the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate and/or the platinum-based agent. In some embodiments, the subject exhibits overall survival of at least about 6 months after administration of the anti-TF antibody-drug conjugate and/or the platinum-based agent. In some embodiments, the subject exhibits overall survival of at least about one year after administration of the anti-TF antibody-drug conjugate and/or the platinum-based agent. In some embodiments, the subject exhibits overall survival of at least about two years after administration of the anti-TF antibody-drug conjugate and/or the platinum-based agent. In some embodiments, the subject exhibits overall survival of at least about three years after administration of the anti-TF antibody-drug conjugate and/or the platinum-based agent. In some embodiments, the subject exhibits overall survival of at least about four years after administration of the anti-TF antibody-drug conjugate and/or the platinum-based agent. In some embodiments, the subject exhibits overall survival of at least about five years after administration of the anti-TF antibody-drug conjugate and/or the platinum-based agent. In some embodiments, the subject exhibits overall survival of at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-TF antibody-drug conjugate and/or the platinum-based agent. In some embodiments, the subject exhibits overall survival of at least 6 months after administration of the anti-TF antibody-drug conjugate and/or the platinum-based agent. In some embodiments, the subject exhibits overall survival of at least one year after administration of the anti-TF antibody-drug conjugate and/or the platinum-based agent. In some embodiments, the subject exhibits overall survival of at least two years after administration of the anti-TF antibody-drug conjugate and/or the platinum-based agent. In some embodiments, the subject exhibits overall survival of at least three years after administration of the anti-TF antibody-drug conjugate and/or the platinum-based agent. In some embodiments, the subject exhibits overall survival of at least four years after administration of the anti-TF antibody-drug conjugate and/or the platinum-based agent. In some embodiments, the subject exhibits overall survival of at least five years after administration of the anti-TF antibody-drug conjugate and/or the platinum-based agent. In some embodiments, response to treatment is assessed by measuring the time of overall survival after administration of the anti-TF antibody-drug conjugate and the platinum-based agent. In some embodiments, response to treatment is assessed by measuring the time of overall survival after administration of the anti-TF antibody-drug conjugate. In some embodiments, response to treatment is assessed by measuring the time of overall survival after administration of the platinum-based agent.

In one embodiment of the methods or uses or product for uses described herein, response to treatment with an anti-TF antibody-drug conjugate or antigen-binding fragment thereof described herein, such as e.g., tisotumab vedotin, and a platinum-based agent described herein, such as e.g., carboplatin, is assessed by measuring the duration of response to the anti-TF antibody-drug conjugate and the platinum-based agent after administration of the anti-TF antibody-drug conjugate and/or the platinum-based agent. In some embodiments, the duration of response to the anti-TF antibody-drug conjugate and the platinum-based agent is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the anti-TF antibody-drug conjugate and/or the platinum-based agent. In some embodiments, the duration of response to the anti-TF antibody-drug conjugate and the platinum-based agent is at least about 6 months after administration of the antibody-drug conjugate and/or the platinum-based agent. In some embodiments, the duration of response to the anti-TF antibody-drug conjugate and the platinum-based agent is at least about one year after administration of the antibody-drug conjugate and/or the platinum-based agent. In some embodiments, the duration of response to the anti-TF antibody-drug conjugate and the platinum-based agent is at least about two years after administration of the antibody-drug conjugate and/or the platinum-based agent. In some embodiments, the duration of response to the anti-TF antibody-drug conjugate and the platinum-based agent is at least about three years after administration of the antibody-drug conjugate and/or the platinum-based agent. In some embodiments, the duration of response to the anti-TF antibody-drug conjugate and the platinum-based agent is at least about four years after administration of the antibody-drug conjugate. In some embodiments, the duration of response to the anti-TF antibody-drug conjugate and the platinum-based agent is at least about five years after administration of the antibody-drug conjugate and/or the platinum-based agent. In some embodiments, the duration of response to the anti-TF antibody-drug conjugate and the platinum-based agent is at least 1 month, at least 2 months, at least 3 months, at least 4 months, at least 5 months, at least 6 months, at least 7 months, at least 8 months, at least 9 months, at least 10 months, at least 11 months, at least 12 months, at least eighteen months, at least two years, at least three years, at least four years, or at least five years after administration of the anti-TF antibody-drug conjugate and/or the platinum-based agent. In some embodiments, the duration of response to the anti-TF antibody-drug conjugate and the platinum-based agent is at least 6 months after administration of the antibody-drug conjugate and/or the platinum-based agent. In some embodiments, the duration of response to the anti-TF antibody-drug conjugate and the platinum-based agent is at least one year after administration of the antibody-drug conjugate and/or the platinum-based agent. In some embodiments, the duration of response to the anti-TF antibody-drug conjugate and the platinum-based agent is at least two years after administration of the antibody-drug conjugate and/or the platinum-based agent. In some embodiments, the duration of response to the anti-TF antibody-drug conjugate and the platinum-based agent is at least three years after administration of the antibody-drug conjugate and/or the platinum-based agent. In some embodiments, the duration of response to the anti-TF antibody-drug conjugate and the platinum-based agent is at least four years after administration of the antibody-drug conjugate. In some embodiments, the duration of response to the anti-TF antibody-drug conjugate and the platinum-based agent is at least five years after administration of the antibody-drug conjugate and/or the platinum-based agent. In some embodiments, the duration of response is measured after administration of the anti-TF antibody drug conjugate and the platinum-based agent. In some embodiments, the duration of response is measured after administration of the anti-TF antibody drug conjugate. In some embodiments, the duration of response is measured after administration of the platinum-based agent.

F. Adverse Events

In one aspect, a method of treating cancer (e.g., bladder cancer or cervical cancer) with an anti-TF antibody-drug conjugates or antigen-binding fragments thereof described herein, such as e.g., tisotumab vedotin, and a platinum-based agent described herein, such as e.g., carboplatin, results in the subject developing one or more adverse events. In some embodiments, the subject is administered an additional therapeutic agent to eliminate or reduce the severity of the adverse event. In some embodiments, the one or more adverse events the subject develops is increased bleeding, hemorrhage, liver function abnormality (e.g., elevated liver enzymes), mucositis, neutropenia, febrile neutropenia, peripheral neuropathy, decreased platelet count, vomiting, neuropathy, conjunctivitis, keratitis, conjunctival ulceration, symblepharon, infusion-related reactions, or general health deterioration, or any combination thereof. In some embodiments, the one or more adverse events the subject develops is anemia, abdominal pain, hemorrhage, hypokalemia, hyponatremia, epistaxis, fatigue, nausea, alopecia, conjunctivitis, keratitis, conjunctival ulceration, constipation, decreased appetite, diarrhea, vomiting, neutropenia, decreased platelet count, peripheral neuropathy, or general physical health deterioration, or any combination thereof. In some embodiments, the one or more adverse events is a grade 1 or greater adverse event. In some embodiments, the one or more adverse events is a grade 2 or greater adverse event. In some embodiments, the one or more adverse events is a grade 3 or greater adverse event. In some embodiments, the one or more adverse events is a grade 1 adverse event. In some embodiments, the one or more adverse events is a grade 2 adverse event. In some embodiments, the one or more adverse events is a grade 3 adverse event. In some embodiments, the one or more adverse events is a grade 4 adverse event. In some embodiments, the one or more adverse events is a serious adverse event. In some embodiments, the one or more adverse events is conjunctivitis, conjunctival ulceration, and/or keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis, conjunctival ulceration, and keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis and keratitis and the additional therapeutic agent is a preservative-free lubricating eye drop, an ocular vasoconstrictor, antibiotic, a steroid eye drop, or any combination thereof. In some embodiments, the one or more adverse events is conjunctivitis and the additional therapeutic agent is a preservative-free lubricating eye drop, an ocular vasoconstrictor, antibiotic, a steroid eye drop, or any combination thereof. In some embodiments, the one or more adverse events is keratitis and the additional therapeutic agent is a preservative-free lubricating eye drop, an ocular vasoconstrictor, antibiotic, a steroid eye drop, or any combination thereof. In some of any of the embodiments herein, the subject is administered a treatment with the additional therapeutic agent to eliminate or reduce the severity of the adverse event (e.g., conjunctivitis, conjunctival ulceration, and/or keratitis). In some embodiments, the treatment is eye cooling pads (e.g. THERA PEARL Eye Mask or similar). In some embodiments, the one or more adverse events is a recurrent infusion related reaction and the additional therapeutic agent is an antihistamine, acetaminophen and/or a corticosteroid. In some embodiments, the one or more adverse events is neutropenia and the additional therapeutic agent is growth factor support (G-CSF). In some embodiments, the one or more adverse events is hyperthyroidism and the additional agent is a non-selective beta-blockers (e.g., propranolol) or thionamides. In some embodiments, the one or more adverse events is hypothyroidism and the additional agent is a thyroid replacement hormone (e.g., levothyroxine or liothyronine).

In one aspect, the subject treated with an anti-TF antibody-drug conjugates or antigen-binding fragments thereof described herein, such as e.g., tisotumab vedotin, and a platinum-based agent described herein, such as e.g., carboplatin, is at risk of developing one or more adverse events. In some embodiments, the subject is administered an additional therapeutic agent to prevent the development of the adverse event or to reduce the severity of the adverse event. In some embodiments, the one or more adverse events the subject is at risk of developing is increased bleeding, hemorrhage, liver function abnormality (e.g., elevated liver enzymes), mucositis, neutropenia, febrile neutropenia, peripheral neuropathy, decreased platelet count, vomiting, neuropathy, conjunctivitis, keratitis, conjunctival ulceration, symblepharon, infusion-related reactions, or general health deterioration, or any combination thereof. In some embodiments, the one or more adverse events the subject is at risk of developing is anemia, abdominal pain, hemorrhage, hypokalemia, hyponatremia, epistaxis, fatigue, nausea, alopecia, conjunctivitis, keratitis, conjunctival ulceration, constipation, decreased appetite, diarrhea, vomiting, neutropenia, decreased platelet count, peripheral neuropathy, or general physical health deterioration, or any combination thereof. In some embodiments, the one or more adverse events is a grade 1 or greater adverse event. In some embodiments, the one or more adverse events is a grade 2 or greater adverse event. In some embodiments, the one or more adverse events is a grade 3 or greater adverse event. In some embodiments, the one or more adverse events is a grade 1 adverse event. In some embodiments, the one or more adverse events is a grade 2 adverse event. In some embodiments, the one or more adverse events is a grade 3 adverse event. In some embodiments, the one or more adverse events is a grade 4 adverse event. In some embodiments, the one or more adverse events is a serious adverse event. In some embodiments, the one or more adverse events is conjunctivitis, conjunctival ulceration, and/or keratitis and the additional agent is a preservative-free lubricating eye drop, an ocular vasoconstrictor, antibiotic, a steroid eye drop, or any combination thereof. In some embodiments, the one or more adverse events is conjunctivitis and keratitis and the additional agent is a preservative-free lubricating eye drop, an ocular vasoconstrictor, antibiotic, a steroid eye drop, or any combination thereof. In some embodiments, the one or more adverse events is conjunctivitis and the additional agent is a preservative-free lubricating eye drop, an ocular vasoconstrictor, antibiotic, a steroid eye drop, or any combination thereof. In some embodiments, the one or more adverse events is keratitis and the additional agent is a preservative-free lubricating eye drop, an ocular vasoconstrictor, antibiotic, a steroid eye drop, or any combination thereof. In some of any of the embodiments herein, the subject is administered a treatment with the additional therapeutic agent to prevent the development of the adverse event or to reduce the severity of the adverse event (e.g., conjunctivitis, conjunctival ulceration, and/or keratitis). In some embodiments, the treatment is eye cooling pads (e.g. THERA PEARL Eye Mask or similar). In some embodiments, the one or more adverse events is a recurrent infusion related reaction and the additional agent is an antihistamine, acetaminophen and/or a corticosteroid. In some embodiments, the one or more adverse events is neutropenia and the additional agent is growth factor support (G-CSF). In some embodiments, the one or more adverse events is hyperthyroidism and the additional agent is a non-selective beta-blockers (e.g., propranolol) or thionamides. In some embodiments, the one or more adverse events is hypothyroidism and the additional agent is a thyroid replacement hormone (e.g., levothyroxine or liothyronine).

IV. Compositions

In some aspects, also provided herein are compositions (e.g., pharmaceutical compositions and therapeutic formulations) comprising any of the anti-TF antibody-drug conjugates or antigen-binding fragments thereof described herein, such as e.g., tisotumab vedotin, and/or the platinum-based agents described herein, such as e.g., carboplatin.

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wilkins, Pub., Gennaro Ed., Philadelphia, Pa. 2000).

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intramolecular interactions. Tonicity agents can be present in any amount between about 0.1% to about 25% by weight or between about 1% to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, a-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

Formulations comprising an anti-TF antibody-conjugate described herein for use in methods of treatment provided herein are described in WO2015/075201. In some embodiments, an anti-TF antibody-drug conjugate described herein is in a formulation comprising the anti-TF antibody drug conjugate, histidine, sucrose, and D-mannitol, wherein the formulation has a pH of about 6.0. In some embodiments, an anti-TF antibody-drug conjugate described herein is in a formulation comprising the anti-TF antibody drug conjugate at a concentration of about 10 mg/ml, histidine at a concentration of about 30 mM, sucrose at a concentration of about 88 mM, D-mannitol at a concentration of about 165 mM, wherein the formulation has a pH of about 6.0. In some embodiments, an anti-TF antibody-drug conjugate described herein is in a formulation comprising the anti-TF antibody drug conjugate at a concentration of 10 mg/ml, histidine at a concentration of 30 mM, sucrose at a concentration of 88 mM, D-mannitol at a concentration of 165 mM, wherein the formulation has a pH of 6.0. In some embodiments, the formulation comprises tisotumab vedotin at a concentration of 10 mg/ml, histidine at a concentration of 30 mM, sucrose at a concentration of 88 mM, D-mannitol at a concentration of 165 mM, wherein the formulation has a pH of 6.0.

In some embodiments provided herein, a formulation comprising the anti-TF antibody-conjugate described herein does not comprise a surfactant (i.e., is free of surfactant).

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The invention provides compositions comprising a population of anti-TF antibody-drug conjugates or antigen-binding fragments thereof as described herein for use in a method of treating cervical cancer as described herein. In some aspects, provided herein are compositions comprising a population of antibody-drug conjugates, wherein the antibody-drug conjugates comprise a linker attached to MMAE, wherein the antibody-drug conjugate has the following structure:

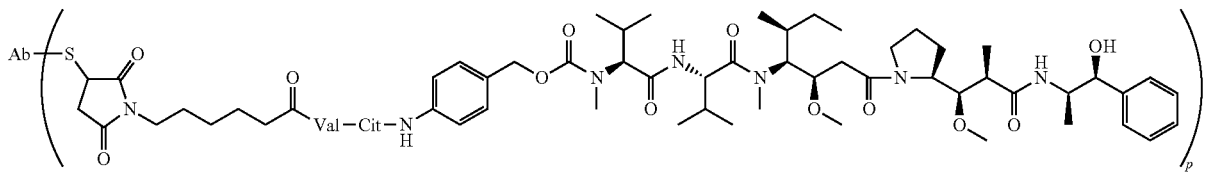

Ab-MC-vc-PAB-MMAE wherein p denotes a number from 1 to 8, e.g., 1, 2, 3, 4, 5, 6, 7 or 8, S represents a sulphydryl residue of the anti-TF antibody or antigen-binding fragment thereof, and Ab designates the anti-TF antibody or antigen-binding fragment thereof as described herein, such as tisotumab. In some embodiments, p denotes a number from 3 to 5. In some embodiments, the average value of p in the composition is about 4. In some embodiments, the population is a mixed population of antibody-drug conjugates in which p varies from 1 to 8 for each antibody-drug conjugate. In some embodiments, the population is a homogenous population of antibody-drug conjugates with each antibody-drug conjugate having the same value for p.

In some embodiments, a composition comprising an anti-TF antibody-drug conjugate or antigen-binding fragment thereof as described herein, such as e.g., tisotumab vedotin, is coadministered with a composition comprising a platinum-based agent as described herein, such as e.g., tisotumab vedotin. In some embodiments the coadministration is simultaneous or sequential. In some embodiments, the anti-TF antibody-drug conjugate as described herein is administered simultaneously with the platinum-based agent. In some embodiments, simultaneous means that the anti-TF antibody-drug conjugate and the platinum-based agent are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate and the platinum-based agent are administered to the subject less than one hour apart, such as less than 30 minutes apart, less than 15 minutes apart, less than 10 minutes apart or less than 5 minutes apart. In some embodiments, the anti-TF antibody-drug conjugate is administered sequentially with the platinum-based agent. In some embodiments, sequential administration means that the anti-TF antibody-drug conjugate and the platinum-based agent are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart. In some embodiments, a composition comprising an anti-TF antibody-drug conjugate as described herein and/or an platinum-based agent as described herein is coadministered with one or more therapeutic agents to eliminate or reduce the severity of one or more adverse events. In some embodiments, a composition comprising an anti-TF antibody-drug conjugate as described herein and/or an platinum-based agent as described herein is coadministered with one or more therapeutic agents to prevent the development of the adverse event or to reduce the severity of the adverse event.

In some embodiments, a composition comprising an anti-TF antibody-drug conjugate as described herein, such as e.g., tisotumab vedotin, and/or platinum-based agent as described herein, such as e.g., carboplatin, is coadministered with one or additional therapeutic agents. In some embodiments the coadministration is simultaneous or sequential. In some embodiments, the anti-TF antibody-drug conjugate as described herein and/or platinum-based agent as described herein is administered simultaneously with the one or more additional therapeutic agents. In some embodiments, simultaneous means that the anti-TF antibody-drug conjugate and/or platinum-based agent and the one or more therapeutic agents are administered to the subject less than about one hour apart, such as less than about 30 minutes apart, less than about 15 minutes apart, less than about 10 minutes apart or less than about 5 minutes apart. In some embodiments, the anti-TF antibody-drug conjugate and/or platinum-based agent is administered sequentially with the one or more additional therapeutic agents. In some embodiments, simultaneous means that the anti-TF antibody-drug conjugate and/or platinum-based agent and the one or more therapeutic agents are administered to the subject less than one hour apart, such as less than 30 minutes apart, less than 15 minutes apart, less than 10 minutes apart or less than 5 minutes apart. In some embodiments, the anti-TF antibody-drug conjugate and/or platinum-based agent is administered sequentially with the one or more additional therapeutic agents. In some embodiments, sequential administration means that the anti-TF antibody-drug conjugate and/or platinum-based agent and the one or more additional therapeutic agents are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart.

In some embodiments, a composition comprising an anti-TF antibody-drug conjugate as described herein, such as e.g., tisotumab vedotin, and/or platinum-based agent as described herein, such as e.g., carboplatin, is coadministered with one or more therapeutic agents to eliminate or reduce the severity of one or more adverse events. In some embodiments the coadministration is simultaneous or sequential. In some embodiments, the anti-TF antibody-drug conjugate and/or platinum-based agent is administered simultaneously with the one or more therapeutic agents to eliminate or reduce the severity of one or more adverse events. In some embodiments, simultaneous means that the anti-TF antibody-drug conjugate and/or platinum-based agent and the one or more therapeutic agents to eliminate or reduce the severity of one or more adverse events are administered to the subject less than about one hour apart, such as less than about 30 minutes apart, less than about 15 minutes apart, less than about 10 minutes apart or less than about 5 minutes apart. In some embodiments, simultaneous means that the anti-TF antibody-drug conjugate and/or platinum-based agent and the one or more therapeutic agents to eliminate or reduce the severity of one or more adverse events are administered to the subject less than one hour apart, such as less than 30 minutes apart, less than 15 minutes apart, less than 10 minutes apart or less than 5 minutes apart. In some embodiments, the anti-TF antibody-drug conjugate and/or platinum-based agent is administered sequentially with the one or more therapeutic agents to eliminate or reduce the severity of one or more adverse events. In some embodiments, sequential administration means that the anti-TF antibody-drug conjugate and/or platinum-based agent and the one or more additional therapeutic agents are administered a least 1 hour apart, at least 2 hours apart, at least 3 hours apart, at least 4 hours apart, at least 5 hours apart, at least 6 hours apart, at least 7 hours apart, at least 8 hours apart, at least 9 hours apart, at least 10 hours apart, at least 11 hours apart, at least 12 hours apart, at least 13 hours apart, at least 14 hours apart, at least 15 hours apart, at least 16 hours apart, at least 17 hours apart, at least 18 hours apart, at least 19 hours apart, at least 20 hours apart, at least 21 hours apart, at least 22 hours apart, at least 23 hours apart, at least 24 hours apart, at least 2 days apart, at least 3 days apart, at least 4 days apart, at least 5 days apart, at least 5 days apart, at least 7 days apart, at least 2 weeks apart, at least 3 weeks apart or at least 4 weeks apart. In some embodiments, the anti-TF antibody-drug conjugate and/or platinum-based agent is administered prior to the one or more therapeutic agents to eliminate or reduce the severity of one or more adverse events. In some embodiments, the one or more therapeutic agents to eliminate or reduce the severity of one or more adverse events is administered prior to the anti-TF antibody-drug conjugate and/or platinum-based agent.

V. Articles of Manufacture and Kits

In another aspect, an article of manufacture or kit is provided which comprises an anti-TF antibody-drug conjugate described herein, such as e.g., tisotumab vedotin, and/or a platinum-based agent described herein, such as e.g., carboplatin. The article of manufacture or kit may further comprise instructions for use of the anti-TF antibody-drug conjugate and/or platinum-based agent in the methods of the invention. Thus, in certain embodiments, the article of manufacture or kit comprises instructions for the use of an anti-TF antibody-drug conjugate and/or a platinum-based agent in methods for treating cancer (e.g., bladder cancer or cervical cancer) in a subject comprising administering to the subject an effective amount of an anti-TF antibody-drug conjugate and/or platinum-based agent. In some embodiments, the cancer is bladder cancer. In some embodiments, the cancer is cervical cancer. In some embodiments, the cervical cancer is advanced stage cervical cancer. In some embodiments, the advanced stage cervical cancer is metastatic cervical cancer. In some embodiments, the advanced stage cervical cancer is a stage 3 or stage 4 cervical cancer. In some embodiments, the cervical cancer is metastatic cancer and recurrent cancer. In some embodiments the cervical cancer is recurrent cancer. In some embodiments, the subject is not a candidate for curative therapy. In some embodiments, the subject has not received prior systemic therapy for the cervical cancer. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject such as bladder cancer or cervical cancer described herein (e.g., advanced cervical cancer such as grade 3 or grade 4 or metastatic cervical cancer). The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-TF antibody-drug conjugate is a first medicament, and which article or kit further comprises instructions on the label or package insert for treating the subject with the second medicament, in an effective amount. In some embodiments, the second medicament is a platinum-based agent as described herein. In some embodiments, the label or package insert indicates that the first and second medicaments are to be administered sequentially or simultaneously, as described herein.

The article of manufacture or kit herein optionally further comprises a container comprising a third medicament, wherein the third medicament is for eliminating or reducing the severity of one or more adverse events, wherein the anti-TF antibody-drug conjugate is a first medicament, the platinum-based agent is a second medicament, and which article or kit further comprises instructions on the label or package insert for treating the subject with the third medicament, in an effective amount. In some embodiments, the label or package insert indicates that the first, second and third medicaments are to be administered sequentially or simultaneously, as described herein, for example wherein the label or package insert indicates that the anti-TF antibody-drug conjugate is to be administered first, followed by administration of the platinum-based agent, followed by administration of the third medicament.

In some embodiments, the anti-TF antibody-drug conjugate and/or platinum-based agent is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

VII. Exemplary Embodiments

Among the embodiments provided herein are:

1. A method of treating cancer in a subject, the method comprising administering to the subject a platinum-based agent and an antibody-drug conjugate that binds to tissue factor (TF), wherein the antibody-drug conjugate comprises an anti-TF antibody or an antigen-binding fragment thereof conjugated to a monomethyl auristatin or a functional analog thereof or a functional derivative thereof.

2. The method of embodiment 1, wherein the antibody-drug conjugate is administered at a dose ranging from about 0.9 mg/kg to about 2.1 mg/kg.

3. The method of embodiment 2, wherein the antibody-drug conjugate is administered at a dose of about 1.3 mg/kg.

4. The method of embodiment 2, wherein the antibody-drug conjugate is administered at a dose of 1.3 mg/kg.

5. The method of embodiment 2, wherein the antibody-drug conjugate is administered at a dose of about 2.0 mg/kg.

6. The method of embodiment 2, wherein the antibody-drug conjugate is administered at a dose of 2.0 mg/kg.

7. The method of any one of embodiments 1-6, wherein the antibody-drug conjugate is administered once about every 1 week, once about every 2 weeks, once about every 3 weeks or once about every 4 weeks.

8. The method of embodiment 7, wherein the antibody-drug conjugate is administered once about every 3 weeks.

9. The method of embodiment 7, wherein the antibody-drug conjugate is administered once every 3 weeks.

10. The method of any one of embodiments 1-9, wherein the platinum-based agent is administered at a dose between about AUC=4 and about AUC=6.

11. The method of embodiment 10, wherein the platinum-based agent is administered a dose of about AUC=5.

12. The method of embodiment 10, wherein the platinum-based agent is administered a dose of AUC=5.

13. The method of any one of embodiments 1-12, wherein the platinum-based agent is administered once about every 1 week, once about every 2 weeks, once about every 3 weeks or once about every 4 weeks.

14. The method of embodiment 13, wherein the platinum-based agent is administered once about every 3 weeks.

15. The method of embodiment 13, wherein the platinum-based agent is administered once every 3 weeks.

16. The method of any one of embodiments 1-15, wherein the cancer is bladder cancer.

17. The method of any one of embodiments 1-15, wherein the cancer is cervical cancer.

18. The method of embodiment 17, wherein the subject is not a candidate for curative therapy.

19. The method of embodiment 18, wherein curative therapy comprises radiotherapy and/or exenterative surgery.

20. The method of embodiment 17, wherein the subject has not received prior systemic therapy for the cervical cancer.

21. The method of any one of embodiments 17-20, wherein the cervical cancer is an adenocarcinoma, an adenosquamous carcinoma or a squamous cell carcinoma.

22. The method of any one of embodiments 17-21, wherein the cervical cancer is an advanced stage cervical cancer.

23. The method of embodiment 22, wherein the advanced stage cervical cancer is a stage 3 or stage 4 cervical cancer.

24. The method of embodiment 22 or 23, wherein the advanced stage cervical cancer is metastatic cervical cancer.

25. The method of any one of embodiments 17-24, wherein the cervical cancer is recurrent cervical cancer.

26. The method of any one of embodiments 1-25, wherein the monomethyl auristatin is monomethyl auristatin E (MMAE).

27. The method of any one of embodiments 1-26, wherein the anti-TF antibody or antigen-binding fragment thereof of the antibody-drug conjugate is a monoclonal antibody or a monoclonal antigen-binding fragment thereof.

28. The method of any one of embodiments 1-27, wherein the anti-TF antibody or antigen-binding fragment thereof of the antibody-drug conjugate comprises a heavy chain variable region and a light chain variable region, wherein the heavy chain variable region comprises:
 (i) a CDR-H1 comprising the amino acid sequence of SEQ ID NO:1;
 (ii) a CDR-H2 comprising the amino acid sequence of SEQ ID NO:2; and
 (iii) a CDR-H3 comprising the amino acid sequence of SEQ ID NO:3; and
wherein the light chain variable region comprises:
 (i) a CDR-L1 comprising the amino acid sequence of SEQ ID NO:4;
 (ii) a CDR-L2 comprising the amino acid sequence of SEQ ID NO:5; and
 (iii) a CDR-L3 comprising the amino acid sequence of SEQ ID NO:6, wherein the CDRs of the anti-TF antibody or antigen-binding fragment thereof are defined by the IMGT numbering scheme.

29. The method of any one of embodiments 1-28, wherein the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8.

30. The method of any one of embodiments 1-29, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

31. The method of any one of embodiments 1-30, wherein the anti-TF antibody of the antibody-drug conjugate is tisotumab.

32. The method of any one of embodiments 1-31, wherein the antibody-drug conjugate further comprises a linker between the anti-TF antibody or antigen-binding fragment thereof and the monomethyl auristatin.

33. The method of embodiment 32, wherein the linker is a cleavable peptide linker.

34. The method of embodiment 33, wherein the cleavable peptide linker has a formula: -MC-vc-PAB-, wherein:
 a) MC is:

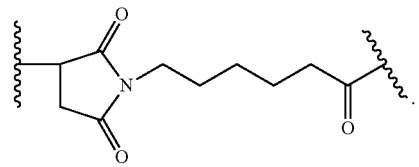 [SMILES: *C(=O)CCCCCN1C(=O)CC(*)C1=O]

b) vc is the dipeptide valine-citrulline, and
 c) PAB is:

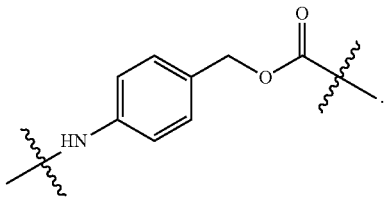 [SMILES: *Nc1ccc(COC(*)=O)cc1]

35. The method of any one of embodiments 32-34, wherein the linker is attached to sulphydryl residues of the anti-TF antibody obtained by partial reduction or full reduction of the anti-TF antibody or antigen-binding fragment thereof.

36. The method of embodiment 35, wherein the linker is attached to MMAE, wherein the antibody-drug conjugate has the following structure:

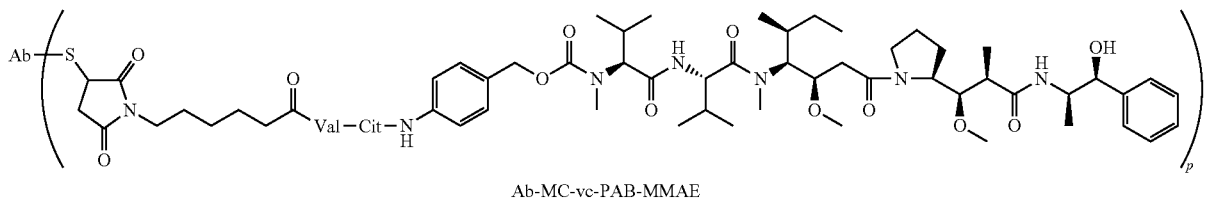

Ab-MC-vc-PAB-MMAE wherein p denotes a number from 1 to 8, S represents a sulphydryl residue of the anti-TF antibody, and Ab designates the anti-TF antibody or antigen-binding fragment thereof.

37. The method of embodiment 36, wherein the average value of p in a population of the antibody-drug conjugates is about 4.

38. The method of any one of embodiments 1-37, wherein the antibody-drug conjugate is tisotumab vedotin.

39. The method of any one of embodiments 1-38, wherein the route of administration for the antibody-drug conjugate is intravenous.

40. The method of any one of embodiments 1-39, wherein the platinum-based agent is selected from the group consisting of carboplatin, cisplatin, oxaliplatin, and nedaplatin.

41. The method of any one of embodiments 1-39, wherein the platinum-based agent is carboplatin.

42. The method of any one of embodiments 1-39, wherein the platinum-based agent is cisplatin.

43. The method of any one of embodiments 1-42, wherein the route of administration for the platinum-based agent is intravenous.

44. The method of any one of embodiments 1-43, wherein the platinum-based agent and the antibody-drug conjugate are administered sequentially.

45. The method of any one of embodiments 1-43, wherein the platinum-based agent and the antibody-drug conjugate are administered simultaneously.

46. The method of any one of embodiments 1-45, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

47. The method of any one of embodiments 1-46, wherein one or more therapeutic effects in the subject is improved after administration of the antibody-drug conjugate and the platinum-based agent relative to a baseline.

48. The method of embodiment 47, wherein the one or more therapeutic effects is selected from the group consisting of: size of a tumor derived from the cervical cancer, objective response rate, duration of response, time to response, progression free survival, and overall survival.

49. The method of any one of embodiments 1-48, wherein the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent.

50. The method of any one of embodiments 1-49, wherein the objective response rate is at least about 20%, at least about 25%, at least about 30%, at least about 35%, at least about 40%, at least about 45%, at least about 50%, at least about 60%, at least about 70%, or at least about 80%.

51. The method of any one of embodiments 1-50, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

52. The method of any one of embodiments 1-51, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

53. The method of any one of embodiments 1-52, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

54. The method of any one of embodiments 1-53, wherein the subject has one or more adverse events and is further administered an additional therapeutic agent to eliminate or reduce the severity of the one or more adverse events.

55. The method of any one of embodiments 1-54, wherein the subject is at risk of developing one or more adverse events and is further administered an additional therapeutic agent to prevent or reduce the severity of the one or more adverse events.

56. The method of embodiment 54 or embodiment 55, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

57. The method of embodiment 54 or embodiment 55, wherein the one or more adverse events is a grade 3 or greater adverse event.

58. The method of embodiment 54 or embodiment 55, wherein the one or more adverse events is a serious adverse event.

59. The method of embodiment 54 or embodiment 55, wherein the one or more adverse events is conjunctivitis and/or keratitis and the additional agent is a preservative-free lubricating eye drop, an ocular vasoconstrictor and/or a steroid eye drop.

60. The method of any one of embodiments 1-59, wherein the subject is a human.

61. The method of any one of embodiments 1-60, wherein the antibody-drug conjugate is in a pharmaceutical composition comprising the antibody-drug conjugate and a pharmaceutical acceptable carrier.

62. The method of any one of embodiments 1-61, wherein the platinum-based agent is in a pharmaceutical composition comprising the platinum-based agent and a pharmaceutical acceptable carrier.

63. A kit comprising:
(a) a dosage ranging from about AUC=4 to about AUC=6 of a platinum-based agent;
(b) a dosage ranging from about 0.9 mg/kg to about 2.1 mg/kg of an antibody-drug conjugate that binds to tissue factor (TF), wherein the antibody-drug conjugate comprises an anti-TF antibody or an antigen-binding fragment thereof conjugated to a monomethyl auristatin or a functional analog thereof or a functional derivative thereof; and
(c) instructions for using the platinum-based agent and the antibody drug conjugate according to the method of any one of embodiments 1-62.

64. The kit of embodiment 63, wherein the platinum-based agent is carboplatin.

65. The kit of embodiment 63 or embodiment 64, wherein the antibody-drug conjugate is tisotumab vedotin.

66. An antibody-drug conjugate that binds to TF for use in the treatment of cancer in a subject, wherein the antibody-drug conjugate is for administration, or to be administered in combination with a platinum-based agent, wherein the antibody-drug conjugate comprises an anti-TF antibody or an antigen-binding fragment thereof conjugated to a monomethyl auristatin or a functional analog thereof or a functional derivative thereof.

67. The antibody-drug conjugate for use of embodiment 66, wherein the antibody-drug conjugate is administered at a dose ranging from about 0.9 mg/kg to about 2.1 mg/kg.

68. The antibody-drug conjugate for use of embodiment 67, wherein the antibody-drug conjugate is administered at a dose of about 1.3 mg/kg.

69. The antibody-drug conjugate for use of embodiment 67, wherein the antibody-drug conjugate is administered at a dose of 1.3 mg/kg.

70. The antibody-drug conjugate for use of embodiment 67, wherein the antibody-drug conjugate is administered at a dose of about 2.0 mg/kg.

71. The antibody-drug conjugate for use of embodiment 67, wherein the antibody-drug conjugate is administered at a dose of 2.0 mg/kg.

72. The antibody-drug conjugate for use of any one of embodiments 66-71, wherein the antibody-drug conjugate is administered once about every 1 week, once about every 2 weeks, once about every 3 weeks or once about every 4 weeks.

73. The antibody-drug conjugate for use of embodiment 72, wherein the antibody-drug conjugate is administered once about every 3 weeks.

74. The antibody-drug conjugate for use of embodiment 72, wherein the antibody-drug conjugate is administered once every 3 weeks.

75. The antibody-drug conjugate for use of any one of embodiments 66-74, wherein the platinum-based agent is administered at a dose between about AUC=4 and about AUC=6.

76. The antibody-drug conjugate for use of embodiment 75, wherein the platinum-based agent is administered a dose of about AUC=5.

77. The antibody-drug conjugate for use of embodiment 75, wherein the platinum-based agent is administered a dose of AUC=5.

78. The antibody-drug conjugate for use of any one of embodiments 66-77, wherein the platinum-based agent is administered once about every 1 week, once about every 2 weeks, once about every 3 weeks or once about every 4 weeks.

79. The antibody-drug conjugate for use of embodiment 78, wherein the platinum-based agent is administered once about every 3 weeks.

80. The antibody-drug conjugate for use of embodiment 78, wherein the platinum-based agent is administered once every 3 weeks.

81. The antibody-drug conjugate for use of any one of embodiments 66-80, wherein the cancer is bladder cancer.

82. The antibody-drug conjugate for use of any one of embodiments 66-80, wherein the cancer is cervical cancer.

83. The antibody-drug conjugate for use of embodiment 82, wherein the subject is not a candidate for curative therapy.

84. The antibody-drug conjugate for use of embodiment 83, wherein curative therapy comprises radiotherapy and/or exenterative surgery.

85. The antibody-drug conjugate for use of embodiment 82, wherein the subject has not received prior systemic therapy for the cervical cancer.

86. The antibody-drug conjugate for use of any one of embodiments 82-85, wherein the cervical cancer is an adenocarcinoma, an adenosquamous carcinoma or a squamous cell carcinoma.

87. The antibody-drug conjugate for use of any one of embodiments 82-86, wherein the cervical cancer is an advanced stage cervical cancer.

88. The antibody-drug conjugate for use of embodiment 87, wherein the advanced stage cervical cancer is a stage 3 or stage 4 cervical cancer.

89. The antibody-drug conjugate for use of embodiment 87 or 88, wherein the advanced stage cervical cancer is metastatic cervical cancer.

90. The antibody-drug conjugate for use of any one of embodiments 82-89, wherein the cervical cancer is recurrent cervical cancer.

91. The antibody-drug conjugate for use of any one of embodiments 66-90, wherein the monomethyl auristatin is monomethyl auristatin E (MMAE).

92. The antibody-drug conjugate for use of any one of embodiments 66-91, wherein the anti-TF antibody or antigen-binding fragment thereof of the antibody-drug conjugate is a monoclonal antibody or a monoclonal antigen-binding fragment thereof.

93. The antibody-drug conjugate for use of any one of embodiments 66-92, wherein the anti-TF antibody or antigen-binding fragment thereof of the antibody-drug conjugate comprises a heavy chain variable region and a light chain variable region, wherein the heavy chain variable region comprises:

(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and
wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

94. The antibody-drug conjugate for use of any one of embodiments 66-93, wherein the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8.

95. The antibody-drug conjugate for use of any one of embodiments 66-94, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

96. The antibody-drug conjugate for use of any one of embodiments 66-95, wherein the anti-TF antibody of the antibody-drug conjugate is tisotumab.

97. The antibody-drug conjugate for use of any one of embodiments 66-96, wherein the antibody-drug conjugate further comprises a linker between the anti-TF antibody or antigen-binding fragment thereof and the monomethyl auristatin.

98. The antibody-drug conjugate for use of embodiment 97, wherein the linker is a cleavable peptide linker.

99. The antibody-drug conjugate for use of embodiment 98, wherein the cleavable peptide linker has a formula: -MC-vc-PAB-, wherein:
a) MC is:

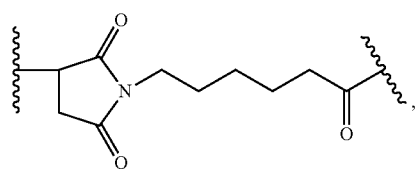

b) vc is the dipeptide valine-citrulline, and c) PAB is:

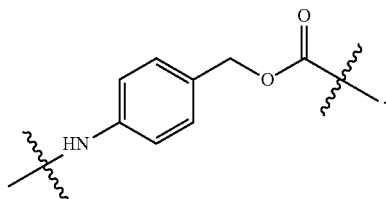 [SMILES: *Nc1ccc(COC(*)=O)cc1]

100. The antibody-drug conjugate for use of any one of embodiments 97-99, wherein the linker is attached to sulphydryl residues of the anti-TF antibody obtained by partial reduction or full reduction of the anti-TF antibody or antigen-binding fragment thereof.

101. The antibody-drug conjugate for use of embodiment 100, wherein the linker is attached to MMAE, wherein the antibody-drug conjugate has the following structure:

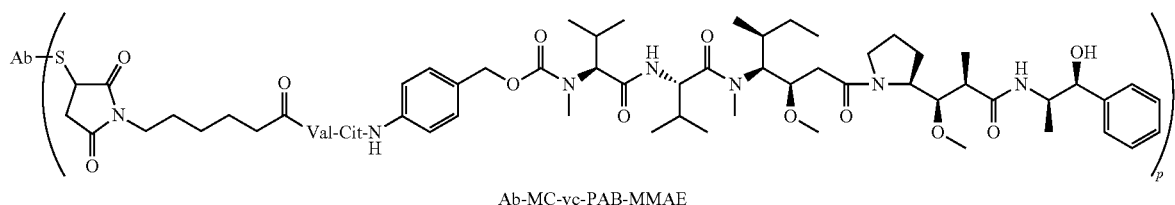

Ab-MC-vc-PAB-MMAE wherein p denotes a number from 1 to 8, S represents a sulphydryl residue of the anti-TF antibody, and Ab designates the anti-TF antibody or antigen-binding fragment thereof.

102. The antibody-drug conjugate for use of embodiment 101, wherein the average value of p in a population of the antibody-drug conjugates is about 4.

103. The antibody-drug conjugate for use of any one of embodiments 66-102, wherein the antibody-drug conjugate is tisotumab vedotin.

104. The antibody-drug conjugate for use of any one of embodiments 66-103, wherein the route of administration for the antibody-drug conjugate is intravenous.

105. The antibody-drug conjugate for use of any one of embodiments 66-104, wherein the platinum-based agent is selected from the group consisting of carboplatin, cisplatin, oxaliplatin, and nedaplatin.

106. The antibody-drug conjugate for use of any one of embodiments 66-104, wherein the platinum-based agent is carboplatin.

107. The antibody-drug conjugate for use of any one of embodiments 66-104, wherein the platinum-based agent is cisplatin.

108. The antibody-drug conjugate for use of any one of embodiments 66-107, wherein the route of administration for the platinum-based agent is intravenous.

109. The antibody-drug conjugate for use of any one of embodiments 66-108, wherein the platinum-based agent and the antibody-drug conjugate are administered sequentially.

110. The antibody-drug conjugate for use of any one of embodiments 66-108, wherein the platinum-based agent and the antibody-drug conjugate are administered simultaneously.

111. The antibody-drug conjugate for use of any one of embodiments 66-110, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

112. The antibody-drug conjugate for use of any one of embodiments 66-111, wherein one or more therapeutic effects in the subject is improved after administration of the antibody-drug conjugate and the platinum-based agent relative to a baseline.

113. The antibody-drug conjugate for use of embodiment 112, wherein the one or more therapeutic effects is selected from the group consisting of: size of a tumor derived from the cervical cancer, objective response rate, duration of response, time to response, progression free survival, and overall survival.

114. The antibody-drug conjugate for use of any one of embodiments 66-113, wherein the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent.

115. The antibody-drug conjugate for use of any one of embodiments 66-114, wherein the objective response rate is at least about 20%, at least about 25%, at least about 30%, at least about 35%, at least about 40%, at least about 45%, at least about 50%, at least about 60%, at least about 70%, or at least about 80%.

116. The antibody-drug conjugate for use of any one of embodiments 66-115, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

117. The antibody-drug conjugate for use of any one of embodiments 66-116, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

118. The antibody-drug conjugate for use of any one of embodiments 66-117, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

119. The antibody-drug conjugate for use of any one of embodiments 66-118, wherein the subject has one or more adverse events and is further administered an additional therapeutic agent to eliminate or reduce the severity of the one or more adverse events.

120. The antibody-drug conjugate for use of any one of embodiments 66-119, wherein the subject is at risk of developing one or more adverse events and is further administered an additional therapeutic agent to prevent or reduce the severity of the one or more adverse events.

121. The antibody-drug conjugate for use of embodiment 119 or embodiment 120, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

122. The antibody-drug conjugate for use of embodiment 119 or embodiment 120, wherein the one or more adverse events is a grade 3 or greater adverse event.

123. The antibody-drug conjugate for use of embodiment 119 or embodiment 120, wherein the one or more adverse events is a serious adverse event.

124. The antibody-drug conjugate for use of embodiment 119 or embodiment 120, wherein the one or more adverse events is conjunctivitis and/or keratitis and the additional agent is a preservative-free lubricating eye drop, an ocular vasoconstrictor and/or a steroid eye drop.

125. The antibody-drug conjugate for use of any one of embodiments 66-124, wherein the subject is a human.

126. The antibody-drug conjugate for use of any one of embodiments 66-125, wherein the antibody-drug conjugate is in a pharmaceutical composition comprising the antibody-drug conjugate and a pharmaceutical acceptable carrier.

127. The antibody-drug conjugate for use of any one of embodiments 66-126, wherein the platinum-based agent is in a pharmaceutical composition comprising the platinum-based agent and a pharmaceutical acceptable carrier.

128. Use of an antibody-drug conjugate that binds to TF for the manufacture of a medicament for treating cancer in a subject, wherein the medicament is for use in combination with a platinum-based agent, wherein the antibody-drug conjugate comprises an anti-TF antibody or an antigen-binding fragment thereof conjugated to a monomethyl auristatin or a functional analog thereof or a functional derivative thereof.

129. The use of embodiment 128, wherein the antibody-drug conjugate is administered at a dose ranging from about 0.9 mg/kg to about 2.1 mg/kg.

130. The use of embodiment 129, wherein the antibody-drug conjugate is administered at a dose of about 1.3 mg/kg.

131. The use of embodiment 129, wherein the antibody-drug conjugate is administered at a dose of 1.3 mg/kg.

132. The use of embodiment 129, wherein the antibody-drug conjugate is administered at a dose of about 2.0 mg/kg.

133. The use of embodiment 129, wherein the antibody-drug conjugate is administered at a dose of 2.0 mg/kg.

134. The use of any one of embodiments 128-133, wherein the antibody-drug conjugate is administered once about every 1 week, once about every 2 weeks, once about every 3 weeks or once about every 4 weeks.

135. The use of embodiment 134, wherein the antibody-drug conjugate is administered once about every 3 weeks.

136. The use of embodiment 134, wherein the antibody-drug conjugate is administered once every 3 weeks.

137. The use of any one of embodiments 128-136, wherein the platinum-based agent is administered at a dose between about AUC=4 and about AUC=6.

138. The use of embodiment 137, wherein the platinum-based agent is administered a dose of about AUC=5.

139. The use of embodiment 137, wherein the platinum-based agent is administered a dose of AUC=5.

140. The use of any one of embodiments 128-139, wherein the platinum-based agent is administered once about every 1 week, once about every 2 weeks, once about every 3 weeks or once about every 4 weeks.

141. The use of embodiment 140, wherein the platinum-based agent is administered once about every 3 weeks.

142. The use of embodiment 140, wherein the platinum-based agent is administered once every 3 weeks.

143. The use of any one of embodiments 128-142, wherein the cancer is bladder cancer.

144. The use of any one of embodiments 128-142, wherein the cancer is cervical cancer.

145. The use of embodiment 144, wherein the subject is not a candidate for curative therapy.

146. The use of embodiment 145, wherein curative therapy comprises radiotherapy and/or exenterative surgery.

147. The use of embodiment 144, wherein the subject has not received prior systemic therapy for the cervical cancer.

148. The use of any one of embodiments 144-147, wherein the cervical cancer is an adenocarcinoma, an adenosquamous carcinoma or a squamous cell carcinoma.

149. The use of any one of embodiments 144-148, wherein the cervical cancer is an advanced stage cervical cancer.

150. The use of embodiment 149, wherein the advanced stage cervical cancer is a stage 3 or stage 4 cervical cancer.

151. The use of embodiment 149 or 150, wherein the advanced stage cervical cancer is metastatic cervical cancer.

152. The use of any one of embodiments 144-151, wherein the cervical cancer is recurrent cervical cancer.

153. The use of any one of embodiments 128-152, wherein the monomethyl auristatin is monomethyl auristatin E (MMAE).

154. The use of any one of embodiments 128-153, wherein the anti-TF antibody or antigen-binding fragment thereof of the antibody-drug conjugate is a monoclonal antibody or a monoclonal antigen-binding fragment thereof.

155. The use of any one of embodiments 128-154, wherein the anti-TF antibody or antigen-binding fragment thereof of the antibody-drug conjugate comprises a heavy chain variable region and a light chain variable region, wherein the heavy chain variable region comprises:
(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and
wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

156. The use of any one of embodiments 128-155, wherein the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8.

157. The use of any one of embodiments 128-156, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

158. The use of any one of embodiments 128-157, wherein the anti-TF antibody of the antibody-drug conjugate is tisotumab.

159. The use of any one of embodiments 128-158, wherein the antibody-drug conjugate further comprises a linker between the anti-TF antibody or antigen-binding fragment thereof and the monomethyl auristatin.

160. The use of embodiment 159, wherein the linker is a cleavable peptide linker.

161. The use of embodiment 160, wherein the cleavable peptide linker has a formula: -MC-vc-PAB-, wherein:
a) MC is:

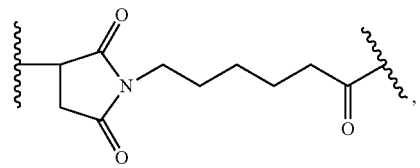 [SMILES: *C(=O)CCCCCN1C(=O)CC(*)C1=O]

b) vc is the dipeptide valine-citrulline, and
c) PAB is:

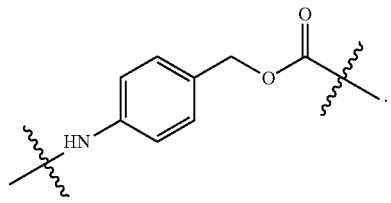 [SMILES: *Nc1ccc(COC(*)=O)cc1]

162. The use of any one of embodiments 159-161, wherein the linker is attached to sulphydryl residues of the anti-TF antibody obtained by partial reduction or full reduction of the anti-TF antibody or antigen-binding fragment thereof.

163. The use of embodiment 162, wherein the linker is attached to MMAE, wherein the antibody-drug conjugate has the following structure:

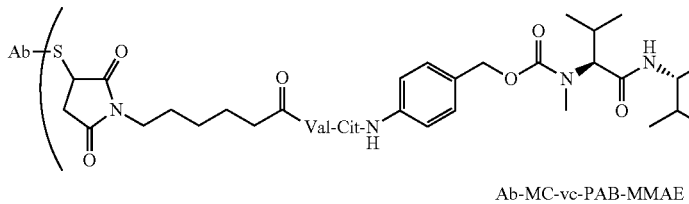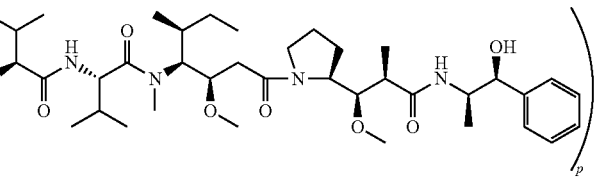

Ab-MC-vc-PAB-MMAE wherein p denotes a number from 1 to 8, S represents a sulphydryl residue of the anti-TF antibody, and Ab designates the anti-TF antibody or antigen-binding fragment thereof.

164. The use of embodiment 163, wherein the average value of p in a population of the antibody-drug conjugates is about 4.

165. The use of any one of embodiments 128-164, wherein the antibody-drug conjugate is tisotumab vedotin.

166. The use of any one of embodiments 128-165, wherein the route of administration for the antibody-drug conjugate is intravenous.

167. The use of any one of embodiments 128-166, wherein the platinum-based agent is selected from the group consisting of carboplatin, cisplatin, oxaliplatin, and nedaplatin.

168. The use of any one of embodiments 128-166, wherein the platinum-based agent is carboplatin.

169. The use of any one of embodiments 128-166, wherein the platinum-based agent is cisplatin.

170 The use of any one of embodiments 128-169, wherein the route of administration for the platinum-based agent is intravenous.

171. The use of any one of embodiments 128-170, wherein the platinum-based agent and the antibody-drug conjugate are administered sequentially.

172. The use of any one of embodiments 128-170, wherein the platinum-based agent and the antibody-drug conjugate are administered simultaneously.

173. The use of any one of embodiments 128-172, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

174. The use of any one of embodiments 128-173, wherein one or more therapeutic effects in the subject is improved after administration of the antibody-drug conjugate and the platinum-based agent relative to a baseline.

175. The use of embodiment 174, wherein the one or more therapeutic effects is selected from the group consisting of: size of a tumor derived from the cervical cancer, objective response rate, duration of response, time to response, progression free survival, and overall survival.

176. The use of any one of embodiments 128-175, wherein the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent.

177. The use of any one of embodiments 128-176, wherein the objective response rate is at least about 20%, at least about 25%, at least about 30%, at least about 35%, at least about 40%, at least about 45%, at least about 50%, at least about 60%, at least about 70%, or at least about 80%.

178. The use of any one of embodiments 128-177, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

179. The use of any one of embodiments 128-178, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

180. The use of any one of embodiments 128-179, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

181. The use of any one of embodiments 128-180, wherein the subject has one or more adverse events and is further administered an additional therapeutic agent to eliminate or reduce the severity of the one or more adverse events.

182. The use of any one of embodiments 128-181, wherein the subject is at risk of developing one or more adverse events and is further administered an additional therapeutic agent to prevent or reduce the severity of the one or more adverse events.

183. The use of embodiment 181 or embodiment 182, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

184. The use of embodiment 181 or embodiment 182, wherein the one or more adverse events is a grade 3 or greater adverse event.

185. The use of embodiment 181 or embodiment 182, wherein the one or more adverse events is a serious adverse event.

186. The use of embodiment 181 or embodiment 182, wherein the one or more adverse events is conjunctivitis and/or keratitis and the additional agent is a preservative-free lubricating eye drop, an ocular vasoconstrictor and/or a steroid eye drop.

187. The use of any one of embodiments 128-186, wherein the subject is a human.

188. The use of any one of embodiments 128-187, wherein the antibody-drug conjugate is in a pharmaceutical composition comprising the antibody-drug conjugate and a pharmaceutical acceptable carrier.

189. The use of any one of embodiments 128-188, wherein the platinum-based agent is in a pharmaceutical composition comprising the platinum-based agent and a pharmaceutical acceptable carrier.

190. A platinum-based agent for use in the treatment of cancer in a subject, wherein the platinum-based agent is for administration, or to be administered in combination with an antibody-drug conjugate that binds to TF, wherein the antibody-drug conjugate comprises an anti-TF antibody or an antigen-binding fragment thereof conjugated to a monomethyl auristatin or a functional analog thereof or a functional derivative thereof.

191. The platinum-based agent for use of embodiment 190, wherein the antibody-drug conjugate is administered at a dose ranging from about 0.9 mg/kg to about 2.1 mg/kg.

192. The platinum-based agent for use of embodiment 191, wherein the antibody-drug conjugate is administered at a dose of about 1.3 mg/kg.

193. The platinum-based agent for use of embodiment 191, wherein the antibody-drug conjugate is administered at a dose of 1.3 mg/kg.

194. The platinum-based agent for use of embodiment 191, wherein the antibody-drug conjugate is administered at a dose of about 2.0 mg/kg.

195. The platinum-based agent for use of embodiment 191, wherein the antibody-drug conjugate is administered at a dose of 2.0 mg/kg.

196. The platinum-based agent for use of any one of embodiments 190-195, wherein the antibody-drug conjugate is administered once about every 1 week, once about every 2 weeks, once about every 3 weeks or once about every 4 weeks.

197. The platinum-based agent for use of embodiment 196, wherein the antibody-drug conjugate is administered once about every 3 weeks.

198. The platinum-based agent for use of embodiment 196, wherein the antibody-drug conjugate is administered once every 3 weeks.

199. The platinum-based agent for use of any one of embodiments 190-198, wherein the platinum-based agent is administered at a dose between about AUC=4 and about AUC=6.

200. The platinum-based agent for use of embodiment 199, wherein the platinum-based agent is administered a dose of about AUC=5.

201. The platinum-based agent for use of embodiment 199, wherein the platinum-based agent is administered a dose of AUC=5.

202. The platinum-based agent for use of any one of embodiments 190-201, wherein the platinum-based agent is administered once about every 1 week, once about every 2 weeks, once about every 3 weeks or once about every 4 weeks.

203. The platinum-based agent for use of embodiment 202, wherein the platinum-based agent is administered once about every 3 weeks.

204. The platinum-based agent for use of embodiment 202, wherein the platinum-based agent is administered once every 3 weeks.

205. The platinum-based agent for use of any one of embodiments 190-204, wherein the cancer is bladder cancer.

206. The platinum-based agent for use of any one of embodiments 190-204, wherein the cancer is cervical cancer.

207. The platinum-based agent for use of embodiment 206, wherein the subject is not a candidate for curative therapy.

208. The platinum-based agent for use of embodiment 207, wherein curative therapy comprises radiotherapy and/or exenterative surgery.

209. The platinum-based agent for use of embodiment 206, wherein the subject has not received prior systemic therapy for the cervical cancer.

210. The platinum-based agent for use of any one of embodiments 206-209, wherein the cervical cancer is an adenocarcinoma, an adenosquamous carcinoma or a squamous cell carcinoma.

211. The platinum-based agent for use of any one of embodiments 206-210, wherein the cervical cancer is an advanced stage cervical cancer.

212. The platinum-based agent for use of embodiment 211, wherein the advanced stage cervical cancer is a stage 3 or stage 4 cervical cancer.

213. The platinum-based agent for use of embodiment 211 or 212, wherein the advanced stage cervical cancer is metastatic cervical cancer.

214. The platinum-based agent for use of any one of embodiments 206-213, wherein the cervical cancer is recurrent cervical cancer.

215. The platinum-based agent for use of any one of embodiments 190-214, wherein the monomethyl auristatin is monomethyl auristatin E (MMAE).

216. The platinum-based agent for use of any one of embodiments 190-215, wherein the anti-TF antibody or antigen-binding fragment thereof of the antibody-drug conjugate is a monoclonal antibody or a monoclonal antigen-binding fragment thereof.

217. The platinum-based agent for use of any one of embodiments 190-216, wherein the anti-TF antibody or antigen-binding fragment thereof of the antibody-drug conjugate comprises a heavy chain variable region and a light chain variable region, wherein the heavy chain variable region comprises:
  (i) a CDR-H1 comprising the amino acid sequence of SEQ ID NO:1;
  (ii) a CDR-H2 comprising the amino acid sequence of SEQ ID NO:2; and
  (iii) a CDR-H3 comprising the amino acid sequence of SEQ ID NO:3; and
wherein the light chain variable region comprises:
  (i) a CDR-L1 comprising the amino acid sequence of SEQ ID NO:4;
  (ii) a CDR-L2 comprising the amino acid sequence of SEQ ID NO:5; and
  (iii) a CDR-L3 comprising the amino acid sequence of SEQ ID NO:6, wherein the CDRs of the anti-TF antibody or antigen-binding fragment thereof are defined by the IMGT numbering scheme.

218. The platinum-based agent for use of any one of embodiments 190-217, wherein the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8.

219. The platinum-based agent for use of any one of embodiments 190-218, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

220. The platinum-based agent for use of any one of embodiments 190-219, wherein the anti-TF antibody of the antibody-drug conjugate is tisotumab.

221. The platinum-based agent for use of any one of embodiments 190-220, wherein the antibody-drug conjugate further comprises a linker between the anti-TF antibody or antigen-binding fragment thereof and the monomethyl auristatin.

222. The platinum-based agent for use of embodiment 221, wherein the linker is a cleavable peptide linker.

223. The platinum-based agent for use of embodiment 222, wherein the cleavable peptide linker has a formula: -MC-vc-PAB-, wherein:
a) MC is:

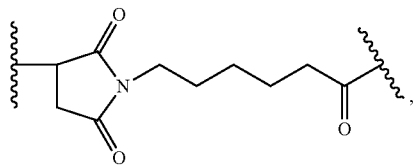

b) vc is the dipeptide valine-citrulline, and
c) PAB is:

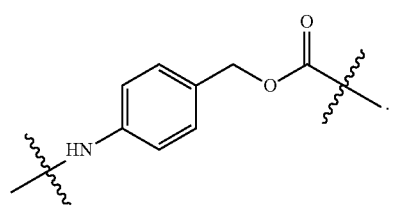 [SMILES: *Nc1ccc(COC(*)=O)cc1]

224. The platinum-based agent for use of any one of embodiments 221-223, wherein the linker is attached to sulphydryl residues of the anti-TF antibody obtained by partial reduction or full reduction of the anti-TF antibody or antigen-binding fragment thereof.

225. The platinum-based agent for use of embodiment 224, wherein the linker is attached to MMAE), wherein the antibody-drug conjugate has the following structure:

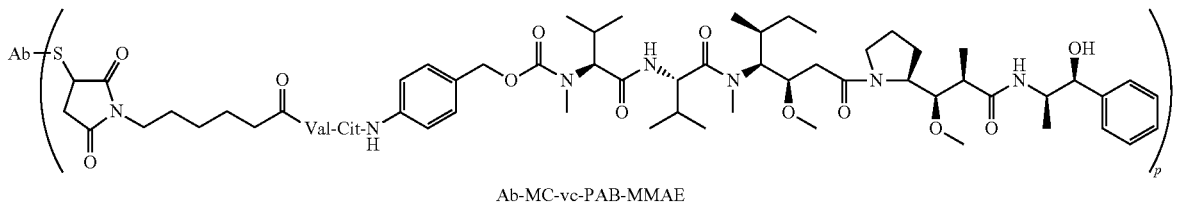

Ab-MC-vc-PAB-MMAE wherein p denotes a number from 1 to 8, S represents a sulphydryl residue of the anti-TF antibody, and Ab designates the anti-TF antibody or antigen-binding fragment thereof.

226. The platinum-based agent for use of embodiment 225, wherein the average value of p in a population of the antibody-drug conjugates is about 4.

227. The platinum-based agent for use of any one of embodiments 190-226, wherein the antibody-drug conjugate is tisotumab vedotin.

228. The platinum-based agent for use of any one of embodiments 190-227, wherein the route of administration for the antibody-drug conjugate is intravenous.

229. The platinum-based agent for use of any one of embodiments 190-228, wherein the platinum-based agent is selected from the group consisting of carboplatin, cisplatin, oxaliplatin, and nedaplatin.

230. The platinum-based agent for use of any one of embodiments 190-228, wherein the platinum-based agent is carboplatin.

231. The platinum-based agent for use of any one of embodiments 190-228, wherein the platinum-based agent is cisplatin.

232. The platinum-based agent for use of any one of embodiments 190-231, wherein the route of administration for the platinum-based agent is intravenous.

233. The platinum-based agent for use of any one of embodiments 190-232, wherein the platinum-based agent and the antibody-drug conjugate are administered sequentially.

234. The platinum-based agent for use of any one of embodiments 190-232, wherein the platinum-based agent and the antibody-drug conjugate are administered simultaneously.

235. The platinum-based agent for use of any one of embodiments 190-234, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

236. The platinum-based agent for use of any one of embodiments 190-235, wherein one or more therapeutic effects in the subject is improved after administration of the antibody-drug conjugate and the platinum-based agent relative to a baseline.

237. The platinum-based agent for use of embodiment 236, wherein the one or more therapeutic effects is selected from the group consisting of: size of a tumor derived from the cervical cancer, objective response rate, duration of response, time to response, progression free survival, and overall survival.

238. The platinum-based agent for use of any one of embodiments 190-237, wherein the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent.

239. The platinum-based agent for use of any one of embodiments 190-238, wherein the objective response rate is at least about 20%, at least about 25%, at least about 30%, at least about 35%, at least about 40%, at least about 45%, at least about 50%, at least about 60%, at least about 70%, or at least about 80%.

240. The platinum-based agent for use of any one of embodiments 190-239, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

241. The platinum-based agent for use of any one of embodiments 190-240, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

242. The platinum-based agent for use of any one of embodiments 190-241, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

243. The platinum-based agent for use of any one of embodiments 190-242, wherein the subject has one or more adverse events and is further administered an additional therapeutic agent to eliminate or reduce the severity of the one or more adverse events.

244. The platinum-based agent for use of any one of embodiments 190-243, wherein the subject is at risk of developing one or more adverse events and is further administered an additional therapeutic agent to prevent or reduce the severity of the one or more adverse events.

245. The platinum-based agent for use of embodiment 243 or embodiment 244, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

246. The platinum-based agent for use of embodiment 243 or embodiment 244, wherein the one or more adverse events is a grade 3 or greater adverse event.

247. The platinum-based agent for use of embodiment 243 or embodiment 244, wherein the one or more adverse events is a serious adverse event.

248. The platinum-based agent for use of embodiment 243 or embodiment 244, wherein the one or more adverse events is conjunctivitis and/or keratitis and the additional agent is a preservative-free lubricating eye drop, an ocular vasoconstrictor and/or a steroid eye drop.

249. The platinum-based agent for use of any one of embodiments 190-248, wherein the subject is a human.

250. The platinum-based agent for use of any one of embodiments 190-249, wherein the antibody-drug conjugate is in a pharmaceutical composition comprising the antibody-drug conjugate and a pharmaceutical acceptable carrier.

251. The platinum-based agent for use of any one of embodiments 190-250, wherein the platinum-based agent is in a pharmaceutical composition comprising the platinum-based agent and a pharmaceutical acceptable carrier.

252. Use of a platinum-based agent for the manufacture of a medicament for treating cancer in a subject, wherein the medicament is for use in combination with an antibody-drug conjugate that binds to TF, wherein the antibody-drug conjugate comprises an anti-TF antibody or an antigen-binding fragment thereof conjugated to a monomethyl auristatin or a functional analog thereof or a functional derivative thereof.

253. The use of embodiment 252, wherein the antibody-drug conjugate is administered at a dose ranging from about 0.9 mg/kg to about 2.1 mg/kg.

254. The use of embodiment 253, wherein the antibody-drug conjugate is administered at a dose of about 1.3 mg/kg.

255. The use of embodiment 253, wherein the antibody-drug conjugate is administered at a dose of 1.3 mg/kg.

256. The use of embodiment 253, wherein the antibody-drug conjugate is administered at a dose of about 2.0 mg/kg.

257. The use of embodiment 253, wherein the antibody-drug conjugate is administered at a dose of 2.0 mg/kg.

258. The use of any one of embodiments 252-257, wherein the antibody-drug conjugate is administered once about every 1 week, once about every 2 weeks, once about every 3 weeks or once about every 4 weeks.

259. The use of embodiment 258, wherein the antibody-drug conjugate is administered once about every 3 weeks.

260. The use of embodiment 258, wherein the antibody-drug conjugate is administered once every 3 weeks.

261. The use of any one of embodiments 252-260, wherein the platinum-based agent is administered at a dose between about AUC=4 and about AUC=6.

262. The use of embodiment 261, wherein the platinum-based agent is administered a dose of about AUC=5.

263. The use of embodiment 261, wherein the platinum-based agent is administered a dose of AUC=5.

264. The use of any one of embodiments 252-263, wherein the platinum-based agent is administered once about every 1 week, once about every 2 weeks, once about every 3 weeks or once about every 4 weeks.

265. The use of embodiment 264, wherein the platinum-based agent is administered once about every 3 weeks.

266. The use of embodiment 264, wherein the platinum-based agent is administered once every 3 weeks.

267. The use of any one of embodiments 252-266, wherein the cancer is bladder cancer.

268. The use of any one of embodiments 252-266, wherein the cancer is cervical cancer.

269. The use of embodiment 268, wherein the subject is not a candidate for curative therapy.

270. The use of embodiment 269, wherein curative therapy comprises radiotherapy and/or exenterative surgery.

271. The use of embodiment 268, wherein the subject has not received prior systemic therapy for the cervical cancer.

272. The use of any one of embodiments 268-271, wherein the cervical cancer is an adenocarcinoma, an adenosquamous carcinoma or a squamous cell carcinoma.

273. The use of any one of embodiments 268-272, wherein the cervical cancer is an advanced stage cervical cancer.

274. The use of embodiment 273, wherein the advanced stage cervical cancer is a stage 3 or stage 4 cervical cancer.

275. The use of embodiment 273 or 274, wherein the advanced stage cervical cancer is metastatic cervical cancer.

276. The use of any one of embodiments 268-275, wherein the cervical cancer is recurrent cervical cancer.

277. The use of any one of embodiments 252-276, wherein the monomethyl auristatin is monomethyl auristatin E (MMAE).

278. The use of any one of embodiments 252-277, wherein the anti-TF antibody or antigen-binding fragment thereof of the antibody-drug conjugate is a monoclonal antibody or a monoclonal antigen-binding fragment thereof.

279. The use of any one of embodiments 252-278, wherein the anti-TF antibody or antigen-binding fragment thereof of the antibody-drug conjugate comprises a heavy chain variable region and a light chain variable region, wherein the heavy chain variable region comprises:
(i) a CDR-H1 comprising the amino acid sequence of SEQ ID NO:1;
(ii) a CDR-H2 comprising the amino acid sequence of SEQ ID NO:2; and
(iii) a CDR-H3 comprising the amino acid sequence of SEQ ID NO:3; and
wherein the light chain variable region comprises:
(i) a CDR-L1 comprising the amino acid sequence of SEQ ID NO:4;
(ii) a CDR-L2 comprising the amino acid sequence of SEQ ID NO:5; and
(iii) a CDR-L3 comprising the amino acid sequence of SEQ ID NO:6, wherein the CDRs of the anti-TF antibody or antigen-binding fragment thereof are defined by the IMGT numbering scheme.

280. The use of any one of embodiments 252-279, wherein the anti-TF antibody or antigen-binding fragment thereof of the antibody-drug conjugate comprises a heavy chain variable region comprising an amino acid sequence at least 85% identical to the amino acid sequence of SEQ ID NO:7 and a light chain variable region comprising an amino acid sequence at least 85% identical to the amino acid sequence of SEQ ID NO:8.

281. The use of any one of embodiments 252-280, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

282. The use of any one of embodiments 252-281, wherein the anti-TF antibody of the antibody-drug conjugate is tisotumab.

283. The use of any one of embodiments 252-282, wherein the antibody-drug conjugate further comprises a linker between the anti-TF antibody or antigen-binding fragment thereof and the monomethyl auristatin.

284. The use of embodiment 283, wherein the linker is a cleavable peptide linker.

285. The use of embodiment 284, wherein the cleavable peptide linker has a formula: -MC-vc-PAB-, wherein:
a) MC is:

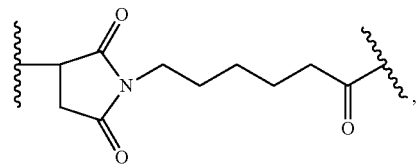 [SMILES: *C(=O)CCCCCN1C(=O)CC(*)C1=O]

b) vc is the dipeptide valine-citrulline, and
c) PAB is:

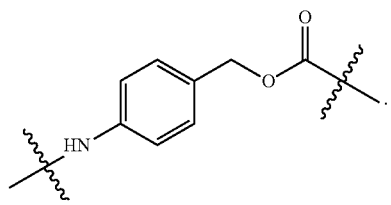 [SMILES: *Nc1ccc(COC(*)=O)cc1]

286. The use of any one of embodiments 283-285, wherein the linker is attached to sulphydryl residues of the anti-TF antibody obtained by partial reduction or full reduction of the anti-TF antibody or antigen-binding fragment thereof.

287. The use of embodiment 286, wherein the linker is attached to MMAE, wherein the antibody-drug conjugate has the following structure:

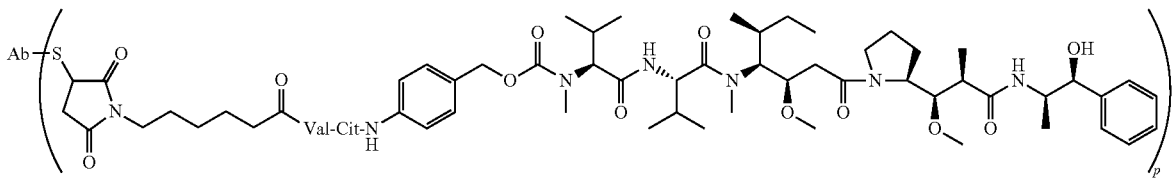

Ab-MC-vc-PAB-MMAE wherein p denotes a number from 1 to 8, S represents a sulphydryl residue of the anti-TF antibody, and Ab designates the anti-TF antibody or antigen-binding fragment thereof.

288. The use of embodiment 287, wherein the average value of p in a population of the antibody-drug conjugates is about 4.

289. The use of any one of embodiments 252-288, wherein the antibody-drug conjugate is tisotumab vedotin.

290. The use of any one of embodiments 252-289, wherein the route of administration for the antibody-drug conjugate is intravenous.

291. The use of any one of embodiments 252-290, wherein the platinum-based agent is selected from the group consisting of carboplatin, cisplatin, oxaliplatin, and nedaplatin.

292. The use of any one of embodiments 252-290, wherein the platinum-based agent is carboplatin.

293. The use of any one of embodiments 252-290, wherein the platinum-based agent is cisplatin.

294. The use of any one of embodiments 252-293, wherein the route of administration for the platinum-based agent is intravenous.

295. The use of any one of embodiments 252-294, wherein the platinum-based agent and the antibody-drug conjugate are administered sequentially.

296. The use of any one of embodiments 252-294, wherein the platinum-based agent and the antibody-drug conjugate are administered simultaneously.

297. The use of any one of embodiments 252-296, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

298. The use of any one of embodiments 252-297, wherein one or more therapeutic effects in the subject is improved after administration of the antibody-drug conjugate and the platinum-based agent relative to a baseline.

299. The use of embodiment 298, wherein the one or more therapeutic effects is selected from the group consisting of: size of a tumor derived from the cervical cancer, objective response rate, duration of response, time to response, progression free survival, and overall survival.

300. The use of any one of embodiments 252-299, wherein the size of a tumor derived from the cervical cancer is reduced by at least about 10%, at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cervical cancer before administration of the antibody-drug conjugate and the platinum-based agent.

301. The use of any one of embodiments 252-300, wherein the objective response rate is at least about 20%, at least about 25%, at least about 30%, at least about 35%, at least about 40%, at least about 45%, at least about 50%, at least about 60%, at least about 70%, or at least about 80%.

302. The use of any one of embodiments 252-301, wherein the subject exhibits progression-free survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

303. The use of any one of embodiments 252-302, wherein the subject exhibits overall survival of at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

304. The use of any one of embodiments 252-303, wherein the duration of response to the antibody-drug conjugate is at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the antibody-drug conjugate and platinum-based agent.

305. The use of any one of embodiments 252-304, wherein the subject has one or more adverse events and is further administered an additional therapeutic agent to eliminate or reduce the severity of the one or more adverse events.

306. The use of any one of embodiments 252-305, wherein the subject is at risk of developing one or more adverse events and is further administered an additional therapeutic agent to prevent or reduce the severity of the one or more adverse events.

307. The use of embodiment 305 or embodiment 306, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

308. The use of embodiment 305 or embodiment 306, wherein the one or more adverse events is a grade 3 or greater adverse event.

309. The use of embodiment 305 or embodiment 306, wherein the one or more adverse events is a serious adverse event.

310. The use of embodiment 305 or embodiment 306, wherein the one or more adverse events is conjunctivitis and/or keratitis and the additional agent is a preservative-free lubricating eye drop, an ocular vasoconstrictor and/or a steroid eye drop.

311. The use of any one of embodiments 252-310, wherein the subject is a human.

312. The use of any one of embodiments 252-311, wherein the antibody-drug conjugate is in a pharmaceutical composition comprising the antibody-drug conjugate and a pharmaceutical acceptable carrier.

313. The use of any one of embodiments 252-311, wherein the platinum-based agent is in a pharmaceutical composition comprising the platinum-based agent and a pharmaceutical acceptable carrier.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Anti-Tumor Activity of Tisotumab Vedotin in Combination with a Platinum-Based Agent in a Cervical Cancer Mouse Model Tisotumab vedotin is an antibody-drug conjugate comprising an antibody that binds to tissue factor (TF), a protease-cleavable linker, and the microtubule disrupting agent MMAE. TF is a protein aberrantly expressed in a wide number of tumors including cervical cancer and is associated with poor prognosis. See Förster Y et al. *Clin Chim Acta.* 364(1-2):12-21, 2006 and Cocco E et al. *BMC Cancer.* 11:263, 2011. Tisotumab vedotin selectively targets TF to deliver a clinically validated toxic payload to tumor cells. See Breij E C et al. *Cancer Res.* 74(4):1214-1226, 2014 and Chu A J. *Int J Inflam.* 2011; 2011. doi: 10.4061/2011/367284.

Cisplatin, a platinum-based agent, is used in combination with paclitaxel, a microtubule inhibitor, as a standard of care option for the treatment of stage IVB, recurrent or persistent cervical carcinoma. See Kitagawa R et al., *J Clin Oncol.*, 33:2129-2135, 2015. The combination of tisotumab vedotin with a platinum-based agent such as cisplatin was evaluated herein for the treatment of cervical cancer.

Materials and Methods

The in vivo anti-tumor efficacy of tisotumab vedotin in combination with cisplatin was evaluated in a patient-derived xenograft (PDX) mouse model in BALB/c nude mice (Crown Bioscience Inc.). Xenografts were derived from tumor specimens from cancer patients. Establishment and characterization of the PDX model was performed following primary implantation into nude mice. Tumor xenografts were passaged approximately three to five times until establishment of stable growth patterns. Tumor fragments were obtained from xenografts in serial passage in nude mice. Tumors were cut into fragments of 2-3 mm diameter and placed in phosphate-buffered saline (PBS) until subcutaneous implantation. A cervical cancer PDX model (HuPrime® cervical xenograft model CV1248 [R4P5]; Crown Bioscience Inc.) was used in this experiment. Tumor size was determined by caliper measurement at least two times a week and tumor volume was calculated as 0.5×length×width$^2$. When tumors reached the volume of 200 mm$^3$, mice were randomized in 11 groups (7-8 mice per treatment group). Mice were treated with the following by intravenous injections: 1) tisotumab vedotin alone at a dose level of 0.5 mg/kg, 1 mg/kg, 2 mg/kg or 4 mg/kg provided on day 0 and day 7 of treatment; 2) cisplatin alone at a dose of 4 mg/kg provided on day 0, day 7 and day 14 of treatment; 3) tisotumab vedotin at a dose level of 0.5 mg/kg, 1 mg/kg, 2 mg/kg or 4 mg/kg provided on day 0 and day 7 of treatment in combination with cisplatin at a dose of 4 mg/kg provided on day 0, day 7 and day 14 of treatment; 4) IgG1 isotype control at a dose of 4 mg/kg provided on day 0 and day 7 of treatment; or 5) IgG1-MMAE control at a dose of 4 mg/kg provided on day 0 and day 7 of treatment. Mice were observed for clinical signs of illness. Mice were housed in individually ventilated (IVC) cages, four or five mice per cage and identified by ear tags.

To determine whether there were statistically significant differences between tumor volumes in control and treatment groups, tumor volumes in the treatment groups were compared with those in the control group (e.g., treatment groups vs IgG1-MMAE control) using Mann-Whitney analysis at the last day that all groups were intact, i.e., day 38. For survival analysis (tumor volume cut-off was 1,000 mm$^3$). Mantel-Cox analysis was performed on Kaplan-Meier plots with a cut-off set at tumor volume >1,000 mm$^3$.

Results

Figure 1D:
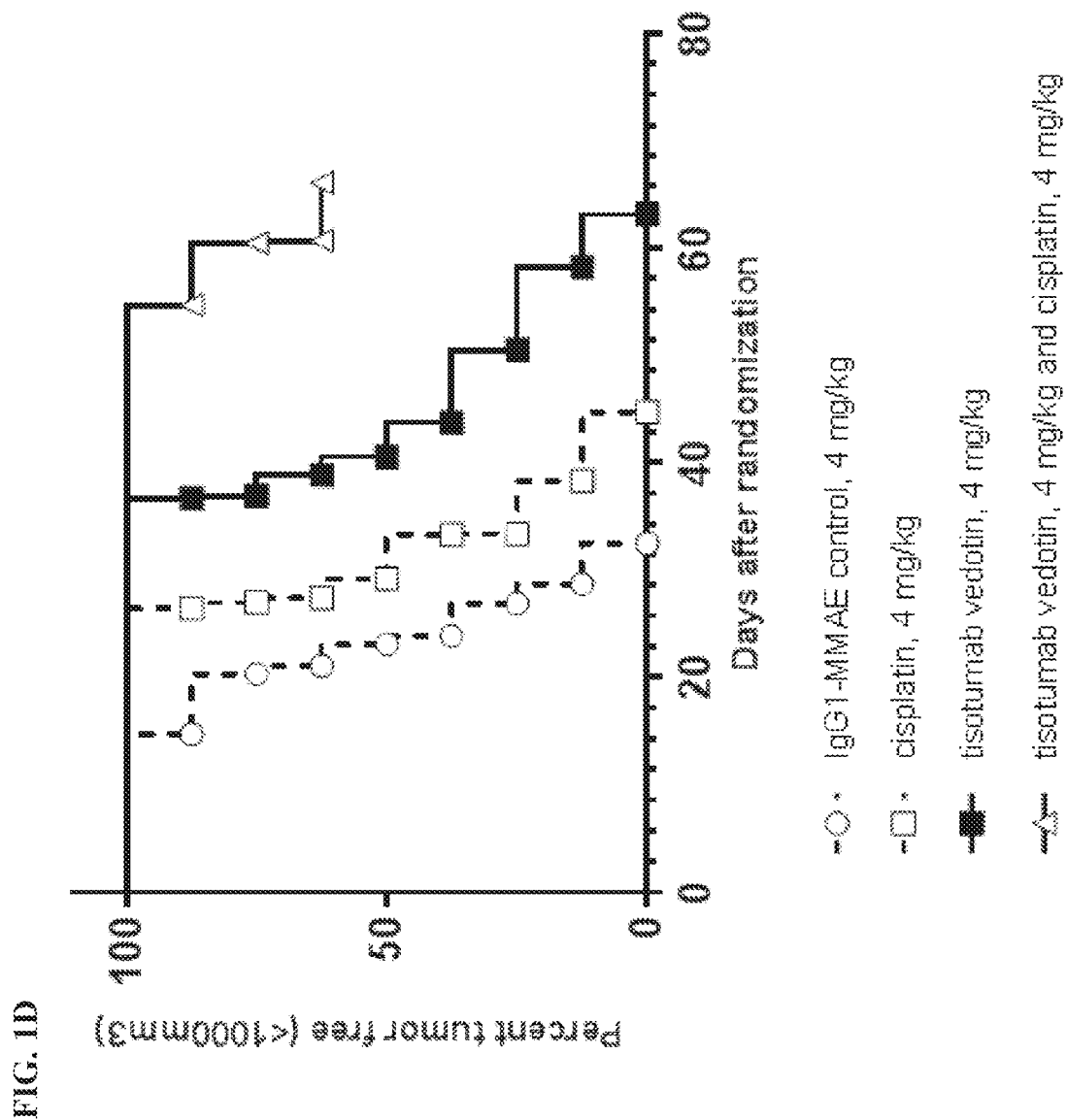
Figure 1E:
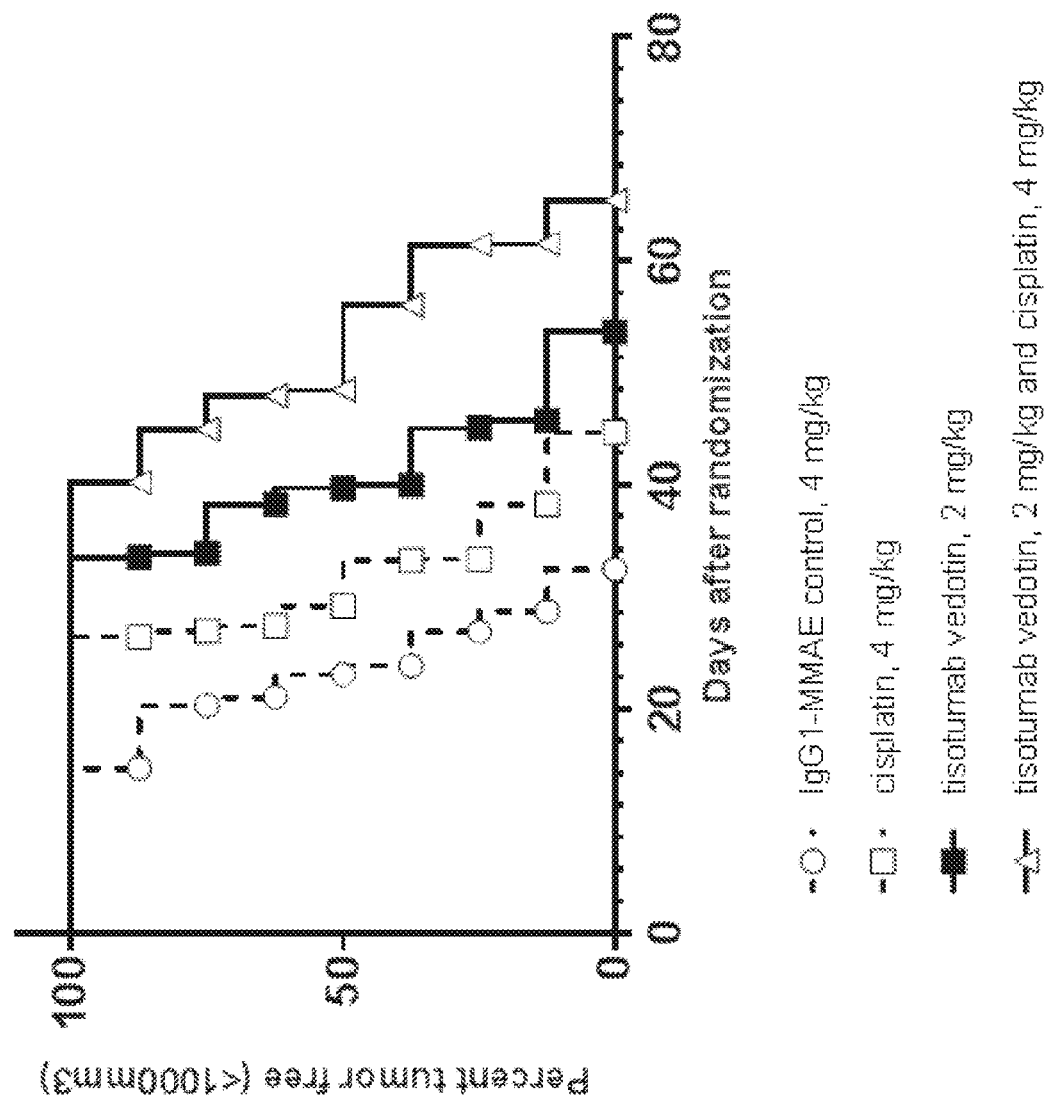

Treatment with tisotumab vedotin alone efficiently inhibited tumor growth (FIG. 1A-C) and prolonged survival (FIGS. 1D and 1E) in a mouse model for cervical cancer, both at a dose of 2 mg/kg and 4 mg/kg. Treatment with cisplatin alone also inhibited tumor growth (FIG. 1A-C) and prolonged survival (FIGS. 1D and 1E). Treatment with 2 mg/kg or 4 mg/kg tisotumab vedotin in combination with cisplatin enhanced anti-tumor activity as compared to tisotumab vedotin alone or cisplatin alone (FIG. 1A-E).

TABLE A

Statistical analysis

| | Mann-Whitney Day 38 p value | Mantel-Cox p value |
|---|---|---|
| Tisotumab vedotin, 4 mg/kg vs IgG1-MMAE, 4 mg/kg | <0.001 | 0.000 |
| Tisotumab vedotin, 2 mg/kg vs IgG1-MMAE, 4 mg/kg | <0.001 | 0.000 |
| Cisplatin, 4 mg/kg vs IgG1-MMAE, 4 mg/kg | <0.05 | 0.008 |
| Tisotumab vedotin, 4 mg/kg + cisplatin, 4 mg/kg vs tisotumab vedotin 4 mg/kg | <0.01 | 0.001 |
| Tisotumab vedotin, 4 mg/kg + cisplatin, 4 mg/kg vs cisplatin 4 mg/kg | <0.001 | 0.000 |
| Tisotumab vedotin, 2 mg/kg + cisplatin, 4 mg/kg vs tisotumab vedotin 2 mg/kg | <0.01 | 0.007 |
| Tisotumab vedotin, 2 mg/kg + cisplatin, 4 mg/kg vs cisplatin 4 mg/kg | <0.001 | 0.000 |

Example 2: Anti-Tumor Activity of Tisotumab Vedotin in Combination with a Platinum-Based Agent in a Bladder Cancer Mouse Model The combination of tisotumab vedotin with a platinum-based agent such as cisplatin was evaluated herein for the treatment of bladder cancer.

Materials and Methods

The in vivo anti-tumor efficacy of tisotumab vedotin in combination with cisplatin was evaluated in a PDX mouse model in female Crl:NMRI-Foxn1$^{nu}$ (Envigo RMS SARL, France) nude mice (Charles River Discovery Research Services). Xenografts were derived from tumor specimens from cancer patients. Establishment and characterization of the PDX model was performed following primary implantation into nude mice. Tumor xenografts were passaged approximately three to five times until establishment of stable growth patterns. Tumor fragments were obtained from xenografts in serial passage in nude mice. Tumors were cut into fragments of 3-4 mm diameter and placed in phosphate-buffered saline (PBS) until subcutaneous implantation. A bladder cancer PDX model (bladder xenograft model BXF1036; Charles River Discovery Research Services) was used in this experiment. Tumor size was determined by caliper measurement at least two times a week and tumor volume was calculated as 0.52×length×width. When tumors reached the volume of 50-250 mm$^3$, mice were randomized in 5 groups (10 mice per treatment group). Mice were treated with the following: 1) tisotumab vedotin alone at a dose level of 0.5 mg/kg provided on day 1 of treatment; 2) cisplatin alone at a dose of 2 mg/kg provided on day 1 and day 8 of treatment; 3) tisotumab vedotin at a dose level of 0.5 mg/kg provided on day 1 of treatment in combination with cisplatin at a dose of 2 mg/kg provided on day 1 and day 8 of treatment; 4) IgG1 isotype control at a dose of 0.5 mg/kg provided on day 1 of treatment; or 5) IgG1-MMAE control at a dose of 0.5 mg/kg provided on day 1 of treatment. IgG1 isotype control, IgG1-MMAE control and tisotumab vedotin were each in PBS and injected intravenously. Cisplatin was in 0.9% NaCl and injected subcutaneously. Mice were observed for clinical signs of illness. Mice were housed in individually ventilated (IVC) cages, with a maximum of five mice per cage, and identified by ear tags.

To determine whether there were statistically significant differences between tumor volumes in control and treatment groups, tumor volumes in the treatment groups were compared with those in the control groups (e.g., IgG1-MMAE control, tisotumab vedotin alone or cisplatin alone) using Mann-Whitney analysis at the last day that all groups were intact, i.e., day 25. Statistical analysis of the difference between groups treated with tisotumab vedotin in combination with cisplatin and groups treated with either tisotumab vedotin alone or cisplatin alone was performed on day 32.

Tumor progression was plotted in a Kaplan-Meier plot, with a cut-off set at a tumor volume >500 mm$^3$. Kaplan-Meier curves for mice treated with tisotumab vedotin in combination with cisplatin was compared to mice treated with IgG1-MMAE control, tisotumab vedotin alone or cisplatin alone using Mantel-Cox analysis on Kaplan-Meier plots.

Results

Figure 2A:
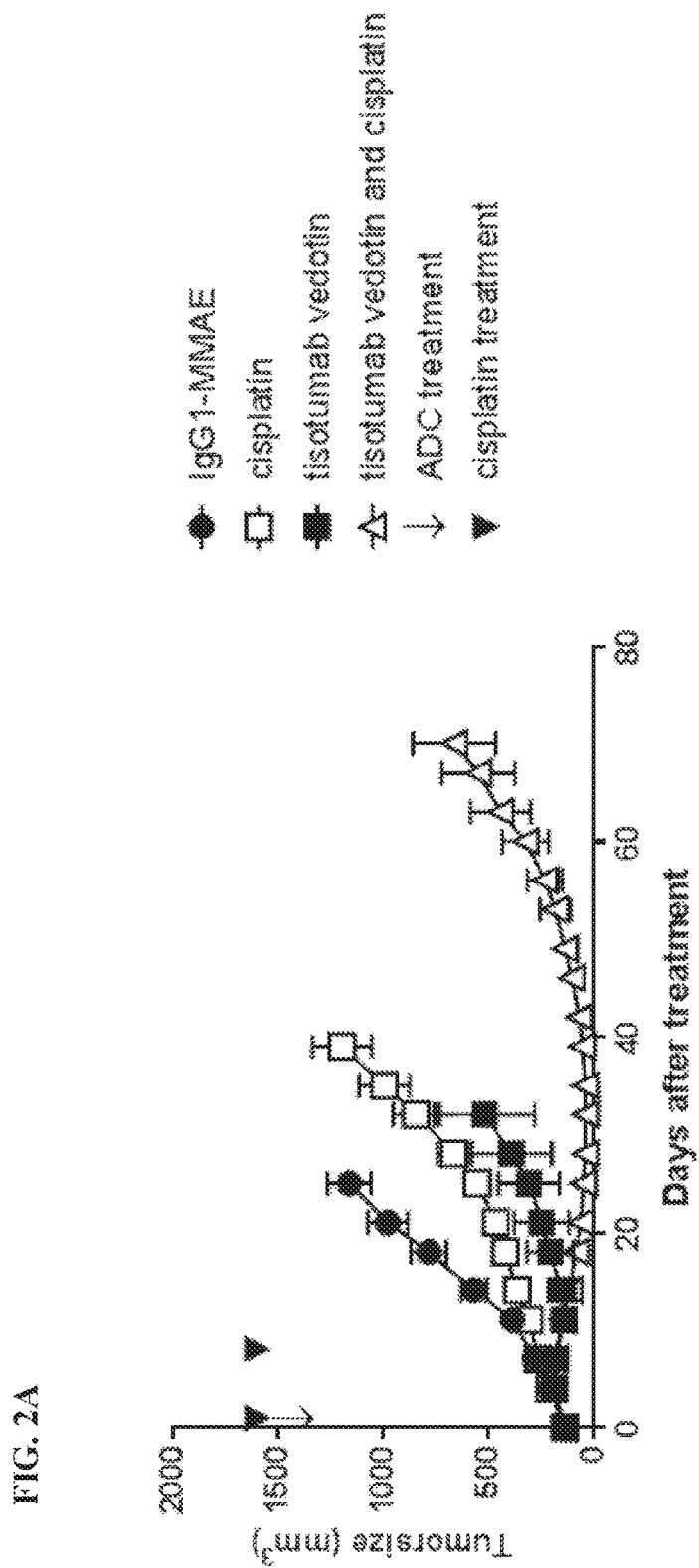
FIG. 2A-D is a graph showing the anti-tumor activity of the combination of tisotumab vedotin and cisplatin in a bladder cancer mouse model. A) Average tumor size in the mice after treatment with IgG1-MMAE control (filled black circle), cisplatin (empty black square), tisotumab vedotin (filled black square) or tisotumab vedotin combined with cisplatin (empty black triangle). Black inverted arrow indicates day of administration of tisotumab vedotin dose. Black filled inverted triangle indicates day of administration of cisplatin dose. Tumor burden was assessed by caliper measurements. Error bars indicate standard error of the mean. B) Mean tumor size in mice on Day 25 after treatment with IgG1-MMAE control, tisotumab vedotin, cisplatin, or tisotumab vedotin combined with cisplatin. C) Mean tumor size in mice on Day 32 after treatment with tisotumab vedotin or tisotumab vedotin combined with cisplatin. D) Percent tumor free survival with a tumor size cut-off 500 mm$^3$ in mice treated with IgG1-MMAE control, tisotumab vedotin alone, cisplatin alone, tisotumab vedotin combined with cisplatin.
Figure 2B:
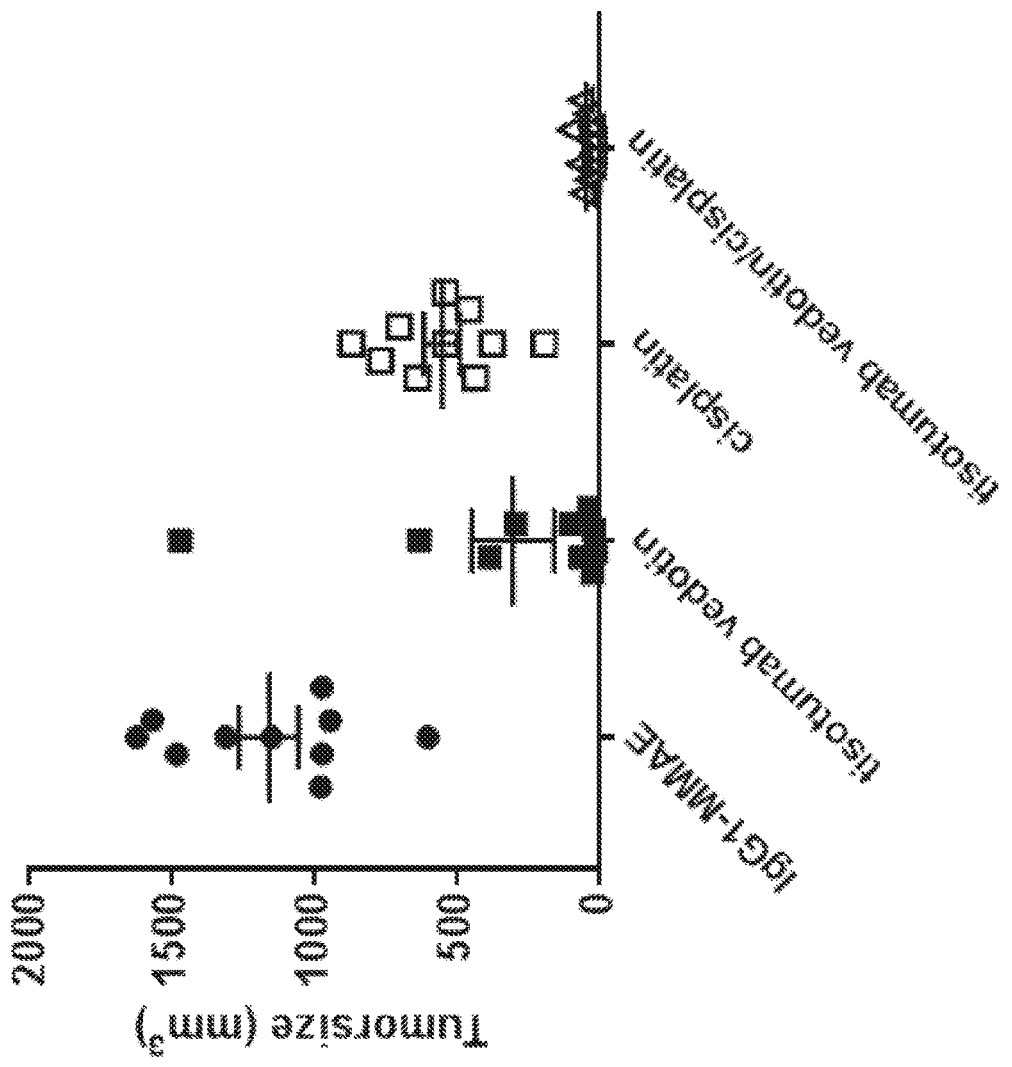
Figure 2C:
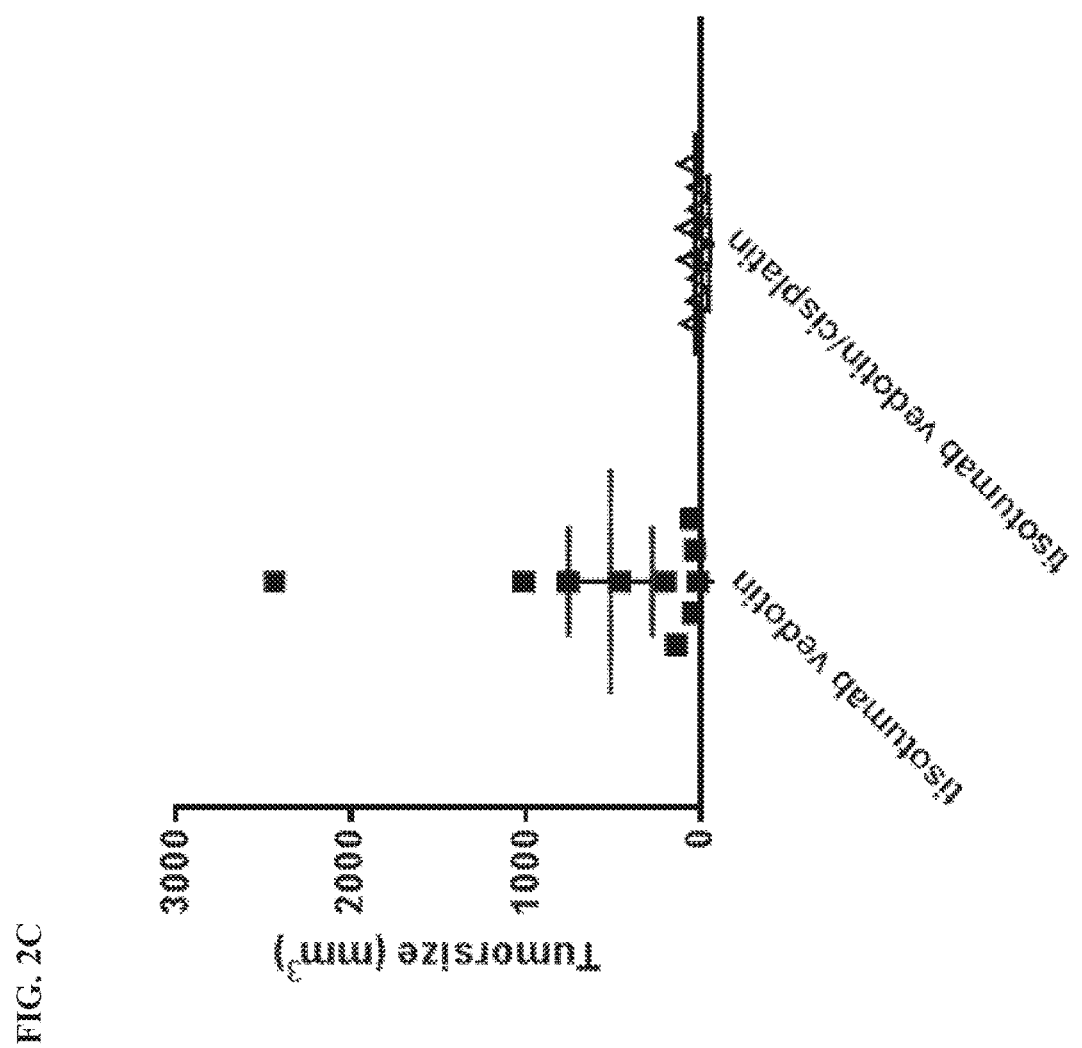
Figure 2D:
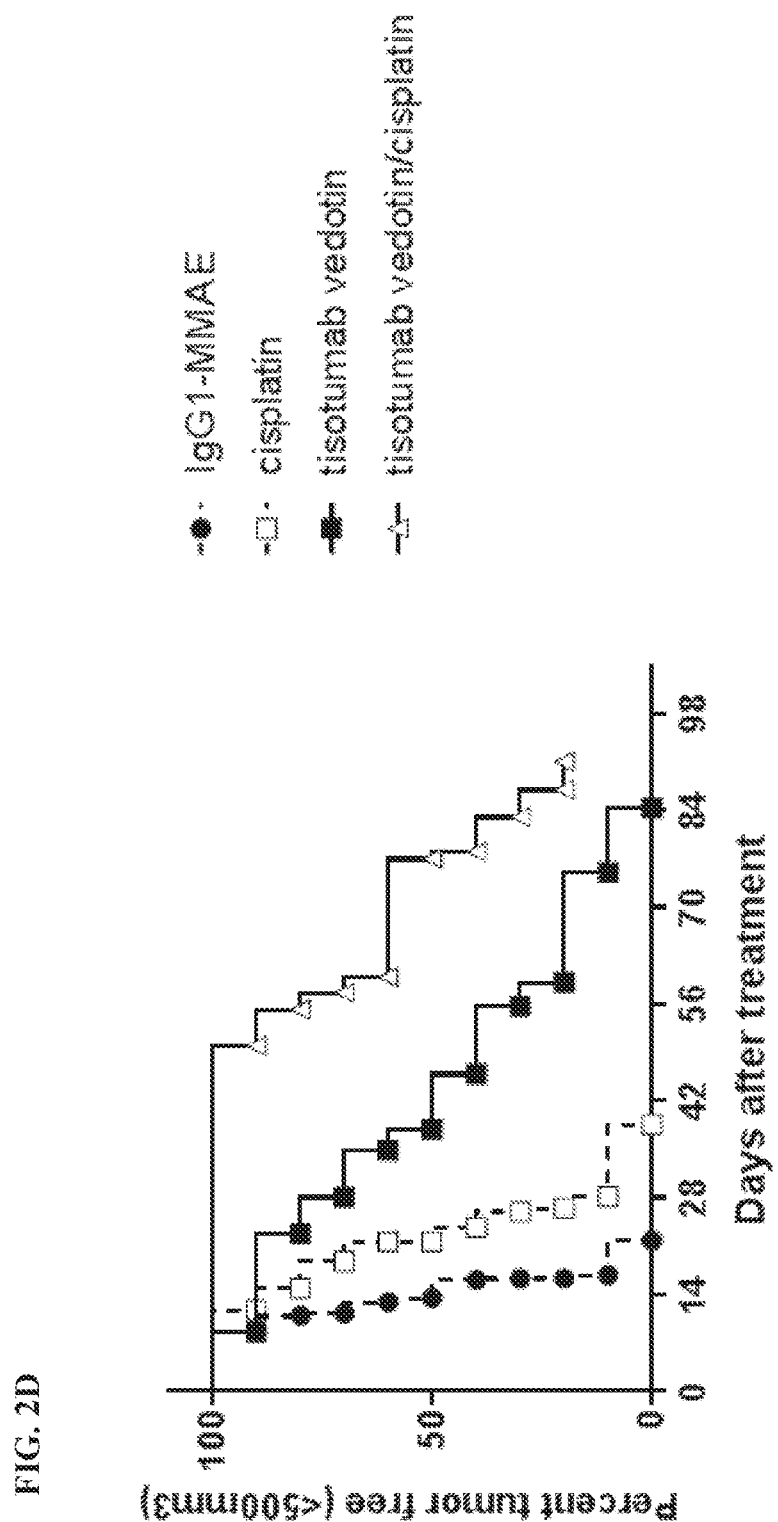

Treatment with tisotumab vedotin alone efficiently inhibited tumor growth (FIG. 2A-C) and prolonged survival (FIG. 2D) in a PDX model for bladder cancer. Treatment with cisplatin alone (FIG. 2A-C) also inhibited tumor growth and prolonged survival (FIG. 2D). Treatment with tisotumab vedotin in combination with cisplatin enhanced anti-tumor activity in a PDX model for bladder cancer as compared to tisotumab vedotin alone or cisplatin alone (FIG. 2A-D). Results of statistical analyses are shown in Table B.

TABLE B

| Statistical analysis | | |
|---|---|---|
| | Mann-Whitney p value | Mantel-Cox p value |
| Mann-Whitney Day 25 | | |
| Tisotumab vedotin (0.5 mg/kg) vs IgG1-MMAE (0.5 mg/kg) | <0.001 | <0.0001 |
| Cisplatin (2 mg/kg) vs IgG1-MMAE (0.5 mg/kg) | <0.0001 | <0.01 |
| Tisotumab vedotin + cisplatin vs IgG1-MMAE | <0.0001 | <0.0001 |

TABLE B-continued

| Statistical analysis | | |
|---|---|---|
| | Mann-Whitney p value | Mantel-Cox p value |
| Mann-Whitney Day 32 | | |
| Tisotumab vedotin + cisplatin vs tisotumab vedotin | 0.0089 | 0.011 |
| Tisotumab vedotin + cisplatin vs cisplatin | <0.001 | <0.0001 |

Example 3: Anti-Tumor Activity of Tisotumab Vedotin in Combination with a Platinum-Based Agent in a Cervical Cancer Mouse Model The combination of tisotumab vedotin with a platinum-based agent such as carboplatin was evaluated herein for the treatment of cervical cancer.

Materials and Methods

The in vivo anti-tumor efficacy of tisotumab vedotin in combination with carboplatin was evaluated in a patient-derived xenograft (PDX) mouse model in female BALB/c nude mice (Crown Bioscience [Taicang] Inc.). Xenografts were derived from tumor specimens from cancer patients. Tumor fragments were obtained from xenografts in serial passage in nude mice. Tumors were cut into fragments of 2-4 mm diameter and placed in phosphate-buffered saline (PBS) until subcutaneous implantation. A cervical cancer PDX model (HuPrime® cervical xenograft model CV1248 [P3]; Crown Bioscience Inc.) was used in this experiment. Tumor size was determined by caliper measurement at least two times a week and tumor volume was calculated as 0.5×length× width$^2$. When tumors reached an average volume of 150 mm$^3$, mice were randomized in 7 groups (10 mice per treatment group). The day of randomization was designated day 0. Mice were treated with the following by intravenous injections: 1) tisotumab vedotin alone at a dose level of 2 mg/kg, provided on day 0, day 7 and day 14; 2) carboplatin (Selleck Chemicals, cat. no. S121511) alone at a dose of 40 mg/kg or 80 mg/kg, provided on day 0, day 7 and day 14; 3) tisotumab vedotin at a dose level of 2 mg/kg, provided on day 0, day 7 and day 14 in combination with carboplatin at a dose of 40 mg/kg or 80 mg/kg, provided on day 0, day 7 and day 14; 4) IgG1 isotype control at a dose of 2 mg/kg provided on day 0, day 7 and day 14; or 5) IgG1-MMAE control at a dose of 2 mg/kg provided on day 0, day 7 and day 14. Mice were observed for clinical signs of illness. Mice were housed in individually ventilated (IVC) cages, up to a maximum of five mice per cage and identified by ear tags. To determine whether there were statistically significant differences between tumor volumes in control and treatment groups, tumor volumes in the treatment groups were compared with those in the control group (e.g., treatment groups vs IgG1-MMAE control) and combination treatment groups were compared with groups treated with either of the compounds alone, using Mann-Whitney analysis at the last day that all groups were intact, i.e., day 20. For analysis of progression-free survival time (tumor size cut-off 750 mm$^3$), Mantel-Cox analysis was performed on Kaplan-Meier plots.

Figure 3A:
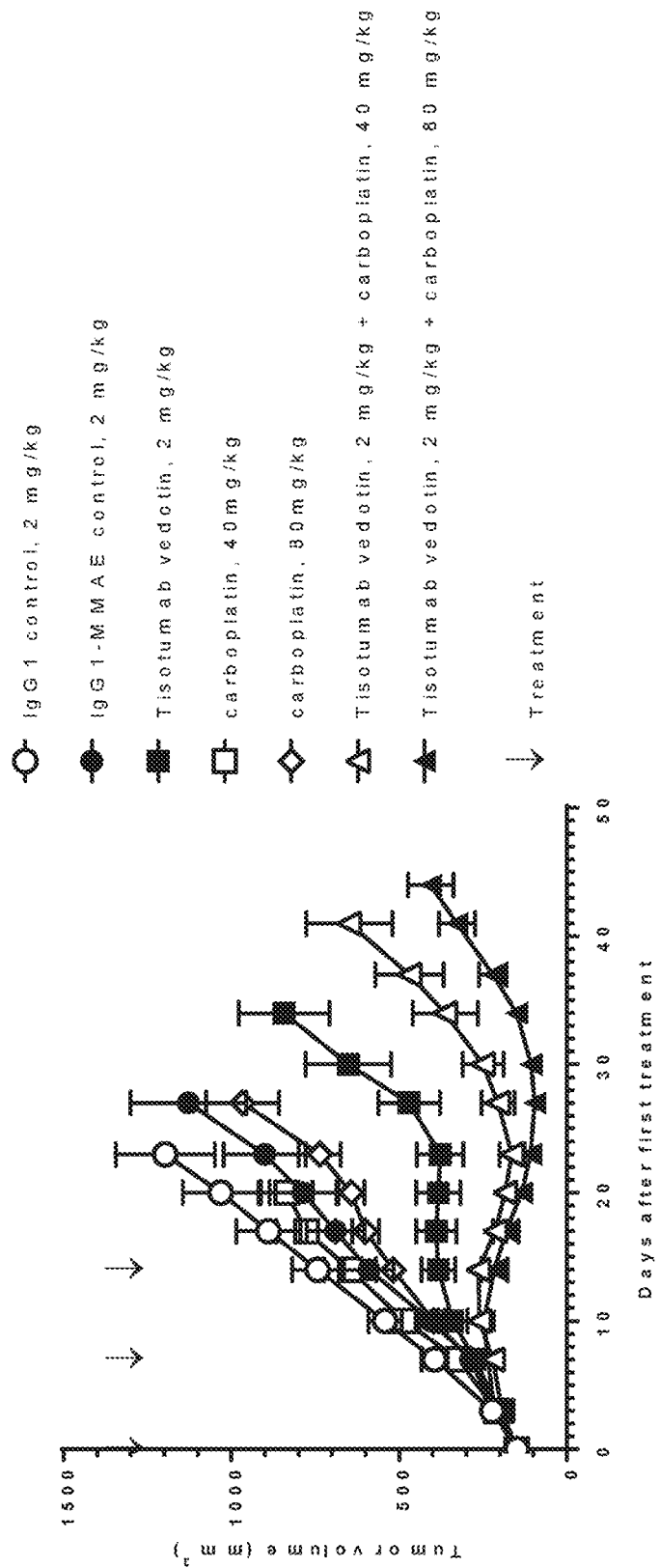
FIG. 3A-C is a graph showing the anti-tumor activity of the combination of tisotumab vedotin and carboplatin in a cervical cancer mouse model. A) Average tumor size in the mice after treatment with 2 mg/kg IgG1 control (open circle), 2 mg/kg IgG1-MMAE control (closed circle), 2 mg/kg tisotumab vedotin (closed square), 40 mg/kg carboplatin (open square), 80 mg/kg carboplatin (open diamond), 2 mg/kg tisotumab vedotin combined with 40 mg/kg carboplatin (open triangle) or 2 mg/kg tisotumab vedotin combined with 80 mg/kg carboplatin (closed triangle). Arrows indicate the day of treatment. Tumor burden was assessed by caliper measurements. Error bars indicate standard error of the mean. B) Average tumor size in mice at day 20 after treatment with 2 mg/kg IgG1 control (open circle), 2 mg/kg IgG1-MMAE control (closed circle), 2 mg/kg tisotumab vedotin (closed square), 40 mg/kg carboplatin (open square), 80 mg/kg carboplatin (open diamond), 2 mg/kg tisotumab vedotin combined with 40 mg/kg carboplatin (open triangle) or 2 mg/kg tisotumab vedotin combined with 80 mg/kg carboplatin (closed triangle). C) Percent progression-free survival with a tumor size cut-off at 750 mm$^3$ in mice treated with 2 mg/kg IgG1 control (open circle), 2 mg/kg IgG1-MMAE control (closed circle), 2 mg/kg tisotumab vedotin (closed square), 40 mg/kg carboplatin (open square), 80 mg/kg carboplatin (open diamond), 2 mg/kg tisotumab vedotin combined with 40 mg/kg carboplatin (open triangle) or 2 mg/kg tisotumab vedotin combined with 80 mg/kg carboplatin (closed triangle).
Figure 3B:
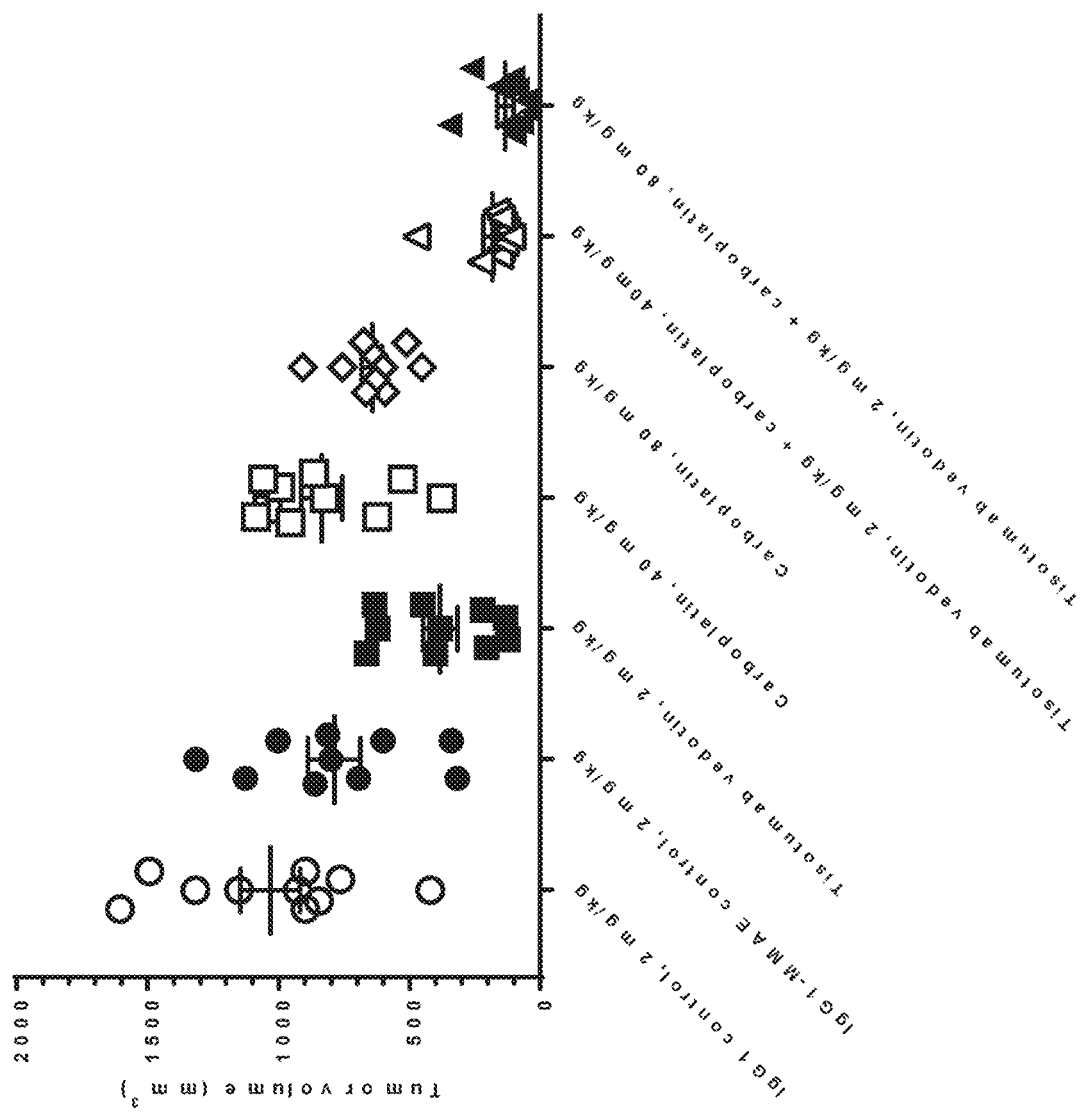
Figure 3C:
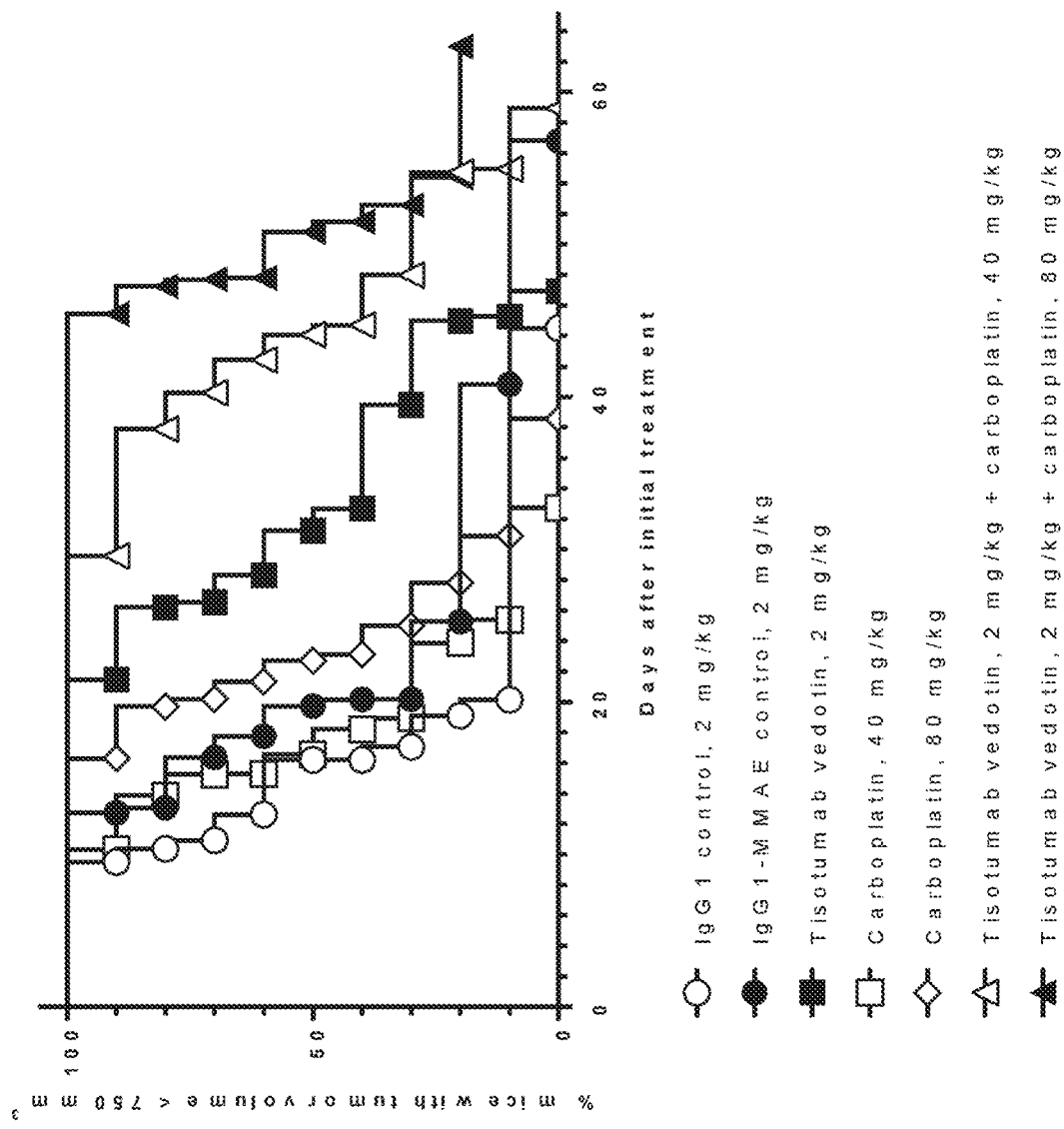

Treatment with 2 mg/kg tisotumab vedotin alone efficiently inhibited tumor growth (FIGS. 3A and 3B) in a mouse PDX model for cervical cancer. Treatment with carboplatin alone at a dose of 40 or 80 mg/kg did not inhibit tumor growth (FIGS. 3A and 3B). Treatment with 2 mg/kg tisotumab vedotin in combination with 40 mg/kg carboplatin efficiently enhanced anti-tumor activity as compared to carboplatin alone (FIGS. 3A and 3B). Combination of 2 mg/kg tisotumab vedotin and 80 mg/kg carboplatin efficiently enhanced anti-tumor activity as compared to carboplatin alone or tisotumab vedotin alone. All combinations enhanced progression-free survival time (tumor size cut-off 750 mm$^3$) as compared to the single agents (FIG. 3C). Results of statistical analyses are shown in Table C.

TABLE C

Statistical analysis

|  | Average tumor volume Mann-Whitney Day 20 P value | Percentage of mice with tumor volume <750 mm$^3$ Mantel-Cox P value |
|---|---|---|
| Tisotumab vedotin vs IgG1-MMAE | 0.0068 | 0.171 |
| Carboplatin, 40 mg/kg vs IgG1-MMAE | 0.5787 | 0.340 |
| Carboplatin, 80 mg/kg vs IgG1-MMAE | 0.1716 | 0.900 |
| Tisotumab vedotin + carboplatin, 40 mg/kg vs IgG1-MMAE | <0.0001 | 0.019 |
| Tisotumab vedotin + carboplatin, 80 mg/kg vs IgG1-MMAE | <0.0001 | 0.003 |
| Tisotumab vedotin + carboplatin, 40 mg/kg vs tisotumab vedotin | 0.0524 | 0.029 |
| Tisotumab vedotin + carboplatin, 40 mg/kg vs carboplatin, 40 mg/kg | <0.0001 | 0.000 |
| Tisotumab vedotin + carboplatin, 80 mg/kg vs tisotumab vedotin | 0.0011 | 0.000 |
| Tisotumab vedotin + carboplatin, 80 mg/kg vs carboplatin, 80 mg/kg | <0.0001 | 0.000 | lishment and characterization of the PDX model was performed following primary implantation into nude mice. Tumor xenografts were passaged approximately three to five times until establishment of stable growth patterns. Tumor fragments were obtained from xenografts in serial passage in nude mice. Tumors were cut into fragments of 3-4 mm diameter and placed in PBS until subcutaneous implantation. Tumor size was determined by caliper measurement two times a week and tumor volume was calculated as 0.5×length× width. When tumors reached a volume of approximately 50-250 mm$^3$, mice were randomized into 7 groups of 10 mice per treatment group. Mice were administered the following treatments, all provided every week for four weeks (QW×4): 1) tisotumab vedotin alone at 2 mg/kg (intravenously); 2) carboplatin alone at 40 mg/kg (intraperitoneally); 3) tisotumab vedotin at 2 mg/kg (intravenously) in combination with carboplatin at 40 mg/kg (intraperitoneally); 4) IgG1 isotype control at 2 mg/kg (intravenously); or 5) IgG1-MMAE control at 2 mg/kg (intravenously).

Figure 4A:
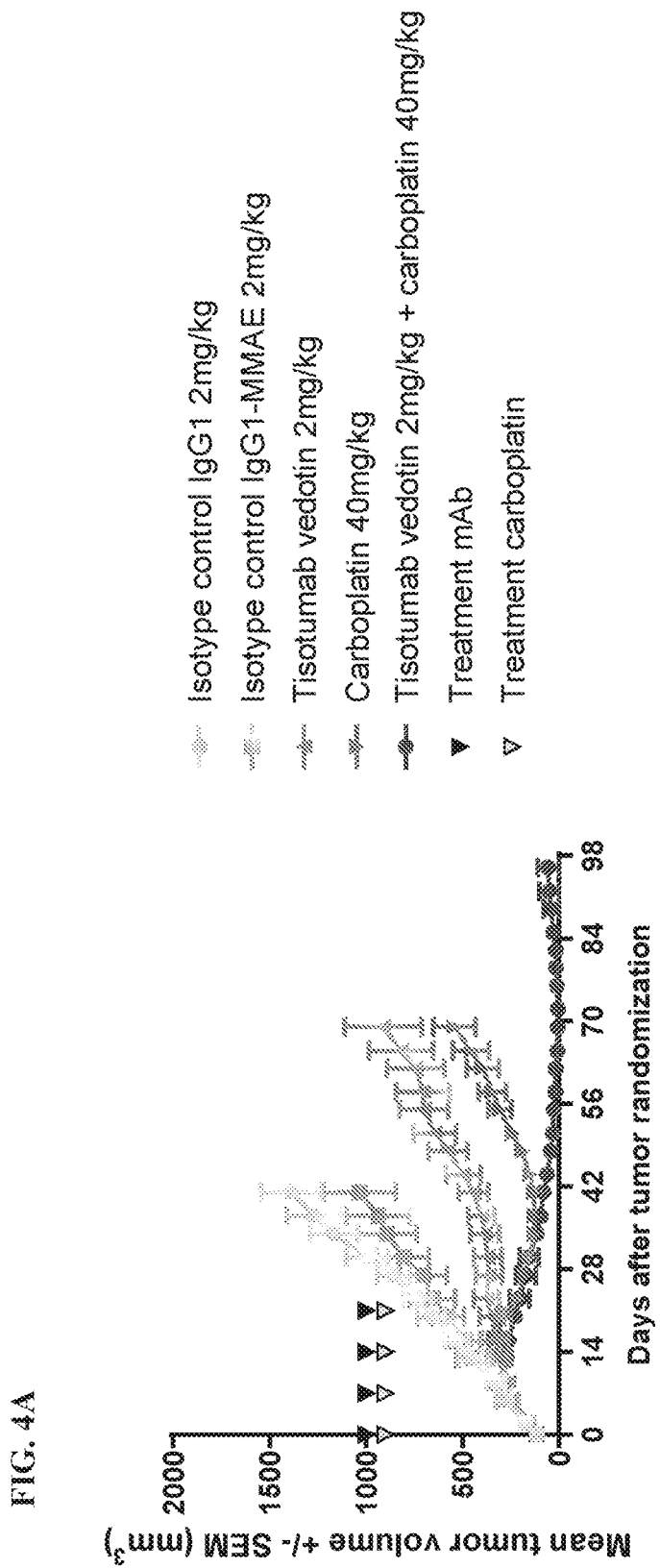
FIG. 4A-B is a graph showing the anti-tumor activity of the combination of tisotumab vedotin and cisplatin in a cervical cancer xenograft mouse model. A) Mean tumor volume in mice after treatment with 2 mg/kg IgG1 control (light gray circle), 2 mg/kg IgG1-MMAE control (gray square), 2 mg/kg tisotumab vedotin (light gray triangle), 40 mg/kg carboplatin (dark gray triangle), or 2 mg/kg tisotumab vedotin combined with 40 mg/kg carboplatin (black circle). Arrows indicate the day of treatment. Tumor burden was assessed by caliper measurements. Error bars indicate standard error of the mean. B) Percent progression-free survival with a tumor size cut-off of 1,000 m$^3$ in mice treated with 2 mg/kg IgG1 control, 2 mg/kg IgG1-MMAE control, 2 mg/kg tisotumab vedotin, 40 mg/kg carboplatin, or 2 mg/kg tisotumab vedotin combined with 40 mg/kg carboplatin.
Figure 4B:
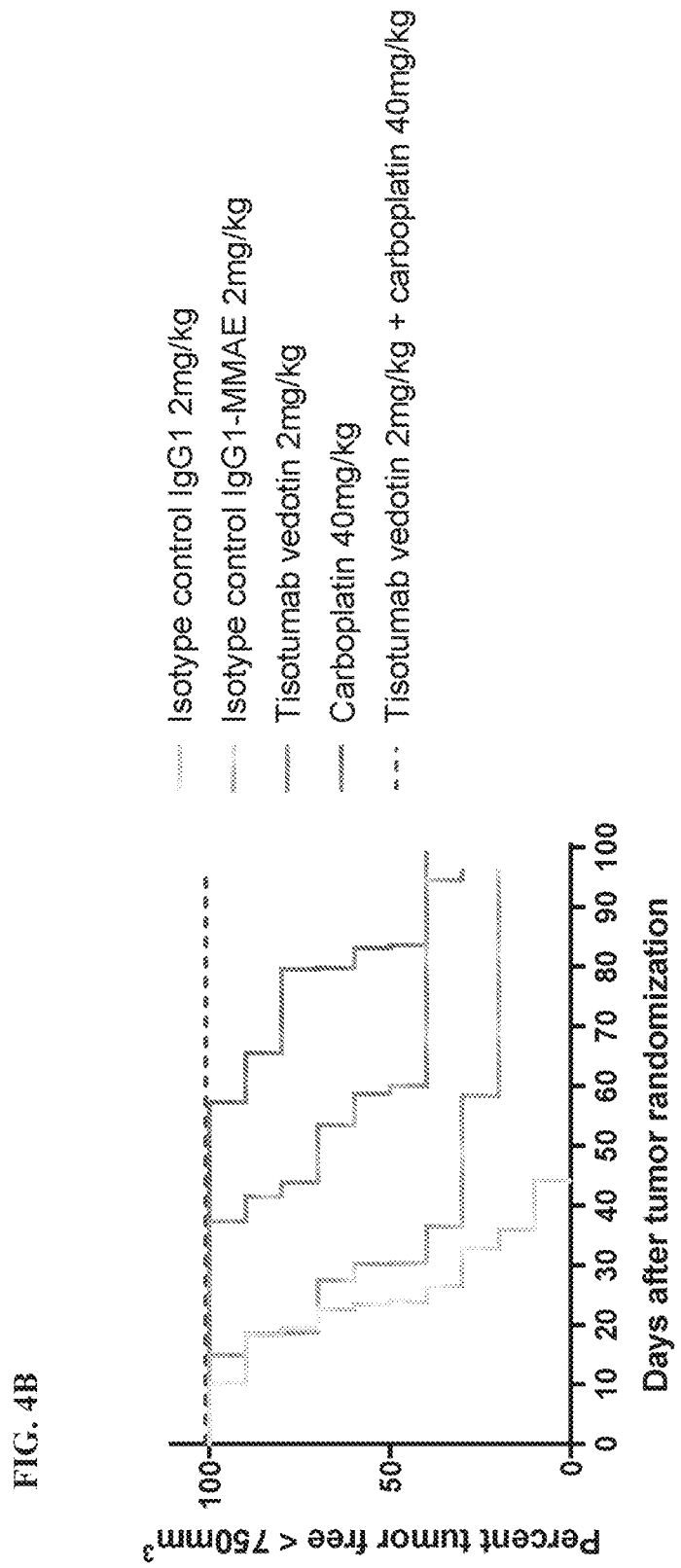

The mean tumor volume was plotted per treatment group (FIG. 4A). To determine whether there were statistically significant differences between tumor volumes in control and treatment groups, tumor volumes in the treatment groups were compared using Mann-Whitney analysis at the last day that all groups were intact (Table D). Combination treatment with tisotumab vedotin and carboplatin was significantly more potent than treatment groups with single agents in both models, as shown by a significant decrease in tumor size in mice that had received combination treatment. Progression-free survival analysis (using a tumor volume cut-off of 750 mm$^3$) demonstrated prolonged progression-free survival of the combination group compared to single agent treatment (Mantel-Cox analysis; FIG. 4B; Table D.)

TABLE D

Statistical analysis

| Treatment groups compared | | Day of analysis | Tumor volume Mann-Whitney P value | Kaplan Meier analysis for progression-free survival Mantel-Cox P value |
|---|---|---|---|---|
| Tisotumab vedotin, 2 mg/kg + carboplatin 40 mg/kg | vs IgG1-b12-MMAE, 2 mg/kg | Day 41 | <0.0001 | 0.000 |
| Tisotumab vedotin, 2 mg/kg + carboplatin 40 mg/kg | vs Tisotumab vedotin, 2 mg/kg | Day 69 | <0.0001 | 0.000 |
| Tisotumab vedotin, 2 mg/kg + carboplatin 40 mg/kg | vs Carboplatin, 40 mg/kg | Day 69 | <0.0001 | 0.004 |

Example 4: Anti-Tumor Activity of Tisotumab Vedotin in Combination with Carboplatin in a Cervical Cancer Mouse Xenograft Model The combination of tisotumab vedotin with platinum-based agent carboplatin was evaluated herein for the treatment of cervical cancer.

Materials and Methods

The in vivo anti-tumor efficacy of tisotumab vedotin in combination with carboplatin was evaluated in a patient-derived xenograft (PDX) cervical cancer mouse model in NMRI nu/nu mice (model CEXF663). Xenografts were derived from tumor specimens from cancer patients. Estab- Example 5: A Phase II Trial of Tisotumab Vedotin Alone or in Combination with a Platinum-Based Agent in First Line Recurrent or Stage IVB Cervical Cancer A Phase I/II trial demonstrated a robust efficacy and manageable safety profile for 2.0 mg/kg tisotumab vedotin administered to subjects with relapsed, recurrent, and/or metastatic cervical cancer (NCT02001623). That preliminary data suggests a positive benefit risk profile for that population of high unmet need. Further investigation of tisotumab vedotin as a monotherapy and in combination with therapeutic agents (e.g., a platinum-based agent) in a larger cohort of patients with cervical cancer is needed.

The efficacy, safety and tolerability of 1.3 mg/kg or 2.0 mg/kg tisotumab vedotin alone or in combination with carboplatin, a platinum-based agent, as first line therapy in subjects with recurrent or Stage IVB cervical cancer is evaluated herein.

Methods

This phase II, open-label, multi-center trial evaluates the efficacy, safety and tolerability of tisotumab vedotin alone or in combination with carboplatin in subjects with first line recurrent or Stage IVB squamous, adenosquamous, or adenocarcinoma of the cervix who are not amenable to curative treatment with surgery and/or radiation therapy and who have not received prior systemic therapy for their recurrent or Stage IVB disease. Subjects with recurrent disease who are candidates for curative therapy by means of pelvic exenteration are not eligible to participate in the trial.

Subjects are symmetrically allocated to one of four treatment groups. The allocation is done in a way that minimizes imbalance on disease status (metastatic/recurrent) and histology (squamous/non-squamous). Eligible subjects are treated with tisotumab vedotin 1.3 mg/kg Q3W, tisotumab vedotin 2.0 mg/kg Q3W, tisotumab vedotin 1.3 mg/kg Q3W+carboplatin AUC 5 Q3W or tisotumab vedotin 2.0 mg/kg Q3W+carboplatin AUC 5 Q3W. Treatment cycles occur every 21 days (±3 days). All treatment components are administered intravenously (IV). Approximately 60 subjects, age ≥18 years, are enrolled in the trial. The duration of the trial is approximately 7 years. Inclusion criteria and exclusion criteria for subjects enrolled in the trial are shown in Table 1.

TABLE 1

List of inclusion and exclusion criteria

| | |
|---|---|
| Inclusion Criteria | Must have recurrent or Stage IVB squamous, adenosquamous, or adenocarcinoma histologies of the cervix which are not amenable to curative treatment with surgery and/or radiation therapy.<br>Must have not received prior systemic therapy for recurrent or Stage IVB disease.<br>Note: Subjects are excluded if they are candidates for curative therapy by means of pelvic exenteration.<br>Note: Chemotherapy administered in the adjuvant or neoadjuvant setting, or in combination with radiation therapy is not counted as a prior systemic therapy.<br>Must have baseline measurable disease per RECIST v1.1.<br>Note: Lesions situated in a previously irradiated area are considered measurable if progression has been demonstrated in such lesions.<br>Age ≥18 years of age on day of signing informed consent.<br>Acceptable renal function: Calculated (Cockcroft-Gault) Glomerular Filtration Rate (GFR) >50 mL/min.<br>Acceptable liver function:<br>Alanine aminotransferase (ALT) and aspartate aminotransferase (AST) ≤2.5 × Upper Limit of Normal (ULN) (if liver tumor/metastases are present, then ≤5 × ULN is allowed);<br>Bilirubin ≤1.5 × ULN unless direct bilirubin ≤ institutional ULN, except in subjects diagnosed with Gilbert's syndrome, direct bilirubin ≤2 × ULN.<br>Acceptable hematological status:<br>Hemoglobin ≥5.6 mmol/L (9.0 g/dL).*<br>Absolute neutrophil count (ANC) ≥1500/μL (1.5 × 10⁹/L).<br>Platelet count ≥100 × 10⁹/L.<br>*Acceptable hematologic status must be met without erythropoietin dependency and without packed red blood cell (pRBC) transfusion within the last 2 weeks.<br>Acceptable coagulation status:<br>For subjects not on anti-coagulation therapy:<br>Activated partial thromboplastin time (aPTT) ≤1.25 × ULN.<br>International normalized ratio (INR) ≤1.2.<br>For subjects on anti-coagulation therapy:<br>aPTT ≤1.25 × ULN<br>INR: (1) Subjects on anti-coagulation therapy requiring laboratory assessments for dose titration (warfarin or other Vitamin K dependent anticoagulant agents) must be on a steady dose (no active titration) for at least 4 weeks prior to first planned dose of tisotumab vedotin and must have an INR ≤2.5 for eligibility. (2) Subjects on anti-coagulants that do not require laboratory assessments for dose titration must have an INR of ≤1.2 and do not need to be on a stable dose for ≥4 weeks prior to first planned dose of investigational medicinal product.<br>Concurrent use of prophylactic AcetylSalicylic Acid (ASA, e.g., aspirin) is prohibited for subjects on any type of anti-coagulation therapy.<br>Eastern Cooperative Oncology Group (ECOG) performance status of 0 or 1.<br>Life expectancy of ≥3 months<br>A female subject is eligible to participate if she is not pregnant, breastfeeding, or expecting to conceive children, or expecting to donate eggs for the purposes of assisted reproduction within the projected duration of the trial and for at least 6 months after the last trial administration and at least one of the following conditions applies:<br>Not a woman of childbearing potential (WOCBP)<br>A WOCBP must agree to use adequate contraception during and for 6 months after the last dose of trial treatment administration. Adequate contraception for women is defined as highly effective methods of contraception. In countries where two highly effective methods of contraception are required this will be an inclusion criterion.<br>Must provide a fresh specimen from a lesion not previously irradiated. Subjects for whom fresh samples cannot be obtained (e.g., inaccessible tumor or for safety concerns) may submit an archived specimen in place of the fresh tissue. Note: Aspirates are not acceptable.<br>Must have recovered from all AEs due to previous therapies to ≤grade 1. Subjects with ≤grade 2 neuropathy or alopecia are eligible.<br>Must be willing and able to adhere to the prohibitions and restrictions specified in this protocol.<br>Following receipt of verbal and written information about the trial, subjects must provide signed informed consent before any trial-related activity is carried out. |
| Exclusion Criteria | Clinically relevant bilateral hydronephrosis which cannot be alleviated by ureteral stents or percutaneous drainage.<br>Have clinical signs or symptoms of gastrointestinal obstruction and requires parenteral hydration and/or nutrition.<br>Hematological: Known past or current coagulation defects leading to an increased risk of bleeding; diffuse alveolar hemorrhage from vasculitis; known bleeding diathesis; ongoing major bleeding; trauma with increased risk of life-threatening bleeding or history of severe head trauma or intracranial surgery within 8 weeks of trial entry.<br>Ophthalmological: Active ocular surface disease at baseline. Subjects with prior history of cicatricial conjunctivitis or Steven Johnson Syndrome are not eligible to participate.<br>Cardiovascular: Clinically significant cardiac disease including unstable angina, acute myocardial infarction within 6 months prior to screening; any medical history of congestive heart failure (Grade III or IV as classified by the New York Heart Association), any medical history of decreased cardiac ejection fraction of <45%; a marked baseline prolongation of QT/QTc interval (e.g., repeated demonstration of a QTc interval >450 msec), a complete left bundle branch block (defined as a QRS interval ≥120 msec in left bundle branch block form) or an incomplete left bundle branch block.<br>Other cancers: Known past or current malignancy other than inclusion diagnosis, except for: Non-invasive basal cell or squamous cell skin carcinoma; noninvasive, superficial bladder cancer; any cancer with a complete response (CR) of >5 years duration.<br>Known active CNS metastases and/or carcinomatous meningitis. Subjects with previously treated brain metastases may participate provided they are radiologically stable, (i.e., without evidence of progression) for at least 28 days by repeat imaging (note that the repeat imaging should be performed |

TABLE 1-continued

List of inclusion and exclusion criteria during trial screening), subjects should be clinically stable, and should not require steroid treatment for at least 14 days prior to first dose of trial treatment.
Prior therapy:
Any prior treatment with MMAE-derived drugs.
Has received prior para-aortic radiation.
Prior radiotherapy (with the exception of para-aortic radiation) within 2 weeks (14 days) of start of trial treatment. Subjects must have recovered from all radiation-related toxicities, not require corticosteroids, and not have had radiation pneumonitis. A 1-week washout is permitted for palliative radiation (≤2 weeks of radiotherapy) to non-CNS disease.
Has received prior systemic anti-cancer therapy including investigational agents within 4 weeks (28 days) prior to the first dose of trial treatment.
Surgery/procedures: major surgery within 4 weeks (28 days) or minor surgery within 7 days prior to the first dose of trial treatment. Subjects must have recovered adequately from the toxicity and/or complications from the intervention prior to starting trial treatment. Subjects who have planned major surgery during the treatment period must also be excluded from the trial.
Other: Ongoing significant, uncontrolled medical condition; clinically significant active viral, bacterial or fungal infection requiring IV or oral (PO) treatment with antimicrobial therapy ending less than 7 days prior to first trial treatment administration;
Has intolerance to tisotumab vedotin or its excipients and severe hypersensitivity for carboplatin.
Has a history or current evidence of any condition, therapy, or laboratory abnormality that might confound the results of the trial, interfere with the subject's participation for the full duration of the trial, or is not in the best interest of the subject to participate, in the opinion of the treating investigator.
Has known psychiatric or substance abuse disorders that would interfere with cooperating with the requirements of the trial.
A WOCBP who has a positive pregnancy test (e.g., within 72 hours) prior to treatment. If the urine test is positive or cannot be confirmed as negative, a serum pregnancy test will be required. Subjects that are postmenopausal or permanently sterilized can be considered as not having reproductive potential.

Carboplatin is provided as a solution for intravenous infusion. It is delivered as a 1 hour infusion at a dosage of AUC 5 mg/mL per minute. The calculated dosage for carboplatin will be based upon a subject's glomerular filtration rate (GFR in mL/min) and target area under the concentration versus time curve (AUC in mg/mL min) by Calvert. GFR may be estimated by calculated creatinine clearance or based upon local institutional standards. Subjects who have ≥10% weight change from baseline or who experience CTCAE≥grade 2 renal toxicity (serum creatinine >1.5×ULN) require recalculation of the carboplatin dose for subsequent cycles. Subjects should receive pre-medication for carboplatin per institutional standard of care. Tisotumab vedotin administration by intravenous infusion begins at least 30 minutes after the administration of carboplatin. Lyophilized vials containing 40 mg of tisotumab vedotin are stored in a refrigerator at 2° C. to 8° C. Tisotumab vedotin is reconstituted in 4 ml of water leading to a reconstituted solution comprising 10 mg/mL tisotumab vedotin, 30 mM histidine, 88 mM sucrose, and 165 mM D-mannitol. The reconstituted antibody drug-conjugate solution has a pH of 6.0. The reconstituted tisotumab vedotin is diluted into a 0.9% NaCl 100 mL infusion bag according to the dose calculated for the subject. Intravenous infusion is completed within 24 hours after the tisotumab vedotin vial has been reconstituted. A 0.2 μm in-line filter is used for the intravenous infusion. The entire 100 mL volume from the prepared infusion bag is administered. No dead volume is provided.

Objectives and endpoints are described in Table 2. Subjects are treated until disease progression, toxicity, or withdrawal of consent. Imaging is obtained every 6 weeks for 32 weeks and then every 12 weeks thereafter, calculated from the date of first dose. On-trial imaging is continued until the subject experiences radiographic disease progression, begins a new anti-cancer therapy, withdraws consent or subject death. Tumor response is analyzed at three time points; futility assessment, early efficacy assessment, and primary efficacy assessment, respectively.

TABLE 2

Objectives and endpoints

| OBJECTIVES | ENDPOINTS |
|---|---|
| Primary | |
| Evaluate anti-tumor efficacy of tisotumab vedotin alone or in combination with carboplatin. | Objective Response Rate (ORR) as determined per Response Evaluation Criteria in Solid Tumors (RECIST) v1.1. |
| Secondary | |
| Assess safety and tolerability of tisotumab vedotin alone or in combination with carboplatin. | Frequency, duration, and severity of adverse events (AEs) and evaluation of safety laboratory parameters. |
| Evaluate durability of tisotumab vedotin alone or in combination with carboplatin. | Duration of Response (DOR) per RECIST v1.1. Time to Response (TTR) per RECIST v1.1. |
| Evaluate clinical response with tisotumab alone or in combination with carboplatin. | Progression free survival (PFS) per RECIST v 1.1. Overall Survival (OS). |
| To evaluate the pharmacokinetics (PK) and immunogenicity of tisotumab vedotin alone and in combination with carboplatin. | TPK and anti-drug antibodies (ADA) associated with tisotumab vedotin alone and in combination with carboplatin. |
| Exploratory | |
| Explore relationship between biomarkers and clinical response. | TF in tumor biopsies, circulating TF, proteomic analyses and genomic signatures. |
| Assess potential pharmacodynamic biomarkers. | Circulating tissue factor (TF) and proteomic analyses. |

For subjects that do not tolerate the protocol-specified dosing schedule, dose reductions are permitted for tisotumab vedotin in order to allow the subject to continue treatment with tisotumab vedotin alone or in combination with carboplatin (Table 3). The dose of carboplatin may also be reduced (Table 4).

TABLE 3

Tisotumab vedotin dose reduction schedule

| Current Dose of Tisotumab Vedotin | Reduced Dose of Tisotumab Vedotin |
|---|---|
| 2.0 mg/kg | 1.3 mg/kg |
| 1.3 mg/kg | 0.9 mg/kg* |

*No more than 2 dose reductions of tisotumab vedotin will be permitted. If an AE recurs after the second dose reduction of tisotumab vedotin, then the subject must be permanently discontinued from trial treatment.

TABLE 4

Carboplatin dose reduction schedule

| Current Dose of Carboplatin | Reduced Dose of Carboplatin |
|---|---|
| AUC 5 | AUC 4* |

*The subject must be discontinued from carboplatin if an (S)AE related to carboplatin recurs and does not resolve to ≤grade 1 after treatment is held for greater than 12 weeks. Dose reductions below AUC 4 are not permitted.

Three adverse events of special interest were identified during treatment with tisotumab vedotin alone in a previous trial: 1) ocular adverse events; 2) adverse events of peripheral neuropathy; and 3) adverse events of bleeding.

For ocular AEs: AEs of grade 1-2 conjunctivitis were frequently reported in relation to treatment with tisotumab vedotin. Implementation of a comprehensive mitigation plan and preventive measures substantially reduced both the frequency and severity of ocular adverse events. In the present trial, in order to prevent ocular AEs, all subjects in both treatment groups (i.e., tisotumab vedotin alone or in combination with carboplatin) must adhere to the following ocular pre-medication guidelines: 1) use of preservative-free lubricating eye drops during the whole treatment phase of the trial (i.e., from first dose of tisotumab vedotin until the safety follow-up visit). Lubricating eye drops should be administered according to the product prescribing information; 2) it is recommended not to wear contact lenses while treated with tisotumab vedotin from the first dose until a safety follow-up visit; 3) use of refrigerator-based eye cooling pads during infusion, e.g. THERA PEARL Eye Mask or similar, to be applied immediately before infusion in accordance with the instructions provided with the eye cooling pads; 4) administration of local ocular vasoconstrictor before infusion (brimonidine tartrate 0.2% eye drops or similar, 3 drops in each eye immediately prior to start of infusion; otherwise to be used in accordance with the product prescribing information). If the subject does not tolerate ocular vasoconstrictors due to adverse reactions, continued treatment with these may be stopped; and 5) application of steroid eye drops (dexamethasone 0.1% eye drops or equivalent) during the first 3 days of each treatment cycle (i.e., first drop to be given before start of tisotumab vedotin infusion; continue treatment for 72 hours thereafter). Steroid eye drops should be administered as 1 drop in each eye, 3 times daily, for 3 days, or used in accordance with the product prescribing information. The guidelines for ocular AEs are shown in Table 5.

TABLE 5

Dose modification and toxicity management guidelines for ocular adverse events.

| Adverse Event & Toxicity Grade (CTCAE v4.0) | Action Taken with Tisotumab Vedotin | Action Taken with Carboplatin | Guidelines for Treatment Prescribed by the Ophthalmologist |
|---|---|---|---|
| Conjunctivitis | | | |
| Conjunctivitis grade 1 | Hold dosing until event is managed effectively. Continue tisotumab vedotin at the same dose level. | Continue. | Local ophthalmologist must prescribe frequent dosing of preservative-free topical steroid drops. |
| Conjunctivitis grade 2 $1^{st}$ occurrence | Hold dosing until event has improved to ≤grade 1. Continue tisotumab vedotin at the same dose level. | Continue. | Local ophthalmologist must prescribe frequent dosing (every second hour) of preservative free topical steroid drops in conjunction with preservative free antibiotic prophylaxis such as chloramphenicol until the local ophthalmologist deems necessary. |
| Conjunctivitis grade 2 $2^{nd}$ occurrence | Hold dose of tisotumab vedotin: If the event has improved to baseline within 6 weeks (calculated from the onset date of the $2^{nd}$ grade 2 event), reduce next dose of tisotumab vedotin according to Table 3. If the event does not improve to ≤grade 1 baseline within 6 weeks (calculated from the onset date of the $2^{nd}$ grade 2 event), permanently discontinue tisotumab vedotin. | Withhold until event has improved to ≤grade 1. Continue carboplatin at the same dose level. | |
| Conjunctivitis grade 2 $3^{rd}$ occurrence | Permanently discontinue tisotumab vedotin. | Withhold until event has improved to ≤grade 1. Continue carboplatin at the same dose level. | |
| Conjunctivitis ≥grade 3 | Permanently discontinue tisotumab vedotin. | Withhold until event has improved to ≤grade 1. Continue carboplatin at the same dose level. | |
| Keratitis | | | |
| Keratitis grade 1 or 2 $1^{st}$ occurrence | Hold tisotumab vedotin until event has improved to ≤grade 1. Reduce tisotumab vedotin according to Table 3. | Withhold until event has improved to ≤grade 1. Continue carboplatin at the same dose level. | The local ophthalmologist must prescribe frequent dosing (every second hour) of preservative free topical steroid drops in conjunction with preservative |

TABLE 5-continued

Dose modification and toxicity management guidelines for ocular adverse events.

| Adverse Event & Toxicity Grade (CTCAE v4.0) | Action Taken with Tisotumab Vedotin | Action Taken with Carboplatin | Guidelines for Treatment Prescribed by the Ophthalmologist |
|---|---|---|---|
| Keratitis ≤grade 2 2nd occurrence | Hold tisotumab vedotin until event has improved to ≤grade 1. Reduce tisotumab vedotin again according to Table 3. | Withhold until event has improved to ≤grade 1. Continue carboplatin at the same dose level. | free antibiotic prophylaxis such as chloramphenicol until the local ophthalmologist deems necessary. |
| Keratitis ≤grade 2 3rd occurrence | Permanently discontinue tisotumab vedotin. Contact sponsor to discuss continuation of carboplatin alone. | Withhold until event has improved to ≤grade 1. Continue carboplatin at the same dose level. | |
| Keratitis ≥grade 3 | Permanently discontinue tisotumab vedotin. Contact sponsor to discuss continuation of carboplatin alone. | Withhold until event has improved to ≤grade 1. | |
| Conjunctival ulceration and ophthalmological findings of fluorescent patches must be handled as below ||||
| Any grade 1st occurrence | Hold tisotumab vedotin until event is managed effectively. Reduce tisotumab vedotin according to Table 3. | Withhold until event has improved to ≤grade 1. | The local ophthalmologist must prescribe frequent dosing (every second hour) of preservative free topical steroid drops in |
| Any grade ≥2nd occurrence | If symptoms do not stabilize/improve after dose reduction, the subject must permanently discontinue tisotumab vedotin. | Withhold until event has improved to ≤grade 1. | conjunction with preservative free antibiotic prophylaxis such as chloramphenicol until the local ophthalmologist deems necessary. |
| Symblepharon must be handled as below ||||
| Any grade | Permanently discontinue tisotumab vedotin. Contact sponsor to discuss continuation of carboplatin alone. | Withhold until event has improved to ≤grade 1. | Consult local ophthalmologist immediately. |
| All other ocular toxicities ||||
| All other ocular toxicities grade 1 | Hold dosing until event is managed effectively. Continue tisotumab vedotin at the same dose level. | Continue. | Local ophthalmologist must prescribe frequent dosing (every second hour) of preservative free topical steroid drops in |
| All other ocular toxicities grade 2 1st occurrence | Hold tisotumab vedotin until event is managed effectively. Reduce tisotumab vedotin according to Table 3. | Continue. | conjunction with preservative free antibiotic prophylaxis such as chloramphenicol until the local ophthalmologist deems necessary. |
| All other ocular toxicities grade 2 2nd occurrence | Hold dose of tisotumab vedotin: If the event has improved to baseline within 6 weeks, reduce next dose of tisotumab vedotin according to Table 3. If the event does not improve to baseline within 6 weeks, permanently discontinue tisotumab vedotin. | Withhold until event has improved to ≤grade 1. Continue carboplatin at the same dose level. | |
| All other ocular toxicities grade 2 3rd occurrence | Permanently discontinue tisotumab vedotin. | Withhold until event has improved to ≤grade 1. Continue carboplatin at the same dose level. | Consult local ophthalmologist immediately. |
| All other ocular toxicities ≥grade 3 | Permanently discontinue tisotumab vedotin. | Withhold until event has improved to ≤grade 1. Continue carboplatin at the same dose level. | |

For AEs of peripheral neuropathy (including neuropathy peripheral; peripheral sensory neuropathy; peripheral motor neuropathy; polyneuropathy): Peripheral neuropathy is a well-known adverse reaction to treatment with platinum and taxane based chemotherapies as well as MMAE-based ADCs and is reported in approximately 35% of subjects who received treatment with tisotumab vedotin. The majority of the reported cases are grade 1-2; however peripheral neuropathy is the leading cause of permanently discontinuation of tisotumab vedotin treatment. The guidelines for AEs or peripheral neuropathy are shown in Table 6.

For AEs of bleeding: Bleeding events are considered of special interest due to the mode of action of tisotumab vedotin. Epistaxis is the most common reported AE, however, nearly all of the cases are grade 1. Furthermore, clinically relevant perturbations in activated partial thromboplastin time (aPTT) or prothrombin time (PT) have not been observed. Dose modification and toxicity management guidelines are in place (Table 6).

Adverse events (AEs) such as increased bleeding, hemorrhage, elevated liver enzymes, mucositis, neutropenia, and peripheral neuropathy may be associated with tisotumab vedotin administration. Decreased platelet count, neutropenia, vomiting, and neuropathy may be associated with carboplatin administration. Dose modification and toxicity management guidelines for AEs associated with tisotumab vedotin and carboplatin combination treatment are provided such as bleeding, liver function abnormalities, mucositis, and neuropathy (Table 6) and for thrombocytopenia, neutropenia, vomiting (Table 7).

TABLE 6

Dose modification and toxicity management guidelines for ABs (bleeding, liver function abnormalities, mucositis, and neuropathy) associated with the carboplatin in combination with tisotumab vedotin treatment group

| AE (CTCAE v4.0) | Action Taken with Tisotumab Vedotin | Action Taken with Carboplatin |
|---|---|---|
| Bleeding Events | | |
| Control vital signs and ensure stabilization of the subject according to local standards. Prompt evaluation to identify the underlying etiology of the bleeding event. Management should ultimately be dictated by the underlying diagnosis. Control laboratory coagulation and hematologic parameters including PT, aPTT, fibrinogen, platelets, INR and hemoglobin as soon as possible. | | |
| All Subjects | | |
| Any grade pulmonary or CNS hemorrhage ≥grade 2 | Permanently discontinue tisotumab vedotin treatment. | Withhold until event resolved to ≤grade 1 AND platelets are within normal range. |
| Subjects not on anti-coagulation therapy | | |
| $1^{st}$ occurrence Hemorrhage (other)[1] ≥grade 3 | Hold dosing until: a) Bleeding has resolved. b) Blood hemoglobin level is stable. c) There is no bleeding diathesis that could increase the risk of continuing therapy. d) There is no anatomical or pathologic condition that can increase the risk of hemorrhage recurrence. When the above criteria are fulfilled the subject can resume treatment with tisotumab vedotin at the same dose as prior to the event. | Withhold until event resolved to ≤grade 1 AND platelets are within normal range. |
| ≥$2^{nd}$ occurrence Hemorrhage (other)[1] ≥grade 3 | Contact sponsor in order to discuss whether the subject may continue or must permanently discontinue tisotumab vedotin treatment. | Contact sponsor to determine if carboplatin alone can be continued. |
| Subjects on anti-coagulation therapy | | |
| INR >3.0 | Subjects on therapeutic anticoagulation whose INR is >3.0 prior to infusion of tisotumab vedotin must hold tisotumab vedotin until INR is ≤3.0. Subjects may resume tisotumab vedotin administration immediately after the INR is ≤3.0. Strongly consider holding anticoagulation until the above parameters are met. | None. |
| Hemorrhage (other)[1] ≥grade 3 | Hold anti-coagulation therapy. Contact sponsor in order to discuss whether the subject may continue or must permanently discontinue tisotumab vedotin treatment. | Contact sponsor to determine if carboplatin alone can be continued. |
| Liver parameters elevated (AST, ALT, or bilirubin) | | |
| ≥Grade 3 | Contact sponsor prior to administration of next dose to discuss if tisotumab vedotin should be reduced, delayed, or permanently discontinued. | Withhold until event resolves to grade 0 or 1. |
| Mucositis | | |
| Grade 3 | Hold tisotumab vedotin until event has improved to ≥grade 2. Treat according to local practice. | None |
| ≥Grade 4 | Permanently discontinue tisotumab vedotin. | Withhold until event resolves to grade 0 or 1. Contact sponsor to discuss continuation of carboplatin alone. |

TABLE 6-continued

Dose modification and toxicity management guidelines for ABs (bleeding, liver function abnormalities, mucositis, and neuropathy) associated with the carboplatin in combination with tisotumab vedotin treatment group

| AE (CTCAE v4.0) | Action Taken with Tisotumab Vedotin | Action Taken with Carboplatin |
|---|---|---|
| Peripheral neuropathy (including preferred terms as: neuropathy peripheral; peripheral sensory neuropathy; peripheral motor neuropathy; polyneuropathy) | | |
| Grade 2 and 3 Initial or worsening of pre-existing condition | Hold tisotumab vedotin until event has improved to ≤grade 1. Reduce next dose according to Table 3 | Hold dosing until event has improved to ≤grade 1. Reduce next dose according to Table 4. |
| ≥Grade 4 | Permanently discontinue tisotumab vedotin. | Permanently discontinue carboplatin. |

INR = International normalized ratio

[1] Any other hemorrhage with the exception of luminary or CNS hemorrhage.

TABLE 7

Dose modification and toxicity management guidelines for AEs (thrombocytopenia, neutropenia, vomiting) associated with the carboplatin in combination with tisotumab vedotin treatment group

| AE (CTCAE v4.0) | Toxicity grade (CTCAE v4.0) | Action taken to tisotumab vedotin | Action taken to carboplatin | Supportive Care |
|---|---|---|---|---|
| Hematological | | | | |
| Platelet Count Decreased | Grade 3 to 4 1st occurrence | Hold dosing until event has improved to ≤gr 1. Resume same DL. | Hold dosing until event has improved to ≤gr 1. Reduce next dose by 1 DL according to Table 4. | Transfusion of platelets may be used according to Institutional Standards. |
| | Grade 3 to 4 2nd occurrence | Hold dosing until event has improved to ≤gr 1 Resume same DL. | Discontinue. | |
| Neutropenia | Grade 3 to 4 1st occurrence | Hold dosing until event has improved to ≤gr 1. Resume same DL. | Hold dosing until event has improved to ≤gr 1. Reduce next dose by 1 DL according to Table 4. | Administer colony-stimulating factors according to Institutional Standards. |
| | Grade 3 to 4 2nd occurrence | Hold dosing until event has improved to ≤gr 1. Contact sponsor to discuss dose reduction or discontinuation of tisotumab vedotin. | Discontinue. | |
| Febrile Neutropenia | Grade 3[1] | Hold dosing until fever has resolved and neutrophil count has improved to >500/mm³. Resume same DL. | Hold dosing until fever has resolved and neutrophil count has improved to >500/mm³. Reduce next dose by 1 DL according to Table 4. | Administer corticosteroids (initial dose of 0.5-1 mg/kg prednisone or equivalent) followed by taper |

TABLE 7-continued

Dose modification and toxicity management guidelines for AEs (thrombocytopenia, neutropenia, vomiting) associated with the carboplatin in combination with tisotumab vedotin treatment group

| AE (CTCAE v4.0) | Toxicity grade (CTCAE v4.0) | Action taken to tisotumab vedotin | Action taken to carboplatin | Supportive Care |
|---|---|---|---|---|
| | Grade 4 | Hold dosing until event has improved to ≤gr 1. Contact sponsor to discuss dose reduction or discontinuation of tisotumab vedotin. | Discontinue. | Administer corticosteroids (initial dose of 1-2 mg/kg prednisone or equivalent) followed by taper |
| | | Non-hematologic | | |
| Vomiting | Grade 4 | Hold dosing until event has improved to ≤gr 1. Reduce by 1 DL according to Table 3 | Hold dosing until event has resolved. Reduce next dose by 1 DL according to Table 4. | Strong consideration should be given to the administration of prophylactic antiemetic therapy according to Institutional Standards. |

DL = dose level;
gr = grade

[1]Discontinue carboplatin upon recurrence of ≥grade 3 event. Contact sponsor to discuss dose reduction or discontinuation of tisotumab vedotin.

---

What is claimed is:

1. A method of treating cancer in a subject, the method comprising administering to the subject a platinum-based agent and an antibody-drug conjugate that binds to tissue factor (TF), wherein the antibody-drug conjugate comprises an anti-TF antibody or an antigen-binding fragment thereof conjugated to a monomethyl auristatin.

2. The method of claim 1, wherein the antibody-drug conjugate is administered at a dose ranging from about 0.9 mg/kg to about 2.1 mg/kg.

3. The method of claim 2, wherein the antibody-drug conjugate is administered at a dose of about 1.3 mg/kg.

4. The method of claim 2, wherein the antibody-drug conjugate is administered at a dose of about 2.0 mg/kg.

5. The method of claim 1, wherein the antibody-drug conjugate is administered once about every 1 week, once about every 2 weeks, once about every 3 weeks or once about every 4 weeks.

6. The method of claim 1, wherein the platinum-based agent is administered at a dose between about AUC=4 and about AUC=6.

7. The method of claim 6, wherein the platinum-based agent is administered a dose of about AUC=5.

8. The method of claim 1, wherein the platinum-based agent is administered once about every 1 week, once about every 2 weeks, once about every 3 weeks or once about every 4 weeks.

9. The method of claim 1, wherein the cancer is bladder cancer.

10. The method of claim 1, wherein the cancer is cervical cancer.

11. The method of claim 1, wherein the monomethyl auristatin is monomethyl auristatin E (MMAE).

12. The method of claim 1, wherein the anti-TF antibody or antigen-binding fragment thereof of the antibody-drug conjugate comprises a heavy chain variable region and a light chain variable region, wherein the heavy chain variable region comprises:
   (i) a CDR-H1 comprising the amino acid sequence of SEQ ID NO:1;
   (ii) a CDR-H2 comprising the amino acid sequence of SEQ ID NO:2; and
   (iii) a CDR-H3 comprising the amino acid sequence of SEQ ID NO:3; and
wherein the light chain variable region comprises:
   (i) a CDR-L1 comprising the amino acid sequence of SEQ ID NO:4;
   (ii) a CDR-L2 comprising the amino acid sequence of SEQ ID NO:5; and
   (iii) a CDR-L3 comprising the amino acid sequence of SEQ ID NO:6, wherein the CDRs of the anti-TF antibody or antigen-binding fragment thereof are defined by the IMGT numbering scheme.

13. The method of claim 1, wherein the anti-TF antibody or antigen-binding fragment thereof of the antibody-drug conjugate comprises a heavy chain variable region comprising the amino acid sequence of SEQ ID NO:7 and a light chain variable region comprising the amino acid sequence of SEQ ID NO:8.

14. The method of claim 1, wherein the anti-TF antibody of the antibody-drug conjugate is tisotumab.

15. The method of claim 1, wherein the antibody-drug conjugate further comprises a linker between the anti-TF antibody or antigen-binding fragment thereof and the monomethyl auristatin.

16. The method of claim 15, wherein the linker is attached to sulfhydryl residues of the anti-TF antibody obtained by partial reduction or full reduction of the anti-TF antibody or antigen-binding fragment thereof.

17. The method of claim 16, wherein the monomethyl auristatin is MMAE, wherein the linker is attached to MMAE, wherein the antibody-drug conjugate has the following structure:

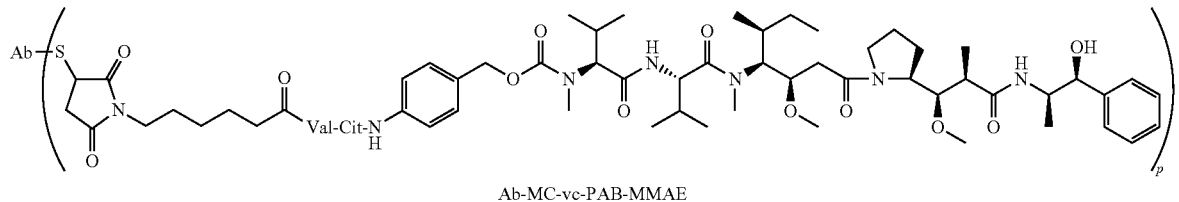

Ab-MC-vc-PAB-MMAE wherein p denotes a number from 1 to 8, S represents a sulfhydryl residue of the anti-TF antibody, and Ab designates the anti-TF antibody or antigen-binding fragment thereof.

18. The method of claim 1, wherein the antibody-drug conjugate is tisotumab vedotin.

19. The method of claim 1, wherein the platinum-based agent is selected from the group consisting of carboplatin, cisplatin, oxaliplatin, and nedaplatin.

20. The method of claim 1, wherein at least about 0.1%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, or at least about 80% of the cervical cancer cells express TF.

21. The method of claim 1, wherein one or more therapeutic effects in the subject is improved after administration of the antibody-drug conjugate and the platinum-based agent relative to a baseline.

22. The method of claim 21, wherein the one or more therapeutic effects is selected from the group consisting of: size of a tumor derived from the cervical cancer, objective response rate, duration of response, time to response, progression free survival, and overall survival.

23. The method of claim 1, wherein the subject has one or more adverse events and is further administered an additional therapeutic agent to eliminate or reduce the severity of the one or more adverse events.

24. The method of claim 23, wherein the one or more adverse events is hemorrhage, nausea, alopecia, conjunctivitis, keratitis, conjunctival ulceration, mucositis, constipation, decreased appetite, diarrhea, vomiting, neutropenia, febrile neutropenia, decreased platelet count, or increased bleeding.

25. The method of claim 23, wherein the one or more adverse events is conjunctivitis and/or keratitis and the additional agent is a preservative-free lubricating eye drop, an ocular vasoconstrictor and/or a steroid eye drop.

* * * * *

UNITED STATES PATENT AND TRADEMARK OFFICE
CERTIFICATE OF CORRECTION

PATENT NO. : 12,246,025 B2
APPLICATION NO. : 16/982008
DATED : March 11, 2025
INVENTOR(S) : Reshma Abdulla Rangwala et al.

It is certified that error appears in the above-identified patent and that said Letters Patent is hereby corrected as shown below:

In the Claims

At Column 113, Claim number 1, Line number 2, please delete "treating cancer" and insert --treating a cancer--.

At Column 113, Claim number 5, Line number 17, please delete "3 weeks or" and insert --3 weeks, or--.

At Column 113, Claim number 8, Line number 38, please delete "3 weeks or" and insert --3 weeks, or--.

At Column 113, Claim number 12, Line number 47, please delete "antibody or antigen-binding" and insert --antibody or the antigen-binding--.

At Column 113, Claim number 12, Line number 64, please delete "antibody or antigen-binding" and insert --antibody or the antigen-binding--.

At Column 114, Claim number 15, Line number 9, please delete "antibody or antigen-binding" and insert --antibody or the antigen-binding--.

At Column 114, Claim number 16, Line number 14, please delete "antibody or antigen-binding" and insert --antibody or the antigen-binding--.

At Column 114, Claim number 20, Line numbers 47-48, please delete "the cervical cancer cells express TF" and insert --cancer cells express TF, and wherein the cancer cells are cervical cancer cells--.

At Column 114, Claim number 22, Line number 54, please delete ":".

Signed and Sealed this
Twenty-seventh Day of May, 2025

Coke Morgan Stewart
*Acting Director of the United States Patent and Trademark Office*

At Column 115, Claim number 25, Line number 4, please delete "vasoconstrictor and/or" and insert --vasoconstrictor, and/or--.

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Phe Thr Phe Ser Asn Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Ser Gly Ser Gly Asp Tyr Thr
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Ala Arg Ser Pro Trp Gly Tyr Tyr Leu Asp Ser
1               5                   10

<210> SEQ ID NO 4

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ser Ser Arg
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Asn Ser Tyr Pro Tyr Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 8

Asp Ile Gln Met Thr Gln Ser Pro Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 9
<211> LENGTH: 25
<212> TYPE: PRT
<213> ORGANISM: Artificial Sequence
<220> FEATURE:
<223> OTHER INFORMATION: Synthetic Construct

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser
            20                  25

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Met Ser Trp Val Arg Gln Ala Pro Gly Lys Gly Leu Glu Trp Val Ser
1               5                   10                  15

Ser

<210> SEQ ID NO 11
<211> LENGTH: 38
<212> TYPE: PRT
<213> ORGANISM: Artificial Sequence
<220> FEATURE:
<223> OTHER INFORMATION: Synthetic Construct

<400> SEQUENCE: 11

Tyr Tyr Thr Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 12
<211> LENGTH: 11
<212> TYPE: PRT
<213> ORGANISM: Artificial Sequence
<220> FEATURE:

<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 26
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Leu Ser Ala Ser Ala Gly
1               5                   10                  15

Asp Arg Val Thr Ile Thr Cys Arg Ala Ser
            20                  25

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Leu Ala Trp Tyr Gln Gln Lys Pro Glu Lys Ala Pro Lys Ser Leu Ile
1               5                   10                  15

Tyr

<210> SEQ ID NO 15
<211> LENGTH: 36
<212> TYPE: PRT
<213> ORGANISM: Artificial Sequence
<220> FEATURE:
<223> OTHER INFORMATION: Synthetic Construct

<400> SEQUENCE: 15

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Phe Gly Gln Gly Thr Lys Leu Glu Ile Lys
1               5                   10